United States Patent
Sano et al.

(10) Patent No.: US 9,452,392 B2
(45) Date of Patent: Sep. 27, 2016

(54) GAS SEPARATION COMPOSITE MEMBRANE AND METHOD OF PRODUCING THE SAME, AND GAS SEPARATING MODULE, GAS SEPARATION APPARATUS AND GAS SEPARATION METHOD USING THE SAME

(71) Applicant: FUJIFILM CORPORATION, Minato-ku, Tokyo (JP)

(72) Inventors: Satoshi Sano, Kanagawa (JP); Ichiro Nagata, Kanagawa (JP); Keisuke Kodama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 72 days.

(21) Appl. No.: 14/457,577

(22) Filed: Aug. 12, 2014

(65) Prior Publication Data

US 2014/0345456 A1    Nov. 27, 2014

Related U.S. Application Data

(63) Continuation of application No. PCT/JP2013/053829, filed on Feb. 18, 2013.

(30) Foreign Application Priority Data

Feb. 17, 2012    (JP) .................................. 2012-033399

(51) Int. Cl.
*B01D 71/72* (2006.01)
*B01D 67/00* (2006.01)
(Continued)

(52) U.S. Cl.
CPC ............. *B01D 71/72* (2013.01); *B01D 53/228* (2013.01); *B01D 67/0006* (2013.01);
(Continued)

(58) Field of Classification Search
CPC .......... B01D 53/228; B01D 2053/221; B01D 67/0006; B01D 67/0079; B01D 67/009; B01D 69/125; B01D 69/148; B01D 71/64; B01D 71/70; B01D 71/72; B01D 2256/245; B01D 2257/504; B01D 2323/30; B01D 2323/34; B01D 2323/345; B01D 2323/40; C08G 73/1039; C08G 73/1042; C08G 73/1067; C08G 73/14; C08G 65/40; C07C 7/144; C07C 9/04
USPC .......................................................... 95/51
See application file for complete search history.

(56) References Cited

U.S. PATENT DOCUMENTS 5,009,934 A * 4/1991 Wenski .................. B01D 71/64
427/387
5,198,316 A * 3/1993 Wernet .................. B01D 71/64
210/651
(Continued)

FOREIGN PATENT DOCUMENTS

JP    2-164427 A    6/1990
JP    4-110029 A    4/1992
(Continued)

OTHER PUBLICATIONS

Communication dated Mar. 17, 2015 from the Japanese Patent Office in counterpart application No. 2013-028238.
(Continued)

*Primary Examiner* — Jason M Greene
(74) *Attorney, Agent, or Firm* — Sughrue Mion, PLLC

(57) ABSTRACT

A gas separation composite membrane, containing a gas-permeable supporting layer and a gas separating layer containing a crosslinked organic-inorganic hybrid resin over the gas-permeable supporting layer, in which the crosslinked organic-inorganic hybrid resin has a structure in which a polymer incorporating therein an oxanthrene unit, or a polyimide compound has been crosslinked via a specific crosslinking chain.

15 Claims, 1 Drawing Sheet

(51) Int. Cl.

| | |
|---|---|
| B01D 71/64 | (2006.01) |
| B01D 69/12 | (2006.01) |
| B01D 53/22 | (2006.01) |
| B01D 71/70 | (2006.01) |
| C07C 7/144 | (2006.01) |
| B01D 69/14 | (2006.01) |
| C08G 65/40 | (2006.01) |
| C08G 73/10 | (2006.01) |
| C08G 73/14 | (2006.01) |

(52) U.S. Cl.
CPC ....... *B01D 67/009* (2013.01); *B01D 67/0079* (2013.01); *B01D 69/125* (2013.01); *B01D 69/148* (2013.01); *B01D 71/64* (2013.01); *B01D 71/70* (2013.01); *C07C 7/144* (2013.01); *C08G 65/40* (2013.01); *C08G 73/1039* (2013.01); *C08G 73/1042* (2013.01); *C08G 73/1067* (2013.01); *C08G 73/14* (2013.01); *B01D 2053/221* (2013.01); *B01D 2256/245* (2013.01); *B01D 2257/504* (2013.01); *B01D 2258/025* (2013.01); *B01D 2258/0233* (2013.01); *B01D 2258/0283* (2013.01); *B01D 2323/30* (2013.01); *B01D 2323/34* (2013.01); *B01D 2323/40* (2013.01); *Y02C 10/10* (2013.01); *Y02C 20/20* (2013.01); *Y02P 20/152* (2015.11)

(56) References Cited

U.S. PATENT DOCUMENTS

| | | | | |
|---|---|---|---|---|
| 5,817,165 | A * | 10/1998 | Hachisuka | B01D 53/228 96/4 |
| 7,247,191 | B2 | 7/2007 | Koros et al. | |
| 7,619,042 | B2 | 11/2009 | Poe et al. | |
| 2003/0220188 | A1* | 11/2003 | Marand | B01D 53/228 502/60 |
| 2010/0270234 | A1 | 10/2010 | Liu et al. | |
| 2010/0326273 | A1* | 12/2010 | Liu | B01D 67/0079 95/45 |
| 2013/0047844 | A1* | 2/2013 | Zheng | B01D 71/64 95/45 |
| 2013/0255490 | A1* | 10/2013 | Matteucci | B01D 53/228 95/51 |

FOREIGN PATENT DOCUMENTS

| | | |
|---|---|---|
| JP | 4-110030 A | 4/1992 |
| JP | 7-236822 A | 9/1995 |
| JP | 8-52332 A | 2/1996 |
| JP | 9-173801 A | 7/1997 |
| JP | 10-87855 A | 4/1998 |
| JP | 2005-74317 A | 3/2005 |
| JP | 2007-44653 A | 2/2007 |
| JP | 2007-45969 A | 2/2007 |
| WO | 2006/025327 A1 | 3/2006 |
| WO | 2011/009919 A1 | 1/2011 |
| WO | 2013/015335 A1 | 1/2013 |
| WO | 2013/015336 A1 | 1/2013 |
| WO | 2013/015337 A1 | 1/2013 |
| WO | 2013/015338 A1 | 1/2013 |

OTHER PUBLICATIONS

Richard W. Baker, "Future Directions of Membrane Gas Separation Technology", Ind. Eng. Chem. Res., 2002, pp. 1393-1411, vol. 41, No. 6.

Richard W. Baker, et al., "Natural Gas Processing with Membranes: An Overview", Ind. Eng. Chem. Res., 2008, pp. 2109-2121, vol. 47, No. 7.

Chris J. Cornelius, et al., "Hybrid silica-polyimide composite membranes: gas transport properties", Journal of Membrane Science, 2002, pp. 97-118, vol. 202.

William J. Koros, et al., "Pushing the limits on possibilities for large scale gas separation: which strategies?", Journal of Membrane Science, 2000, pp. 181-196, vol. 175.

M. Marek, et al., "Crosslinked Ultra-Thin Polyimide Film as a Gas Separation Layer for Composite Membranes", Eur. Polym. J., 1997, pp. 1717-1721, vol. 33, No. 10-12.

Claudia Staudt-Bickel, et al., "Improvement of $CO_2/CH_4$ separation characteristics of polyimides by chemical crosslinking", Journal of Membrane Science, 1999, pp. 145-154, vol. 155.

Tomoyuki Suzuki, et al., "Physical and Gas Transport Properties of Novel Hyperbranched Polyimide-Silica Hybrid Membranes", Polymer Bulletin, 2005, pp. 139-146, vol. 53.

Yuri Yampolskii, et al., "Membrane Gas Separation", Johns Wiley & Sons Ltd., 2010, pp. 1-4.

International Search Report of PCT/JP2013/053829, dated May 7, 2013. [PCT/ISA/210].

* cited by examiner

GAS SEPARATION COMPOSITE MEMBRANE AND METHOD OF PRODUCING THE SAME, AND GAS SEPARATING MODULE, GAS SEPARATION APPARATUS AND GAS SEPARATION METHOD USING THE SAME

CROSS-REFERENCE TO RELATED APPLICATIONS

This application is a Continuation of PCT International Application No. PCT/JP2013/053829 filed on Feb. 18, 2013, which claims priority under 35 U.S.C. §119 (a) to Japanese Patent Application No. 2012-033399 filed on Feb. 17, 2012. Each of the above applications is hereby expressly incorporated by reference, in its entirety, into the present application.

TECHNICAL FIELD

The present invention relates to a gas separation composite membrane and a method of producing the same, and a gas separating module, a gas separation apparatus and a gas separation method using the same.

BACKGROUND ART

A raw material comprising a polymer compound has characteristic gas permeability for each raw material. Based on properties thereof, a desired gas component can be separated by allowing selective permeation by means of a membrane constituted of a specific polymer compound. As an industrial application embodiment of this gas separation membrane, study has been conducted for separating and recovering carbon dioxide from a large-scale carbon dioxide source in a thermal power station, a cement plant, a blast furnace in a steel plant or the like in relation to a global warming issue. Then, this membrane separation technique attracts attention as a solution to an environmental issue to allow achievement by relatively small energy. Meanwhile, natural gas or bio gas (gases generated by fermentation and anaerobic digestion of excreta of organisms, organic fertilizers, biodegradable substances, polluted water, garbages, energy crops, and the like) is mainly a mixed gas of methane and carbon dioxide. Study has been made so far for a membrane separation method as a means for removing an impurity such as carbon dioxide therein.

Specifically, study has been made for cellulose or polyimide as a raw material in purification of a natural gas. However, the membrane is plasticized under high pressure conditions and high carbon dioxide concentration in an actual plant, and a decrease of separation selectivity due to the plasticization has become a problem (see Non-Patent Literature 1, p. 313-322; and Non-Patent Literatures 2 and 3). In order to suppress plasticization of the membrane, introduction of crosslinked structure into a polymer compound constituting the membrane is known to be effective, and research has been continued for improvement in a separation membrane using a polyimide resin (see Non-Patent Literature 1, p. 3-27; and Patent Literature 1). In addition, specific examples of arts utilizing a membrane having a crosslinked structure for the gas separation membrane include arts described in Patent Literature 2, and Non-Patent Literatures 4, 5 and 6. In recent years, enhancement of performance due to organic-inorganic hybrid structures has been also studied (see Patent Literatures 2 to 4; and Non-Patent Literatures 7 and 8).

CITATION LIST

Patent Literatures

Patent Literature 1: U.S. Pat. No. 7,247,191
Patent Literature 2: US 2010/0326273
Patent Literature 3: WO 2006/025327
Patent Literature 4: U.S. Pat. No. 7,619,042

Non-Patent Literatures

Non-Patent Literature 1: Yuri Yampolskii, Benny Freeman, Membrane Gas Separation
Non-Patent Literature 2: Industrial. Engineering. Chemistry. Research. 2008, 47, 2109.
Non-Patent Literature 3: Industrial. Engineering. Chemistry. Research. 2002, 41, 1393.
Non-Patent Literature 4: Journal of Membrane Science. 1999, 155, 145.
Non-Patent Literature 5: Journal of Membrane Science. 2000, 175, 181.
Non-Patent Literature 6: European Polymer Journal, 1997, 33, 1717.
Non-Patent Literature 7: Polymer Bulletin. 2005, 53, 139.
Non-Patent Literature 8: Journal of Membrane Science. 2002, 202, 97.

DISCLOSURE OF THE INVENTION

Technical Problem

Incidentally, in order to constitute a practical gas separation membrane, sufficient gas permeability should be secured by processing a raw material into a thin layer. An attempt has been made so far for processing a single raw material into an asymmetric membrane, thereby processing a part contributing to separation into the thin layer referred to as a skin layer to satisfy high gas permeability, separation selectivity and also mechanical strength. However, the single raw material is difficult to be processed into one uniting these properties. Therefore, from viewpoints of performance and cost, a composite membrane is desirable in which separate raw materials bear a separation function and a function for providing the membrane with the mechanical strength, and the composite membrane is becoming mainstream in a reverse osmosis membrane for water treatment.

On the other hand, in the gas separation membrane, a study on composite membranes has not sufficiently been done. Further, there are also a small number of examples which provide findings, on a technique of utilizing a cross-linked-structure membrane for a separating layer that is being studied by the present inventors (see Patent Literatures 2 and 3, and Non-Patent Literatures 5, 6, 7 and 8). According to these disclosed methods, a high temperature of 100° C. or higher or a very long time is required to crosslinking in some cases. Therefore, these methods have been still insufficient for providing a practical gas separation membrane having excellent membrane-forming competence and also excellent durability or deterioration resistance, while maintaining high gas permeability and separation selectivity.

Further, there is room for improvement of use competence under high-pressure conditions (ordinarily 10 atmospheric pressure or higher, desirably 40 atmospheric pressure or higher) to be anticipated in actual purification of natural gas, and stability to impurities such as long chain hydrocarbons and toluene.

Introduction of organic-inorganic hybrid structures in order to provide durability is also getting attention, and for example, a study on a hybrid membrane with a hyper-branched polyimide structure is disclosed (see Non-Patent Literature 1 and a pamphlet of International Publication No. 2011/024908). However, the present inventors have confirmed that the membrane exhibits excellent separation selectivity, but causes a noticeable decline in gas permeability (see Comparative Examples described below). Under such circumstances, it is difficult to obtain a practical composite membrane because of inability to secure practical gas permeability without advanced thinning thereof. Further, each of the literatures does not refer to performance evaluation under such a high-pressure condition as anticipated in actual purification of natural gas as described above. According to confirmation, the present inventors have gotten the feeling of necessity to adjust a suitable crosslinked structure and crosslinkable functional group density in order to realize intended high-gas separation selectivity because plasticization of the polymer membrane and compression of free volume are caused under high-pressure conditions, and these are different from those under low pressure conditions.

In view of the above-described respects, the present invention addresses the provision of realizing high gas separation selectivity while keeping excellent gas permeability, and further providing use competence under high-pressure conditions and stability to plasticization-inducing impurities such as toluene. Further, the present invention addresses the provision of a gas separation composite membrane achieving a high membrane-forming competence; a method of producing the same, and a gas separation module using the same and a gas separation apparatus.

Solution to Problem

The above-described problems can be solved by the following means.

[1] A gas separation composite membrane, containing:
a gas-permeable supporting layer; and
a gas separating layer containing a crosslinked organic-inorganic hybrid resin, over the gas-permeable supporting layer,
wherein the crosslinked organic-inorganic hybrid resin has a structure in which a polymer incorporating therein an oxanthrene unit, or a polyimide compound has been crosslinked via a specific crosslinking chain, and the specific crosslinking chain contains a site represented by the following formula (A):

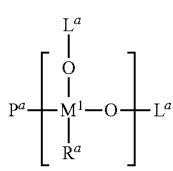

wherein $R^a$ represents an alkyl group, a cycloalkyl group, an aryl group, an alkoxy group, an aryloxy group, or *—O—**; the symbol "*" means a bonding hand with $M^1$ in formula (A); the symbol "**" means a connection site with an adjacent $M^1$; $M^1$ represents a metal atom selected from the group consisting of Si, Ge, Mg, Al, Ti, Zr and Sb; $P^a$ represents a polyimide compound or a polymer incorporating therein an oxanthrene unit; and $L^a$ represents a connection site with an adjacent $M^1$.

[2] The gas separation composite membrane as described in the above item [1], wherein a structural part derived from the polyimide compound contains a repeating unit represented by formula (I), and a repeating unit represented by formula (III-a) or (III-b):

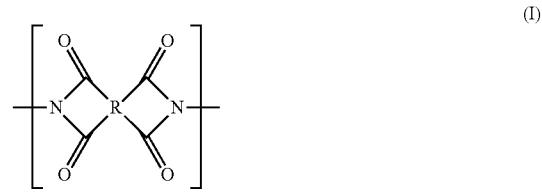

wherein, in formula (I), R is a group of atoms selected from groups represented by formulas (I-a) to (I-g);

wherein, in formulas (I-a) to (I-g), $X^1$ represents a single bond or a divalent linking group; Y represents a methylene group or a vinylene group; $R^1$ and $R^2$ each independently represent a hydrogen atom or a substituent, or may bond with each other to form a ring; and the symbol "*" represents a binding site with the carbonyl group of the imide in formula (I);

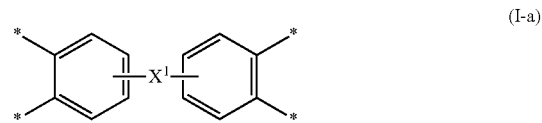

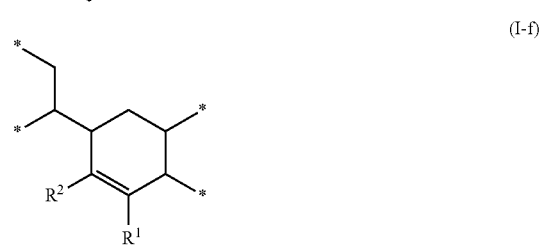

-continued

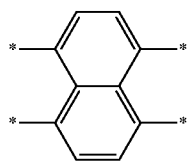
(I-g)

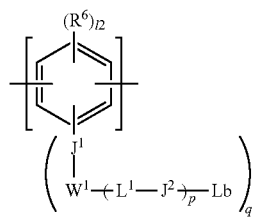
(III-a)

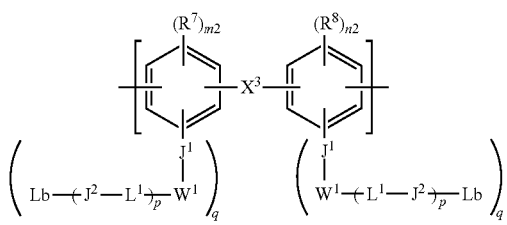
(III-b)

wherein $R^6$, $R^7$ and $R^8$ represent a substituent; $J^1$, $J^2$ and $W^1$ represent a single bond or a divalent linking group; l2, m2 and n2 represent an integer of from 0 to 3; $L^1$ represents a divalent linking group; p represents an integer of 0 or more; q represents an integer of 1 or more; $X^3$ represents a single bond or a divalent linking group; and Lb means a connection site with $M^1$ in formula (A).

[3] The gas separation composite membrane as described in the above item [2], wherein the structural part derived from the polyimide compound further contains a repeating unit represented by formula (II-a) or (II-b):

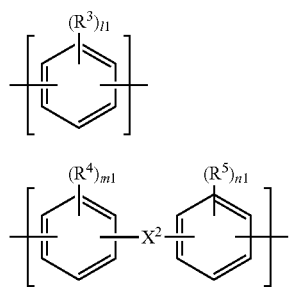

wherein $R^3$, $R^4$ and $R^5$ represent an alkyl group, a hydroxyl group, a carboxyl group, a sulfonic acid group, an amino group, a mercapto group, an amide group, an alkoxy group, a sulfone group, or a halogen atom; l1, m1 and n1 represent an integer of from 0 to 4; and $X^2$ represents a single bond or a divalent linking group.

[4] The gas separation composite membrane as described in the above item [1], wherein the polymer incorporating therein an oxanthrene unit is a resin with inherent microporosity (PIM).

[5] The gas separation composite membrane as described in the above item [1] or [4], wherein the polymer incorporating therein an oxanthrene unit contains a repeating unit represented by formula (IV-a), and a repeating unit represented by formula (IV-b):

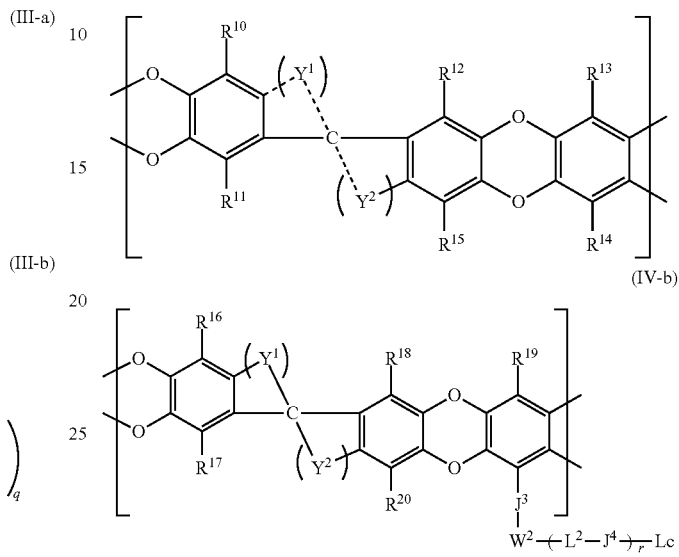

wherein $R^{10}$ to $R^{20}$ represent a hydrogen atom or a substituent; $J^3$, $J^4$ and $W^2$ represent a single bond or a divalent linking group; $L^2$ represents a divalent linking group; r represents an integer of 0 or more; $Y^1$ and $Y^2$ represent a group of atoms for forming a ring with the carbon atom and the benzene ring; Lc means a connection site with $M^1$ in formula (A).

[6] The gas separation composite membrane as described in any one of the above items [1] to [5],
wherein a gas to be supplied is a mixed gas of carbon dioxide and methane,
wherein a transmission rate of the carbon dioxide at 40° C. and 40 atmospheric pressure is more than 20 GPU, and
wherein a ratio of the transmission rate of the carbon dioxide to a transmission rate of the methane ($R_{CO2}/R_{CH4}$) is 15 or more.

[7] The gas separation composite membrane as described in any one of the above items [1] to [6], wherein the supporting layer contains a porous layer on a side of the gas separating layer and a nonwoven fabric layer on a side reverse thereto.

[8] The gas separation composite membrane as described in the above item [7], wherein the porous layer has a molecular weight cut-off of 100,000 or less.

[9] The gas separation composite membrane as described in any one of the above items [1] to [8], wherein a crosslinked site ratio [η] of the crosslinked organic-inorganic hybrid resin is 0.13 or more.

[10] The gas separation composite membrane as described in any one of the above items [1] to [9], wherein a crosslinking functional group density [γ] of a raw resin that constitutes the crosslinked organic-inorganic hybrid resin is from 0.7 to 0.95.

[11] The gas separation composite membrane as described in any one of the above items [1] to [10], wherein the crosslinked organic-inorganic hybrid resin is formed by using a compound represented by the following formula (O-1), (O-2), or (O-3) as a crosslinking agent that constitutes the crosslinking chain thereof:

$$H_2N-L^O-Si(R^O)_3 \quad \quad \text{O-1}$$

$$HS-L^O-Si(R^O)_3 \quad \quad \text{O-2}$$

$$CH_2=CH-L^O-Si(R^O)_3 \quad \quad \text{O-3}$$

wherein $L^O$ represents a single bond or a linking group; and $R^O$ represents an alkyl group, an aryl group, an alkoxy group, or an aryloxy group.

[12] A method of producing a gas separation composite membrane having a gas separating layer containing a crosslinked organic-inorganic hybrid resin over a gas-permeable supporting layer thereof, comprising:

coating a coating liquid containing a polyimide compound or a polymer incorporating therein an oxanthrene unit, and a crosslinking agent having a metal atom $M^1$ wherein $M^1$ represents a metal atom selected from the group consisting of Si, Ge, Mg, Al, Ti, Zr, and Sb, over the supporting layer; and irradiating an active radiation or applying heat to the coating liquid thereby inducing a crosslinking reaction.

[13] The method of producing the organic-inorganic hybrid gas separation composite membrane as described in the above item [12], wherein the crosslinking agent is a compound represented by formula (B):

$$A^2-L^3-\underset{\underset{R^{23}}{|}}{\overset{\overset{R^{21}}{|}}{M^1}}-R^{22} \quad \quad (B)$$

wherein $A^2$ represents a reactive group; $L^3$ represents a single bond or a divalent linking group; $R^{21}$, $R^{22}$ and $R^{23}$ represent an alkyl group, a cycloalkyl group, an aryl group, an alkoxy group, or an aryloxy group; and $M^1$ has the same meaning as that described above.

[14] The method of producing a gas separation composite membrane as described in the above item [13], wherein the crosslinking agent is a compound represented by formula (O-1), (O-2) or (O-3):)

$$H_2N-L^O-Si(R^O)_3 \quad \quad \text{O-1}$$

$$HS-L^O-Si(R^O)_3 \quad \quad \text{O-2}$$

$$CH_2=CH-L^O-Si(R^O)_3 \quad \quad \text{O-3}$$

wherein $L^O$ represents a single bond or a divalent linking group; and $R^O$ represents an alkyl group, an aryl group, an alkoxy group, or an aryloxy group.

[15] The method of producing the organic-inorganic hybrid gas separation composite membrane as described in any one of the above items [12] to [14], wherein the polyimide compound contains a repeating unit represented by formula (I), and a repeating unit represented by formula (VI-a) or (VI-b):

(I)

wherein, in formula (I), R is a group of atoms selected from groups represented by formulas (I-a) to (I-g);

wherein, in formulas (I-a) to (I-g), $X^1$ represents a single bond or a divalent linking group; Y represents a methylene group or a vinylene group; $R^1$ and $R^2$ each independently represent a hydrogen atom or a substituent, or may bond with each other to form a ring; and the symbol "*" represents a binding site with the carbonyl group of the imide in formula (I);

(I-a)

(I-b)

(I-c)

(I-d)

(I-e)

(I-f)

(I-g)

(VI-a)

(VI-b)

wherein $R^6$, $R^7$ and $R^8$ represent a substituent; $J^1$ represents a single bond or a divalent linking group; l2, m2 and n2 represent an integer of from 0 to 3; q represents an integer of 1 or more and 4 or less; $X^3$ represents a single bond or a divalent linking group; and $A^1$ represents a reactive group.

[16] The method of producing the organic-inorganic hybrid gas separation composite membrane as described in the above item [15], wherein the polyimide compound further contains a repeating unit represented by formula (II-a) or (II-b):

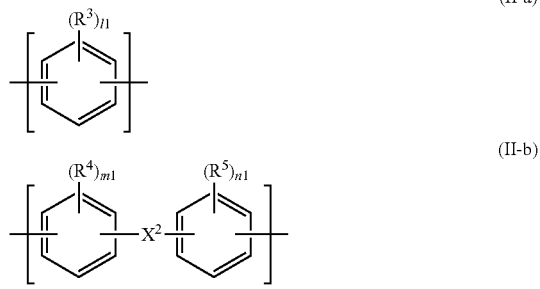

wherein $R^3$, $R^4$ and $R^5$ represent a substituent; l1, m1 and n1 represent an integer of from 0 to 4; and $X^2$ represents a single bond or a divalent linking group.

[17] The method of producing a gas separation composite membrane as described in any one of the above items [12] to [14], wherein the polymer incorporating therein an oxanthrene unit is a polymer containing a repeating unit represented by formula (V):

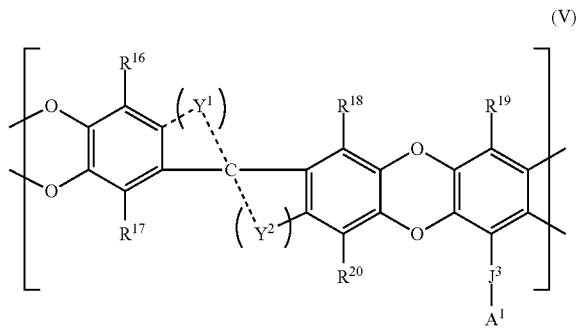

wherein $R^{16}$ to $R^{20}$ represent a hydrogen atom or a substituent; $J^3$ represents a single bond or a divalent linking group; $Y^1$ and $Y^2$ represent a group of atoms for forming a ring with the carbon atom and the benzene ring; and $A^1$ represents a hydroxy group, a carboxyl group, a sulfonic acid group, an alkenyl group, an alkynyl group, or a mercapto group.

[18] A gas separation module, containing the gas separation composite membrane as described in any one of the above items [1] to [11].

[19] A gas separation apparatus, containing the gas separation module as described in the above item [18].

[20] A gas separation method, which contains a step of selectively permeating carbon dioxide from a gas containing carbon dioxide and methane by using the gas separation composite membrane as described in any one of the above items [1] to [11].

When a plurality of substituents, linking groups or the like (hereinafter, referred to as "substituent or the like") represented by a specific symbol are described herein, or a plurality of substituents or the like are simultaneously or alternatively defined in the present specification, respective substituents or the like may be identical or different. Moreover, unless otherwise noted, when a plurality of substituents or the like are close, they may be linked with each other or subjected to ring condensation, thereby forming a ring. Further, when a repeating unit is shown by means of the formula, it means that one kind or two or more kinds of the repeating unit may be incorporated.

Advantageous Effects of Invention

The gas separation composite membrane according to the present invention has excellent gas permeability and yet, realizes high gas separation selectivity, and further has use competence under high-pressure conditions and stability to plasticization-inducing impurities such as toluene. Moreover, the present invention allows provision of a high-performance gas separating module and gas separation apparatus using the same. Further, a method of producing a gas separation composite membrane according to the present invention allows production of a gas separation composite membrane that develops the above-described high performance.

Other and further features and advantages of the invention will appear more fully from the following description, appropriately referring to the accompanying drawings.

MODE FOR CARRYING OUT THE INVENTION

The gas separation composite membrane of the present invention is comprised of a separation layer containing a crosslinked resin that has been crosslinked via a crosslinking chain having a specific inorganic component. Although the reason for exertion of the above-described excellent function effects includes unexplained portion, it is presumed as follows.

In a separated gas of a natural gas or the like, ordinarily a trace of moisture and impurities such as benzene, toluene, and higher aliphatic chain hydrocarbons are contained. It is thought that even in this case, in the organic-inorganic hybrid membrane of the present invention, advantages of the organic resin which forms a main skeleton are maintained, and yet the swelling is suppressed due to water-repellent/oil-repellent effect of the inorganic component which forms a crosslinking chain and thereby performance degradation is effectively suppressed. Further, it is thought that a homogeneous and degradation-controlled crosslinked form is realized in a membrane, and the crosslinked form exhibits a sufficient durability even in the use at high pressure, and yet has a good bendability, and also conforms to a thin supporting layer, and thereby exhibits an excellent performance.

Hereinafter, the present invention is described in detail based on a preferred embodiment thereof.

[Composite Membrane]

Figure 1:
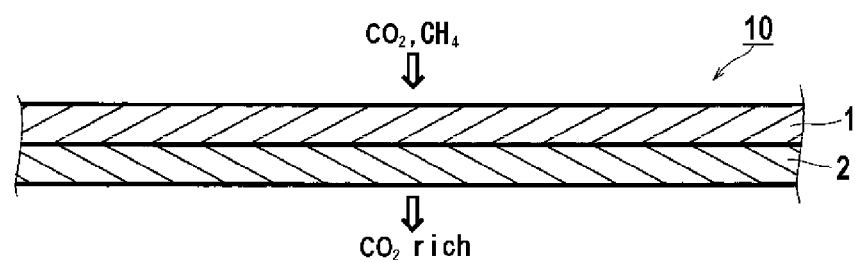
FIG. 1 is a cross-sectional view schematically illustrating one embodiment of the gas separation composite membrane according to the present invention.
Figure 2:
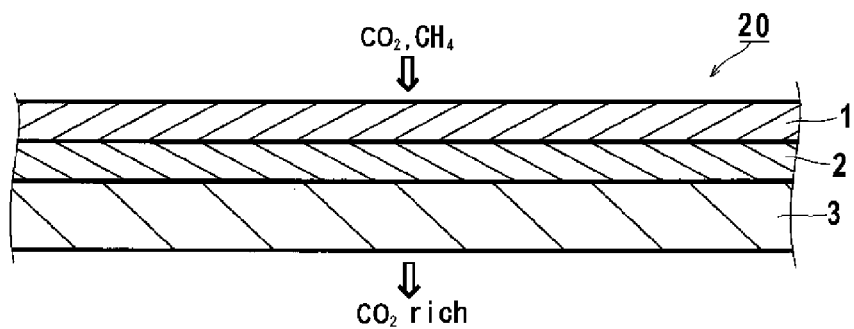
FIG. 2 is a cross-sectional view schematically illustrating another embodiment of the gas separation composite membrane according to the present invention.

The composite membrane according to the present invention has a gas separating layer containing a crosslinked polyimide resin formed over a gas-permeable supporting layer. This composite membrane is preferably formed by coating a coating liquid (dope) to form the above-described gas separating layer ("coating" herein includes an embodiment in which the coating liquid is attached on the surface by dipping) at least on a surface of a porous support, and irradiating the resultant coated surface with active radiation. FIG. 1 is a cross-sectional view schematically showing a gas separation composite membrane 10, being a preferred embodiment according to the present invention. The reference sign 1 is a gas separating layer and the reference sign 2 is a supporting layer constituted of a porous layer. FIG. 2 is a cross-sectional view schematically showing a gas separation composite membrane 20, being a preferred embodiment according to the present invention. According to this embodiment, in addition to the gas separating layer 1 and the porous layer 2, a nonwoven fabric layer 3 is added as the supporting layer.

An expression "over the supporting layer" means that any other layer may be interposed between the supporting layer and the gas separating layer. In addition, unless otherwise noted, with regard to expressions "over" and "under", a direction in which a gas to be separated is supplied is referred to as "over", and a direction from which a separated gas is discharged is referred to "under".

The gas separation composite membrane according to the present invention may have the gas separating layer formed and arranged on the surface or inside of the porous support. The gas separating layer is formed at least on the surface, and thus the composite membrane can be simply realized. Formation of the gas separating layer at least on the surface of the porous support allows realization of a composite membrane having advantages of high separation selectivity, high gas permeability and also mechanical strength. Regarding the membrane thickness of the separating layer, the membrane is preferably as thin as possible under conditions to provide superior gas permeability while maintaining mechanical strength and separation selectivity.

The thickness of the gas separating layer of the gas separation composite membrane according to the present invention is not particularly limited, but is preferably from 0.01 to 5.0 μm, and more preferably from 0.1 to 1.0 μm.

The porous support preferably applied for the supporting layer is not particularly limited so long as it satisfies mechanical strength and high gas permeability, may be a porous membrane made of any organic or inorganic substance and is preferably an organic polymer porous membrane. The thickness thereof is preferably from 1 to 3,000 μm, more preferably from 5 to 500 μm, and further preferably from 5 to 150 μm. Regarding the fine pore structure of this porous membrane, a mean pore diameter is ordinarily 10 μm or less, preferably 0.5 μm or less, and more preferably 0.2 μm or less, and a porosity is preferably from 20% to 90%, and more preferably from 30% to 80%. In addition, the gas permeability is preferably $3\times10^{-5}$ cm$^3$ (STP)/cm·sec·cmHg or more, based on carbon dioxide permeation rate. Examples of the material for the porous membrane include conventionally known polymers, including polyolefin-based resins such as polyethylene and polypropylene; fluorine-containing resins such as polytetrafluoroethylene, polyvinyl fluoride, and polyvinylidene fluoride; and various resins such as polystyrene, cellulose acetate, polyurethane, polyacrylonitrile, polyphenyleneoxide, polysulfone, polyethersulfone, polyimide and polyaramide. Above all, from viewpoints of excellent production competence upon coating the above-described polyimide compound and performing crosslinking, attaining both of high gas permeability and separation selectivity, the supporting layer is preferably constituted of polyacrylonitrile, polysulfone or polyphenylene oxide, and further preferably polyacrylonitrile. The shape of the porous membrane may be any of plate, spiral, tubular or hollow fibers.

In the present invention, application of the supporting layer forming the gas separating layer is to be essentially required. As mentioned above, this supporting layer being a thin and porous raw material is preferred due to capability of securing sufficient gas permeability. Moreover, the supporting layer is preferably in a thin membrane and porous form also for maximizing excellent gas separation selectivity of the gas separating layer as mentioned later. On the one hand, when severe reaction conditions such as a high temperature and long time are imposed on shaping of the gas separation membrane, the conditions may occasionally damage the above-mentioned thin and porous supporting layer not to allow development of sufficient performance as the composite membrane. From such a viewpoint, the gas separation composite membrane using the crosslinkable organic-inorganic hybrid structure employed in the present invention can be formed under mild conditions, produce an excellent effect, and develop high performance in both of production competence and product quality.

In the present invention, in order to further provide the supporting layer with mechanical strength, a support is desirably formed as the supporting layer for forming the gas separating layer. Specific examples of such a support include a woven fabric, a nonwoven fabric and a net, and a nonwoven fabric is preferably used in view of membrane-forming properties and cost. As the nonwoven fabric, fibers formed of polyester, polypropylene, polyacrylonitrile, polyethylene, polyamide or the like may be used alone or in combination with a plurality of fibers. The nonwoven fabric can be produced, for example, by paper-making of main fibers and binder fibers that are uniformly dispersed in water, using a cylinder mold, a fourdrinier or the like, and drying the resultant product by a drier. Moreover, the nonwoven fabric is preferably interposed between two rolls and subjected to pressure-heating processing for the purpose of removing fluff or improving mechanical properties.

The gas separating composite membrane according to the present invention can be preferably used for a gas separation recovery method or a gas separation purification method. For example, the gas separating composite membrane can be processed into a gas separation membrane that can efficiently separate a specific gas from a gaseous mixture containing hydrogen, helium, carbon monoxide, carbon dioxide, hydrogen sulfide, oxygen, nitrogen, ammonia, sulfur oxide, nitrogen oxide, a hydrocarbon such as methane and ethane, an unsaturated hydrocarbon such as propylene, or a gas of a perfluoro compound such as tetrafluoroethane. In particular, the gas separation composite membrane is preferably processed into a gas separation membrane for selectively separating carbon dioxide from a gaseous mixture containing carbon dioxide/hydrocarbon (methane), and is preferably applied to the method of producing the same, and is preferably assembled into a module or a separation apparatus using the same.

Above all, a gas to be supplied is preferably a mixed gas of carbon dioxide and methane, a transmission rate of carbon dioxide at 40° C. and 40 atmospheric pressure is preferably more than 20 GPU, more preferably from 20 to 300 GPU. A ratio of transmission rates ($R_{CO2}/R_{CH4}$) of carbon dioxide and methane is preferably 15 or more, more preferably 20 or more, and particularly preferably from 20 to 50.

From the viewpoint that performances of the gas separation membrane of the present invention is brought out favorably, pressure of gas to be supplied is preferably 10 atmospheric pressure or higher, more preferably 20 atmospheric pressure or higher, still more preferably 30 atmospheric pressure or higher, and particularly preferably 40 atmospheric pressure or higher.

In an actual natural gas, impurities such as long chain hydrocarbons and toluene are contained in addition to methane as a major ingredient. Because a composition or content of these hydrocarbon-based impurity gases varies significantly depending on the producing area, it is difficult to estimate the degree of influence. However, there is concern that such impurity gases cause adverse effects such as plasticization of the membrane, or shielding of free volume of the membrane. From the viewpoint that performance of the gas separation membrane is brought out favorably, gas-separation performance is stable preferably even in the case of 1 vol. % or more, stable more preferably even in the case of 3 vol. % or more, and stable still more preferably even in the case of 5 vol. % or more.

The mechanism of dissolution and diffusion to the membrane is thought to be involved in the above-described selective gas permeation. Study has been made for a separation membrane containing a polyethyleneoxy (PEO) composition by taking an advantage of such a viewpoint (see Journal of Membrane Science, 1999, 160, 87-99). This results from strong interaction of carbon dioxide with the polyethyleneoxy composition. This polyethyleneoxy membrane is a flexible and rubbery polymer membrane having a low glass transition temperature, and therefore a difference of diffusion coefficients depending on gas species is small, and separation selectivity is mainly caused due to an effect of a difference in solubility. On the other hand, according to the present invention, a glass transition temperature of the polyimide compound used therein is high, and while the above-described dissolution and diffusion action is developed, thermal durability of the membrane can also be significantly improved.

The crosslinked organic-inorganic hybrid resin applied in the gas separation layer in the present invention has a structure in which a polymer incorporating therein an oxanthrene unit or a polyimide compound has been crosslinked via a crosslinking chain, and the crosslinking chain contains a site represented by formula (I).
[formula (A)]

The repeating unit represented by formula (A) is described below in detail.

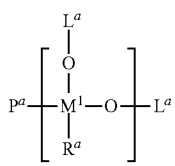

(A)

$R^a$ $R^a$ represents an alkyl group, a cycloalkyl group, an aryl group, an alkoxy group, an aryloxy group, or *—O—**. The symbol "*" means a bonding hand with $M^1$. The symbol "**" means a connection site with an adjacent $M^1$. Preferable examples of the alkyl group, the cycloalkyl group, the aryl group, the alkoxy group, and the aryloxy group include examples of substituent Z described below. Among these, an alkyl group, an alkoxy group and an aryloxy group are particularly preferable. $R^a$ preferably represents an alkyl group, an alkoxy group or *—O—**. When $R^a$ represents an alkoxy group, it means that the group remains as a reaction residue due to a partially unreacted sol-gel reaction. Therefore, it is preferable that the repeating unit continues preferably via *—O—** in order to realize a stable crosslinked structure.

$M^1$ $M^1$ represents a metal atom selected from the group consisting of Si, Ge, Mg, Al, Ti, Zr and Sb; preferably Si, Ge, Mg or Ti; and further preferably Si or Ge. $M_1$ is also desirably combined with heterologous atoms in combination with plural kinds of crosslinking agents described below whereby an organic-inorganic hybrid structure is configured.

$P^a$ $P^a$ represents a structural site of a polyimide compound or a polymer incorporating therein an oxanthrene unit. Preferable embodiments of each resin are explained in detail in the next section.

$L^a$ $L^a$ represents a connection site with an adjacent $M^1$.

To take the case where the metal $M^1$ is Si as an example, with respect to the above-described crosslinked form, the site of formula (A) preferably forms a silsesquioxane bond to constitute a crosslinked network.

Since silicon has 4 bonding hands, the basic constituting unit of polysiloxane is classified by the number of an organic group represented by a methyl group and a phenyl group per one silicon atom, and thus, can be classified into 4 as shown below. In the following formulae, R represents an organic group.

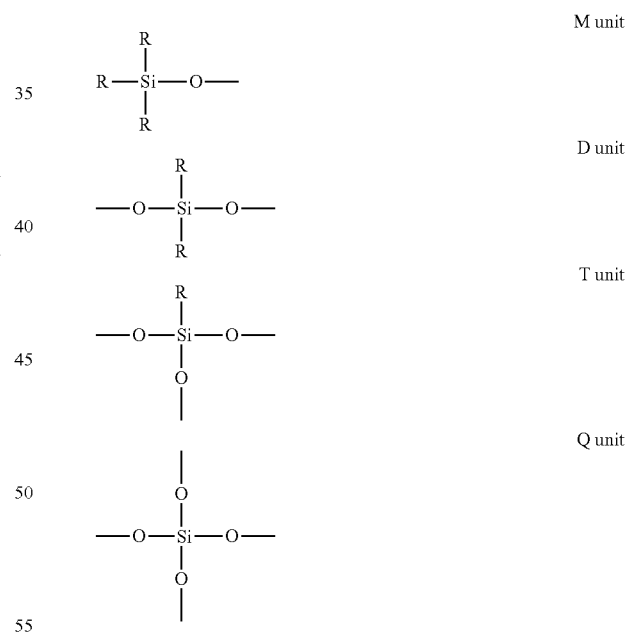

The silsesquioxane means a collective term of the polysiloxane in which its basic constituting unit is the T-unit. The silicon in the silsesquioxane binds to 3 oxygen atoms, and each of the oxygen atoms binds to 2 silicon atoms and therefore its theoretical composition results in $RSiO_{3/2}$ (the Latin word for three-half is SESQUI). In the present invention, R means a bond to the above-described Pa in the formula of the above-described T-unit. Three bonding hands may bind to an adjacent $M^1$ (Si), or may bind to other constituent elements. That is, as described above, a —Si—O—Si—bond is not constituted due to the presence of a partially unreacted portion, and $R^a$ may be another group other than the group defined by $R^a$ as Si—$R^a$ described above.

[Polyimide Compound Structural Part]

The site having a structure of the polyimide compound in the above-described Pa is preferably a polyimide compound containing a repeating unit represented by formula (I) and a repeating unit represented by formula (III-a) or formula (III-b). The structure of the polyimide compound may further contain a repeating unit represented by formula (II-a) or (II-b), if necessary. Here, each repeating unit means that at least one kind of repeating unit is needed to be contained and a plurality of the same kind of repeating units may be contained.

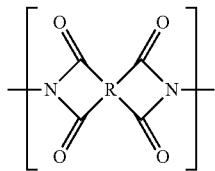
(I)

In formula (I), R is a structural part containing at least one hydrocarbon ring having 4 to 12 carbon atoms. R is preferably a group of atoms selected from the group consisting of the groups represented by any one of formulas (I-a), (I-b), (I-c), (I-d), (I-e), (I-f) and (I-g). This mother nucleus (R) is preferably represented by formula (I-a), (I-b) or (I-c), more preferably formula (I-a) or (I-c), and particularly preferably formula (I-a).

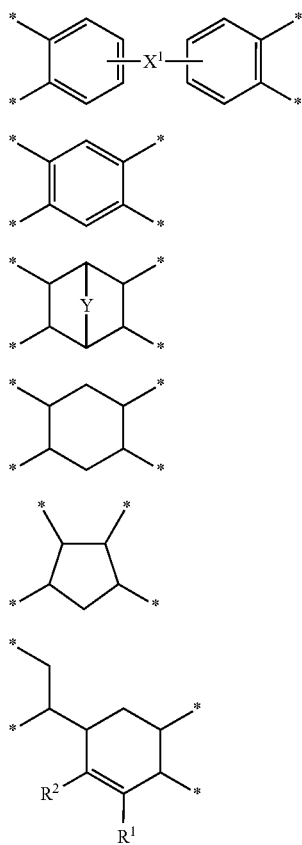

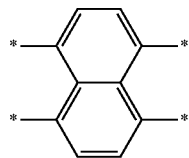
(I-g)

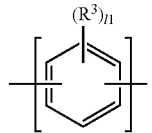
(II-a)

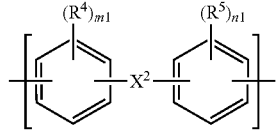
(II-b)

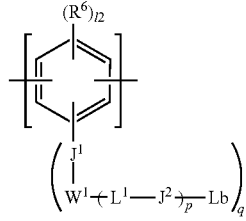
(III-a)

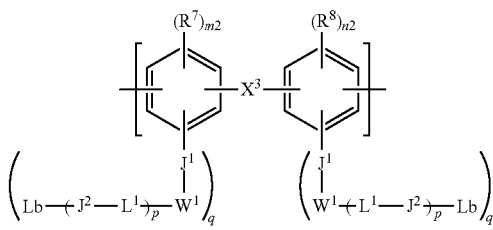
(III-b)

$X^1$, $X^2$ and $X^3$ $X^1$, $X^2$ and $X^3$ each independently represent a single bond or a divalent linking group. The divalent linking group is preferably *—$CR^F_2$—* ($R^F$ represents a hydrogen atom or a substituent; and when $R^F$ is a substituent, two $R^F$'s may bond with each other to form a condensed ring), *—O—*, *—$SO_2$—*, *—CO—*, or *—S—*; more preferably *—$CR^F_2$—*, *—O—*, *—$SO_2$—*, or *—CO—*. The symbol "*" represents a binding site with the phenylene group. When $R^F$ represents a substituent, specific examples thereof include the substituent Z described below. Among them, a halogenated alkyl group is preferable, a fluorinated alkyl group is more preferable, and a trifluoromethyl group is particularly preferable. Moreover, when an expression "may bond with each other to form a ring" is referred to herein, the expression may include ones that are bonded by a single bond, a double bond or the like to form cyclic structure, or ones that are subjected to ring condensation to form condensed ring structure.

Y

Y represents a methylene group or a vinylene group, preferably a vinylene group.

$R^1$ and $R^2$ $R^1$ and $R^2$ each independently represent a hydrogen atom or a substituent. As the substituent, any one selected from the below-mentioned substituent group Z can be each independently applied. On referring to the substituent herein, unless otherwise noted, the below-mentioned substituent Z is applied as a preferred range. $R^1$ and $R^2$ may bond with each other to form a ring.

$R^1$ and $R^2$ are preferably a hydrogen atom or an alkyl group; more preferably a hydrogen atom, a methyl group or an ethyl group; and further preferably a hydrogen atom.

$R^3$, $R^4$ and $R^5$ $R^3$, $R^4$ and $R^5$ each independently represent a substituent; preferably an alkyl group, a hydroxyl group, a carboxyl group, a sulfonic acid group, an amino group, a mercapto group, an amide group (carbamoyl group), an alkoxy group, a sufonyl group-containing group (an alkylsufonyl group and the like), or a halogen atom. Preferred examples of these substituents are the same as those defined as the substituent Z. Subscripts l1, m1 and n1 representing the number of substituents described above are an integer from 0 to 4, preferably from 1 to 4, and more preferably 3 or 4.

When $R^3$, $R^4$, $R^5$ are a plurality of alkyl groups, $R^3$, $R^4$ and $R^5$ may bond with each other to form a ring.

$R^6$, $R^7$ and $R^8$ $R^6$, $R^7$ and $R^8$ each independently represent a substituent. Preferred examples of these substituents are the same as those defined as the substituent Z. Subscripts l2, m2 and n2 representing the number of the substituents are an integer from 0 to 3, preferably from 1 to 4, and more preferably 2 to 3.

$J^1$ and $J^2$ $J^1$ and $J^2$ represent a single bond or a divalent linking group. Specifically, the linking group is *—O—**, *—S—**, *—CO—**, *—C(=O)O—**, *—CONR$^{J1}$—**, *—OC(=O)—**, *—COO$^-$N$^+$R$^{J2}$R$^{J3}$R$^{J4}$—**, *—SO$_3^-$N$^+$R$^{J5}$R$^{J6}$R$^{J7}$—**, a methylene group, a phenylene group, or *—C$_6$H$_5$CO—**. Here, the symbol "*" represents a bonding hand on the side of $L^1$ for $J^2$ and on the side of the phenylene group for $J^1$, and the symbol "**" represents a bonding hand reverse thereto. $R^{J1}$ to $R^{J7}$ each represent a hydrogen atom, an alkyl group, an aryl group, or an aralkyl group. Among these, $J^1$ and $J^2$ represent preferably *—CO—**, *—COO—**, *—CONR$^{J1}$—**, *—COO—**, a methylene group, a phenylene group, or *—C$_6$H$_4$CO—**. Preferred range of $R^{J1}$ to $R^{J7}$ are the same as those explained as the alkyl group or the aryl group in the substituent group Z. Among these, $J^1$ and $J^2$ are preferably *—CO—**, *—COO—**, or *—COO—**; and particularly preferably *—COO—**.

$W^1$ $W^1$ represents a single bond or a divalent linking group. Examples of the divalent linking group include linear, branched or cyclic alkylene groups (preferably alkylene groups having 1 to 30 carbon atoms, more preferably alkylene groups having 1 to 12 carbon atoms, further preferably alkylene groups having 1 to 4 carbon atoms, examples thereof include methylene, ethylene, propylene, butylene, pentylene, hexylene, octylene, decylene and the like), alkyleneoxy groups (preferably alkyleneoxy groups having 1 to 30 carbon atoms, more preferably alkyleneoxy groups having 1 to 12 carbon atoms, further preferably alkyleneoxy groups having 1 to 4 carbon atoms, and examples thereof include methyleneoxy, ethyleneoxy, propyleneoxy, butyleneoxy, pentyleneoxy, hexyleneoxy, octyleneoxy, decyleneoxy and the like), aralkylene groups (preferably aralkylene groups having 7 to 30 carbon atoms, more preferably aralkylene groups having 7 to 13 carbon atoms, and examples thereof include benzylidene, cinnamylidene and the like), arylene groups (preferably arylene groups having 6 to 30 carbon atoms, more preferably arylene groups having 6 to 15 carbon atoms, and examples thereof include phenylene, cumenylene, mesitylene, tolylene, xylylene and the like) and the like. These may further have a substituent. As the further substituent, a hydroxy group or a halogen atom is preferred, a hydroxy group or a fluorine atom is more preferred, and a fluorine atom is particularly preferred. In addition, a compound having an ether bond in the molecule is preferred.

$L^1$ $L^1$ represents a divalent linking group. Specific examples thereof include a linking group composed of a repeating unit represented by any one of (L-1) to (L-35) described below or a combination thereof. Herein, the symbol "*" of the following linking group is a bonding hand on the side of $W^1$, and the symbol "**" is a bonding hand on the side of $J^2$.

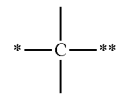
(L-1)

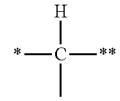
(L-2)

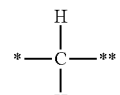
(L-3)

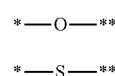
(L-4)

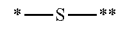
(L-5)

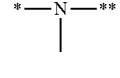
(L-6)

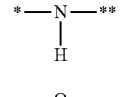
(L-7)

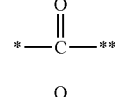
(L-8)

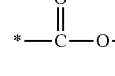
(L-9)

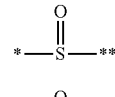
(L-10)

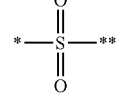
(L-11)

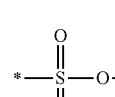
(L-12)

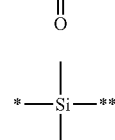
(L-13)

(L-14) 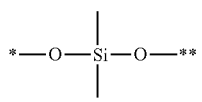

(L-15) 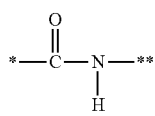

(L-16) 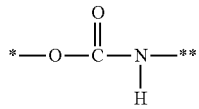

(L-17) 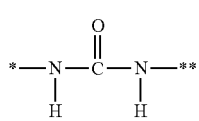

(L-18) 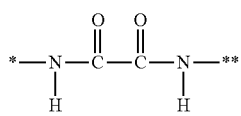

(L-19) 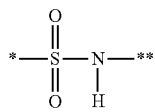

(L-20) 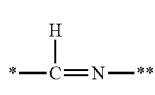

(L-21) 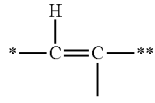

(L-22) 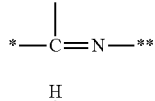

(L-23) 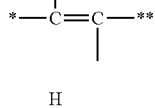

(L-24) 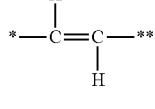

(L-25) 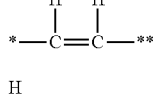

(L-26) 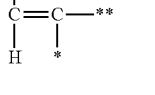

(L-27) *—C≡C—**

(L-28) 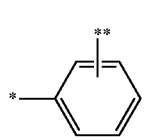

(L-29) 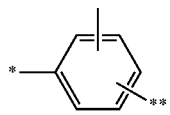

(L-30) 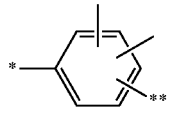

(L-31) 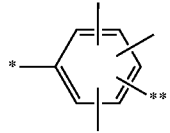

(L-32) 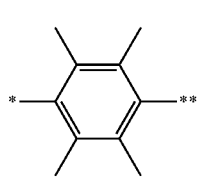

(L-33) 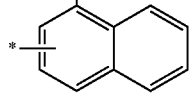

(L-34) 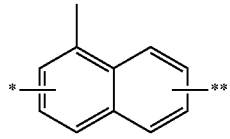

(L-35) 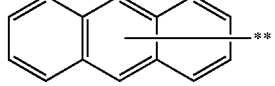

$L^1$ is preferably any one of formulas (L-1) to (L-35), an alkylene group, an alkyleneoxy group or an arylene group; and more preferably an alkylene group or an alkyleneoxy group.

p p represents an integer of 0 or more, preferably an integer of from 0 to 10, and more preferably an integer of from 0 to 5.

q q represents an integer of 1 or more and 4 or less.

Lb

Lb means a connection site with $M^1$ in the above-described formula (A).

[Polymer Structural Part Incorporating Therein Oxanthrene Unit]

The above-described polymer structural part incorporating therein oxanthrene unit preferably has a skeleton of the resin with inherent microporosity (PIM: Polymer of Intrinsic Microporosity); and more preferably contains a repeating unit represented by formula (IV-a), and a repeating unit represented by formula (IV-b). Here, each repeating unit means that at least one kind of repeating unit is needed to be contained and a plurality of the same kinds of repeating unit may be contained.

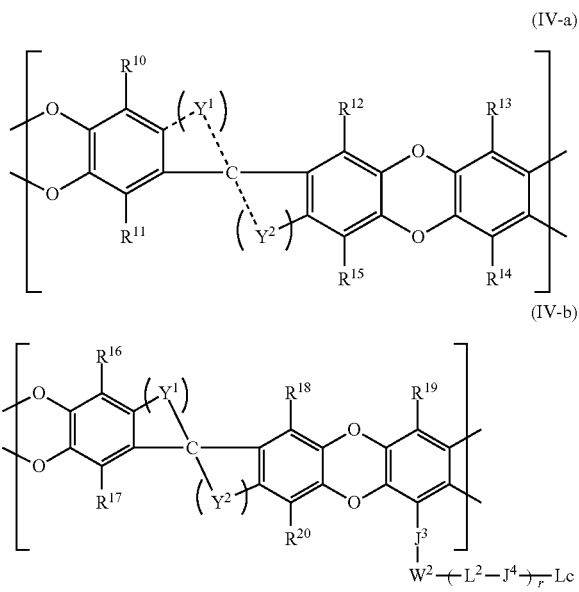

(IV-a)

(IV-b)

$R^{10}$ to $R^{20}$

In formulas (IV-a) and (IV-b), $R^{10}$ to $R^{20}$ each independently represent a hydrogen atom or a substituent. As the substituent, it is possible to use each independently any one selected from the Substituent Group Z described below. Among these, a hydrogen atom, an alkyl group, a cyano group, a halogen atom, a heterocyclic group and a carboxyl group are preferable; and a hydrogen atom, a cyano group and a carboxyl group are more preferable.

$J^3$, $J^4$ and $W^2$ $J^3$, $J^4$ and $W^2$ represent a single bond or a divalent linking group. Preferred ranges thereof are the same as those of $J^1$, $J^2$ and $W^1$, respectively.

$L^2$ $L^2$ represents a divalent linking group. A preferred range thereof is the same as that of $L^1$ described above.

r r represents an integer of 0 or more. When r is 2 or more, a plurality of $L^2$'s and $J^4$'s may be the same or different from each other.

$Y^1$ and $Y^2$ $Y^1$ and $Y^2$ represent a group of atoms for forming a ring with the carbon atom and the benzene ring. The group of atoms comprised of a carbon atom, an oxygen atom, a hydrogen atom and/or a nitrogen atom is preferable, and the group of atoms comprised of a carbon atom, a hydrogen atom and/or an oxygen atom is more preferable. The group of atoms is still more preferably an alkylene group having 1 to 4 carbon atoms, or an alkyleneoxy group having 1 to 4 carbon atoms. When $Y^1$ and $Y^2$ form a ring, the ring may have a substituent, and the substituent is selected from the Substituent Group Z described below. Among these, it is preferable that an alkyl group is substituted.

Lc

Lc means a connection site with $M^1$ in the above-described formula (A).

[Production Method]

It is preferable that the crosslinked organic-inorganic hybrid membrane of the present invention is formed by coating a coating liquid containing a polyimide compound or a polymer incorporating therein an oxanthrene unit, and a crosslinking agent having the following metal atom $M^1$ (preferably a crosslinking agent represented by the following formula (B)) over the above-described supporting layer, and irradiating an active radiation, or applying heat onto the coating liquid thereby inducing a crosslinking reaction.

(B)

$A^2$

In formula (B), $A^2$ represents a reactive group; $A^2$ preferably represents a hydroxy group, an alkenyl group, an alkynyl group, an amino group, a cyano group, an alkoxy group, an isocyanate group or a mercapto group; more preferably an alkenyl group, an alkoxy group, an amino group or a mercapto group. Preferable examples of the alkenyl group and the alkynyl group include examples of the substituent Z described below. Of the alkenyl group, a vinyl group is particularly preferable.

In the present invention, the compound represented by the following formula (O-1), (O-2) or (O-3) is particularly preferably used as the crosslinking agent.

$$H_2N-L^O-Si(R^O)_3 \qquad \text{O-1}$$

$$HS-L^O-Si(R^O)_3 \qquad \text{O-2}$$

$$CH_2=CH-L^O-Si(R^O)_3 \qquad \text{O-3}$$

In formulas (O-1), (O-2) and (O-3), $L^O$ represents a single bond or a linking group. As the linking group, preferred are an alkylene group having 1 to 10 carbon atoms (more preferably 1 to 6 carbon atoms, still more preferably 1 to 3 carbon atoms), an alkenylene group having 2 to 10 carbon atoms (more preferably 2 to 6 carbon atoms, still more preferably 2 to 4 carbon atoms), an arylene group having 6 to 22 carbon atoms (more preferably 6 to 10 carbon atoms), a carbonyl group, an ether group (—O—), a thioether group (—S—), an imino group (—$NR^N$— wherein $R^N$ is an alkyl group having 1 to 6 carbon atoms, more preferably 1 to 3 carbon atoms), or a linking group comprised of a combination of these groups. Specific examples of the linking group include a single bond, an alkylene group having the above-described carbon atoms, an alkenylene group having the above-described carbon atoms, a carbonyl group, an oxycarbonyl group, a carbonyloxy group, a carbonate group, an amide group, a urethane group, an (oligo) alkyleneoxy group having 1 to 20 carbon atoms (—(Lr—O—)x- wherein x is an integer of 1 or more and Lr is an alkylene group. The same shall apply hereafter), a carbonyl (oligo) oxyalkylene group having 2 to 20 carbon atoms (—CO—(O—Lr)x-), a carbonyloxy (oligo) alkyleneoxy group having 2 to 20 carbon atoms (—COO—(Lr—O—)x-), an (oligo) alkyleneimino group having 1 to 20 carbon atoms (—(Lr—$NR^N$-)x), an alkylene (oligo) iminoalkylene group having 2 to 20 carbon atoms (—Lr—($NR^N$—Lr-)x-), and a carbonyl (oligo) iminoalkylene group having 2 to 20 carbon atoms (—CO—($NR^N$—Lr-)x-). Among these, as preferable examples, an alkylene group having the above-described carbon atoms, an alkenylene group having the above-described carbon atoms, an (oligo) alkyleneoxy group having the above-described carbon atoms, a carbonyl (oligo) oxyalkylene group having the above-described carbon atoms, a carbonyloxy (oligo) alkyleneoxy group having the above-described carbon atoms, an alkylene (oligo) iminoalkylene group having the above-described carbon atoms, and a carbonyl (oligo) iminoalkylene group having the above-described carbon atoms are preferred. Lr is preferably an alkylene group having 1 to 6 carbon atoms, and more preferably an alkylene group having 1 to 3 carbon atoms. A plurality of Lr, $R^N$, x, or the like do not have to be identical to each other.

$R^O$ represents an alkyl group (carbon number of 1 to 12 is preferable, carbon number of 1 to 6 is more preferable, and carbon number of 1 to 3 is particularly preferable), an aryl group (carbon number of 6 to 22 is preferable, and carbon number of 6 to 14 is more preferable), an alkoxy group (carbon number of 1 to 12 is preferable, carbon number of 1 to 6 is more preferable, and carbon number of 1 to 3 is particularly preferable), or an aryloxy group (carbon number of 6 to 22 is preferable, and carbon number of 6 to 14 is more preferable).

$L^3$ $L^3$ represents a single bond or a divalent linking group. Specific examples of the linking group include a repeating unit represented by any one of (L-1) to (L-35) described above or a linking group composed of a combination thereof.

$R^{21}$, $R^{22}$ and $R^{23}$ $R^{21}$, $R^{22}$ and $R^{23}$ represent an alkyl group, a cycloalkyl group, an aryl group, an alkoxy group, or an aryloxy group. $R^{21}$, $R^{22}$ and $R^{23}$ are more preferably an alkoxy group. Preferable examples of the alkyl group, the cycloalkyl group, the aryl group, the alkoxy group, and the aryloxy group include examples of substituent Z described below. Among these, an alkyl group, an alkoxy group, an aryloxy group and the like are particularly preferable. In addition, 2 or more of the above-described $R^{21}$ to $R^{23}$ and $A^2$ may bind to one another to form a ring.

$M^1$ $M^1$ has the same meaning as $M^1$ in the above-described formula (A).

(Polyimide Compound)

The polyimide compound is preferably a polymer containing a repeating unit represented by formula (I), and a repeating unit represented by formula (VI-a) or (VI-b). The polyimide compound may further contain a repeating unit represented by formula (II-a) or (II-b).

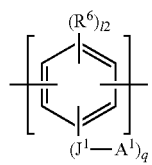

(VI-a)

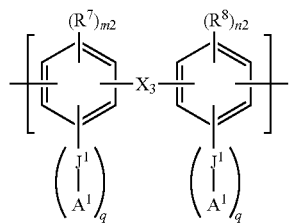

(VI-b)

In formulas (VI-a) and (VI-b), $A^1$ represents a reactive group; preferably a hydroxy group, a carboxyl group, a sulfonic acid group, an alkenyl group, an alkoxy group, an alkynyl group, or a mercapto group; more preferably a hydroxy group, a carboxyl group, an alkynyl group, or a mercapto group; further preferably a carboxyl group, an alkenyl group, or a mercapto group; and particularly preferably a carboxyl group or a mercapto group.

$R^6$, $R^7$, $R^8$, $J^1$, l2, m2, n2, $X^3$ and q each have the same meaning as those in formula (III-a) or (III-b), respectively, and preferable ranges are also the same.

The polyimide can be synthesized by condensation polymerization of an acid anhydride with a diamine. As the synthetic method, a method described in a general book (for example, Saishin Polyimide-Kiso to Oyo-, pp. 3-49, edited by Yoshio Imai and Rikio Yokota, issued by NTS Publishing Co., Ltd.) can be appropriately selected. Specific examples of general acid anhydride that can be used in the present invention are shown below.

(Polymer Incorporating Therein an Oxanthrene Unit)

The above-described polymer incorporating therein an oxanthrene unit is preferably a polymer compound having at least one kind of repeating unit represented by formula (V). The polymer may further contain a repeating unit represented by formula (IV-a).

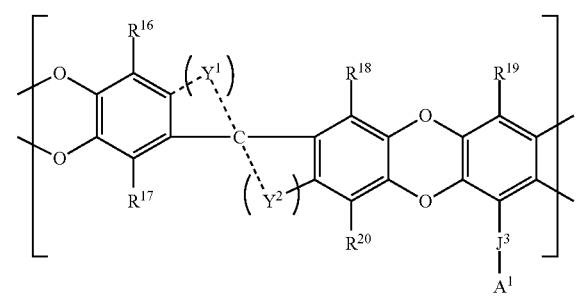

In formula (V), $R^{16}$ to $R^{20}$, $Y^1$, $Y^2$ and $J^3$ each have the same meaning as those in formula (IV-b), respectively, and preferable ranges are also the same.

$A^1$ has the same meaning as $A^1$ in formula (VI-a) or (VI-b), and a preferable range is also the same.

According to a preferable embodiment of the above-described production method of the present invention, it is possible to obtain an arbitrary organic-inorganic hybrid structure, composition ratio and crosslink density by selecting a suitable polymer and yet selecting and adding a suitable inorganic alkoxide compound. Generally, in the gas separation membrane, due to reduction of a free volume space upon crosslink, gas permeability reduces remarkably. According to the present embodiment, however, the rate of reduction is lower in the organic-inorganic hybrid membrane crosslinked in accordance with a sol-gel method, when compared to other crosslinking methods. Further, even though an inorganic alkoxide is increased, separation selectivity is improved while suppressing the rate of decrease in gas permeability. As a result of analysis by X-ray crystal diffractometry, it has already been found that regularity at the low angle side is increased by increasing the addition amount of the inorganic alkoxide, and therefore it is assumed that this action allows suppression or improvement in rate of decrease in gas permeability. As for the linking group, a more rigid crosslinked membrane is obtained by an acid-base interaction with a polymer having a carboxyl group, or by an ene/thiol reaction with a polymer having a thiol group. An organic-inorganic hybrid structural gas separation membrane can be obtained at low temperature by allowing easy solubilization in an organic solvent exerting a high film-forming competence and also by allowing induction of a sol-gel reaction by irradiation of an active radiation in coexistence with a photo-radical-acid-generating agent.

In the present specification, when the name of a chemical is called by putting the term "compound" or "resin" at the foot of the chemical name, or when the chemical is shown by a specific name or a chemical formula, a showing of the compound is used to mean not only the compound itself, but also a salt, or ion thereof and the like. Further, the showing of the compound is also used to mean incorporation of derivatives having a predefined substituent or modified by a predefined configuration to an extent necessary to obtain a desired effect. Further, in the present specification, when a specific group of atoms or a specific compound is called by putting the term "group" at the foot of the specific group of atoms or the specific compound with respect to the substituent, the group means that the group of atoms or the compound may have further an arbitrary substituent.

Substituent Group Z includes:

an alkyl group (preferably an alkyl group having 1 to 30 carbon atoms, more preferably an alkyl group having 1 to 20 carbon atoms, particularly preferably an alkyl group having 1 to 10 carbon atoms, and examples thereof include methyl, ethyl, iso-propyl, tert-butyl, n-octyl, n-decyl, and n-hexadecyl), a cycloalkyl group (preferably a cycloalkyl group having 3 to 30 carbon atoms, more preferably a cycloalkyl group having 3 to 20 carbon atoms, particularly preferably a cycloalkyl group having 3 to 10 carbon atoms, and examples thereof include cyclopropyl, cyclopentyl, cyclohexyl and the like), an alkenyl group (preferably an alkenyl group having 2 to 30 carbon atoms, more preferably an alkenyl group having 2 to 20 carbon atoms, particularly preferably an alkenyl group having 2 to 10 carbon atoms, and examples thereof include vinyl, allyl, 2-butenyl, 3-pentenyl and the like), an alkynyl group (preferably an alkynyl group having 2 to 30 carbon atoms, more preferably an alkynyl group having 2 to 20 carbon atoms, particularly preferably an alkynyl group having 2 to 10 carbon atoms, and examples thereof include propargyl, 3-pentynyl and the like), an aryl group (preferably an aryl group having 6 to 30 carbon atoms, more preferably an aryl group having 6 to 20 carbon atoms, particularly preferably an aryl group having 6 to 12 carbon atoms, and examples thereof include phenyl, p-methylphenyl, naphthyl, anthranyl and the like), an amino group (preferably an amino group having 0 to 30 carbon atoms, more preferably an amino group having 0 to 20 carbon atoms, particularly preferably an amino group having 0 to 10 carbon atoms, and examples thereof include amino, methylamino, dimethylamino, diethylamino, dibenzylamino, diphenylamino, ditolylamino and the like), an alkoxy group (preferably an alkoxy group having 1 to 30 carbon atoms, more preferably an alkoxy group having 1 to 20 carbon atoms, particularly preferably an alkoxy group having 1 to 10 carbon atoms, and examples thereof include methoxy, ethoxy, butoxy, 2-ethylhexyloxy and the like), an aryloxy group (preferably an aryloxy group having 6 to 30 carbon atoms, more preferably an aryloxy group having 6 to 20 carbon atoms, particularly preferably an aryloxy group having 6 to 12 carbon atoms, and examples thereof include phenyloxy, 1-naphthyloxy, 2-naphthyloxy and the like), a heterocyclic oxy group (preferably a heterocyclic oxy group having 1 to 30 carbon atoms, more preferably a heterocyclic oxy group having 1 to 20 carbon atoms, particularly preferably a heterocyclic oxy group having 1 to 12 carbon atoms, and examples thereof include pyridyloxy, pyrazyloxy, pyrimidyloxy, quinolyloxy and the like), an acyl group (preferably an acyl group having 1 to 30 carbon atoms, more preferably an acyl group having 1 to 20 carbon atoms, particularly preferably an acyl group having 1 to 12 carbon atoms, and examples thereof include acetyl, benzoyl, formyl, pivaloyl and the like), an alkoxycarbonyl group (preferably an alkoxycarbonyl group having 2 to 30 carbon atoms, more preferably an alkoxycarbonyl group having 2 to 20 carbon atoms, particularly preferably an alkoxycarbonyl group having 2 to 12 carbon atoms, and examples thereof include methoxycarbonyl, ethoxycarbonyl and the like), an aryloxycarbonyl group (preferably an aryloxycarbonyl group having 7 to 30 carbon atoms, more preferably an aryloxycarbonyl group having 7 to 20 carbon atoms, particularly preferably an aryloxycarbonyl group having 7 to 12 carbon atoms, and examples thereof include phenyloxycarbonyl and the like), an acyloxy group (preferably an acyloxy group having 2 to 30 carbon atoms, more preferably an acyloxy group having 2 to 20 carbon atoms, particularly preferably an acyloxy group having 2 to 10 carbon atoms, and examples thereof include acetoxy, benzoyloxy and the like), an acylamino group (preferably an acylamino group having 2 to 30 carbon atoms, more preferably an acylamino group having 2 to 20 carbon atoms, particularly preferably an acylamino group having 2 to 10 carbon atoms, and examples thereof include acetylamino, benzoylamino and the like), an alkoxycarbonylamino group (preferably an alkoxycarbonylamino group having 2 to 30 carbon atoms, more preferably an alkoxycarbonylamino group having 2 to 20 carbon atoms, particularly preferably an alkoxycarbonylamino group having 2 to 12 carbon atoms, and examples thereof include methoxycarbonylamino and the like), an aryloxycarbonylamino group (preferably an aryloxycarbonylamino group having 7 to 30 carbon atoms, more preferably an aryloxycarbonylamino group having 7 to 20 carbon atoms, particularly preferably an aryloxycarbonylamino group having 7 to 12 carbon atoms, and examples thereof include phenyloxycarbonylamino and the like), a sulfonylamino group (preferably a sulfonylamino group having 1 to 30 carbon atoms, more preferably a sulfonylamino group having 1 to 20 carbon atoms, particularly preferably a sulfonylamino group having 1 to 12 carbon atoms, and examples thereof include methanesulfonylamino, benzenesulfonylamino and the like), a sulfamoyl group (preferably a sulfamoyl group having 0 to 30 carbon atoms, more preferably a sulfamoyl group having 0 to 20 carbon atoms, particularly preferably a sulfamoyl group having 0 to 12 carbon atoms, and examples thereof include sulfamoyl, methylsulfamoyl, dimethylsulfamoyl, phenylsulfamoyl and the like), a carbamoyl group (preferably a carbamoyl group having 1 to 30 carbon atoms, more preferably a carbamoyl group having 1 to 20 carbon atoms, particularly preferably a carbamoyl group having 1 to 12 carbon atoms, and examples thereof include carbamoyl, methylcarbamoyl, diethylcarbamoyl, phenylcarbamoyl and the like), an alkylthio group (preferably an alkylthio group having 1 to 30 carbon atoms, more preferably an alkylthio group having 1 to 20 carbon atoms, particularly preferably an alkylthio group having 1 to 12 carbon atoms, and examples thereof include methylthio, ethylthio and the like), an arylthio group (preferably an arylthio group having 6 to 30 carbon atoms, more preferably an arylthio group having 6 to 20 carbon atoms, particularly preferably an arylthio group having 6 to 12 carbon atoms, and examples thereof include phenylthio and the like), a heterocyclic thio group (preferably a heterocyclic thio group having 1 to 30 carbon atoms, more preferably a heterocyclic thio group having 1 to 20 carbon atoms, particularly preferably a heterocyclic thio group having 1 to 12 carbon atoms, and examples thereof include pyridylthio, 2-benzimizolylthio, 2-benzoxazolylthio, 2-benzthiazolylthio and the like),
a sulfonyl group (preferably a sulfonyl group having 1 to 30 carbon atoms, more preferably a sulfonyl group having 1 to 20 carbon atoms, particularly preferably a sulfonyl group having 1 to 12 carbon atoms, and examples thereof include mesyl, tosyl and the like), a sulfinyl group (preferably a sulfinyl group having 1 to 30 carbon atoms, more preferably a sulfinyl group having 1 to 20 carbon atoms, particularly preferably a sulfinyl group having 1 to 12 carbon atoms, and examples thereof include methanesulfinyl, benzenesulfinyl and the like), a ureido group (preferably a ureido group having 1 to 30 carbon atoms, more preferably a ureido group having 1 to 20 carbon atoms, particularly preferably a ureido group having 1 to 12 carbon atoms, and examples thereof include ureido, methylureido, phenylureido and the like), a phosphoric acid amide group (preferably a phosphoric acid amide group having 1 to 30 carbon atoms, more preferably a phosphoric acid amide group having 1 to 20 carbon atoms, particularly preferably a phosphoric acid amide group having 1 to 12 carbon atoms, and examples thereof include diethylphosphoric acid amide, phenylphosphoric acid amide and the like), a hydroxyl group, a mercapto group, a halogen atom (for example, a fluorine atom, a chlorine atom, a bromine atom and an iodine atom, more preferably a fluorine atom),
a cyano group, a sulfo group, a carboxyl group, an oxo group, a nitro group, a hydroxamic acid group, a sulfino group, a hydrazino group, an imino group, a heterocyclic group (preferably a heterocyclic group having 1 to 30 carbon atoms, more preferably a heterocyclic group having 1 to 12 carbon atoms, examples of a hetero atom constituting the heterocyclic group include a nitrogen atom, an oxygen atom and a sulfur atom, and specifically examples of the heterocyclic group include imidazolyl, pyridyl, quinolyl, furyl, thienyl, piperidyl, morpholino, benzoxazolyl, benzimidazolyl, benzthiazolyl, a carbazolyl group, an azepinyl group and the like), a silyl group (preferably a silyl group having 3 to 40 carbon atoms, more preferably a silyl group having 3 to 30 carbon atoms, particularly preferably a silyl group having 3 to 24 carbon atoms, and examples thereof include trimethylsilyl, triphenylsilyl and the like), a silyloxy group (preferably a silyloxy group having 3 to 40 carbon atoms, more preferably a silyloxy group having 3 to 30 carbon atoms, particularly preferably a silyloxy group having 3 to 24 carbon atoms, and examples thereof include trimethylsilyloxy, triphenylsilyloxy and the like) and the like. These substituents may be further substituted by one or more substituents selected from the substituent group Z.

Herein, in the present invention, when one structural site has a plurality of substituents, those substituents may be linked with each other to form a ring, or may be subjected to ring condensation partially or wholly with the above-described structural site to form an aromatic ring or an unsaturated heterocycle.

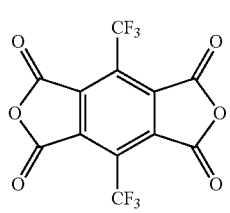

Anhydride-1

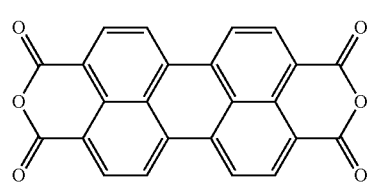

Anhydride-2

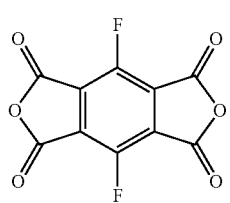

Anhydride-3

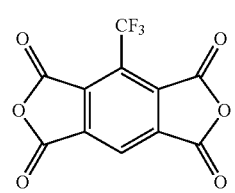

Anhydride-4

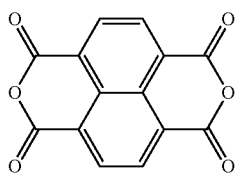

Anhydride-5

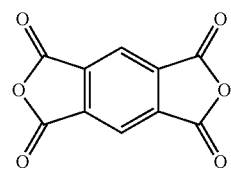

Anhydride-6

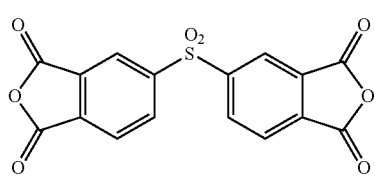

Anhydride-7

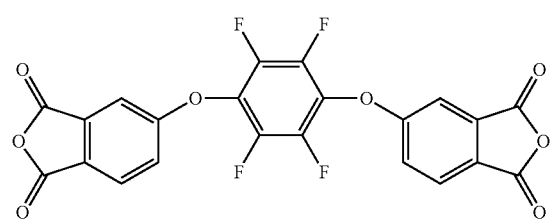

Anhydride-8

-continued
Anhydride-9
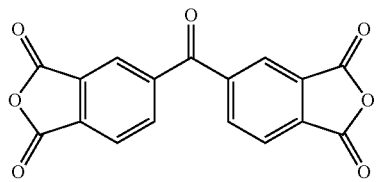
Anhydride-10
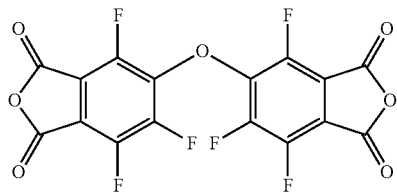
Anhydride-11
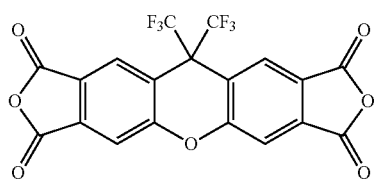
Anhydride-12
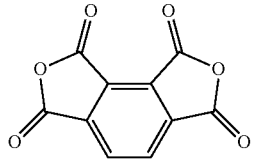
Anhydride-13
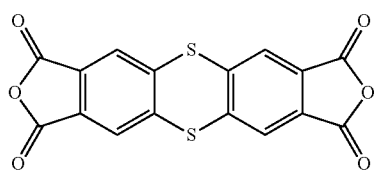
Anhydride-14
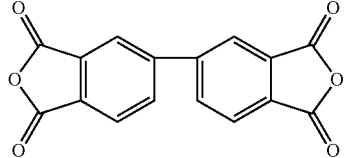
Anhydride-15
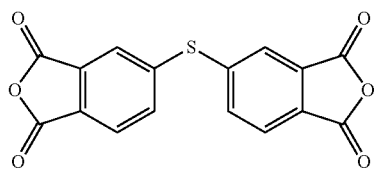
Anhydride-16
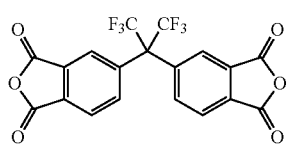
Anhydride-17
Anhydride-18
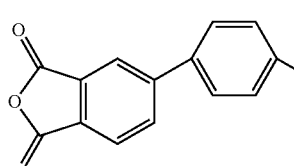
Anhydride-19
Anhydride-20
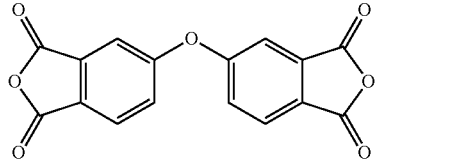
Anhydride-21
Anhydride-22
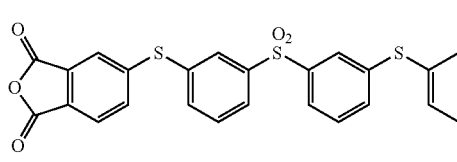
Anhydride-23
Anhydride-24
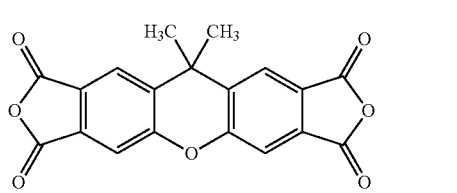

-continued
Anhydride-25
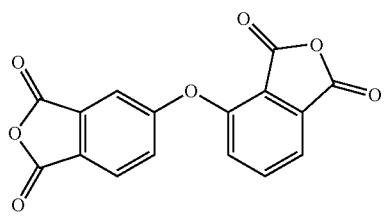
Anhydride-26
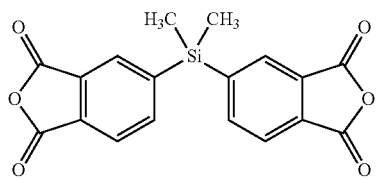
Anhydride-27
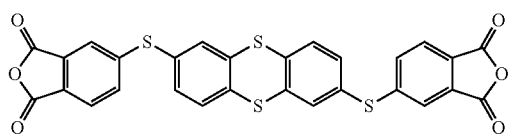
Anhydride-28
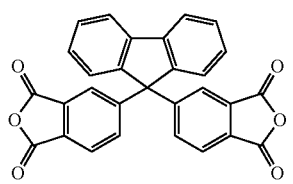
Anhydride-29
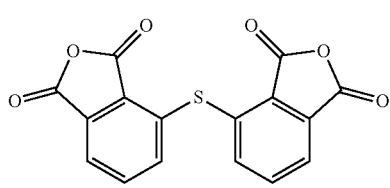
Anhydride-30
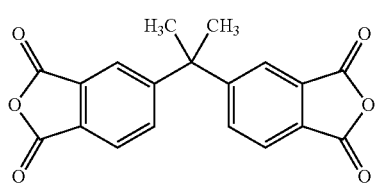
Anhydride-31
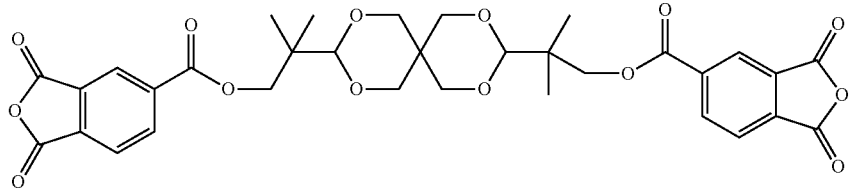
Anhydride-32
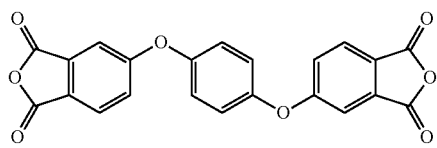
Anhydride-33
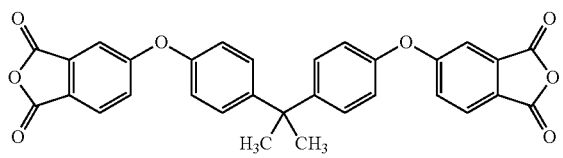
Anhydride-34
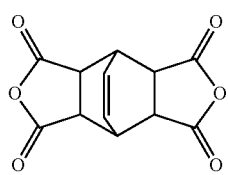
Anhydride-35
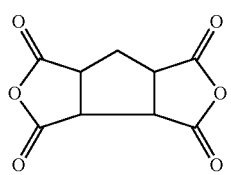
Anhydride-36
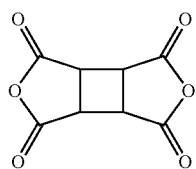
Anhydride-37
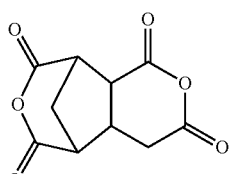
Anhydride-38
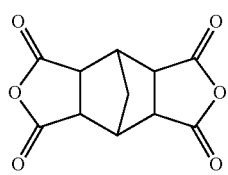
Anhydride-39
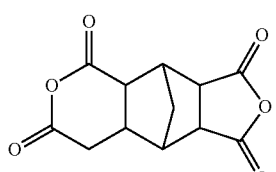

Anhydride-40
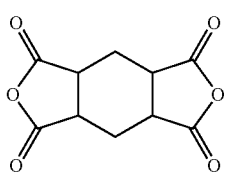
Further, specific examples of general diamine are shown below.
Diamine-1
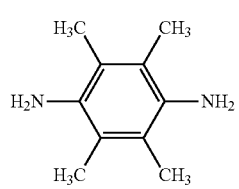
Diamine-2
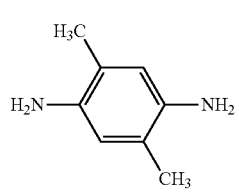
Diamine-3
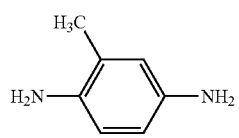
Diamine-4
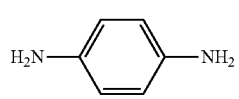
Diamine-5
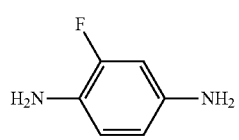
Diamine-6
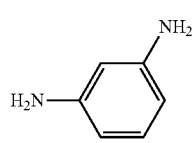
Diamine-7
Diamine-8
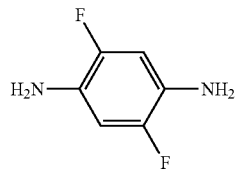
-continued
Diamine-9
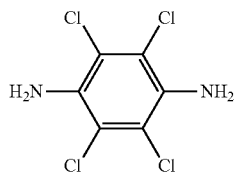
Diamine-10
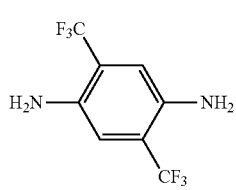
Diamine-11
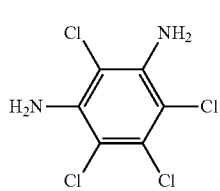
Diamine-12
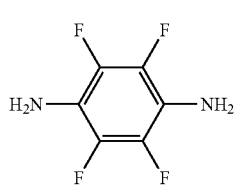
Diamine-13
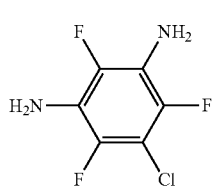
Diamine-14
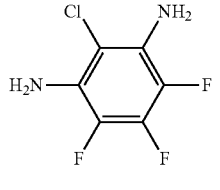
Diamine-15
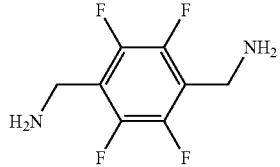

-continued
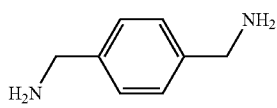
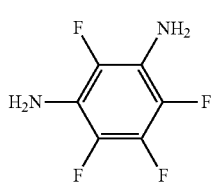
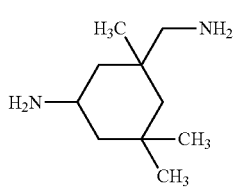
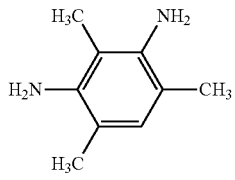
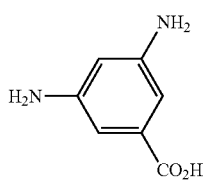
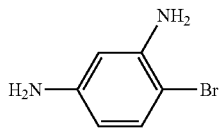
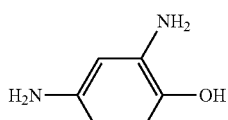
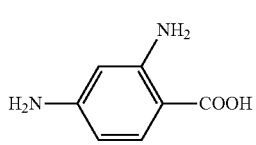
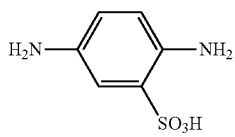
-continued
Diamine-16
Diamine-17
Diamine-18
Diamine-19
Diamine-20
Diamine-31
Diamine-32
Diamine-33
Diamine-34
Diamine-35
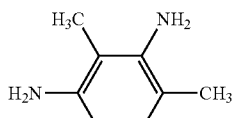
Diamine-36
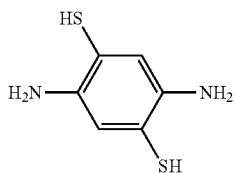
Diamine-37
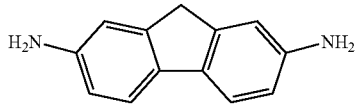
Diamine-38
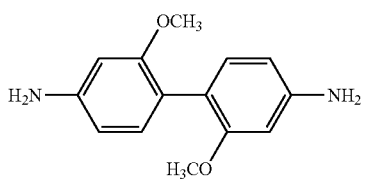
Diamine-39
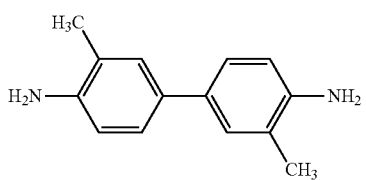
Diamine-40
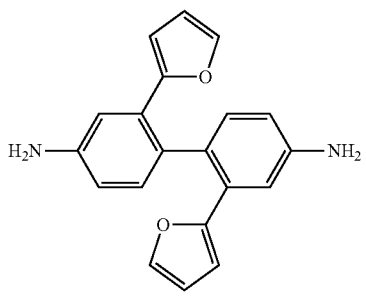
Diamine-41
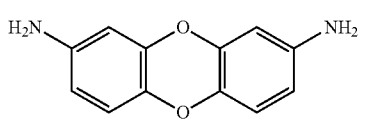
Diamine-42
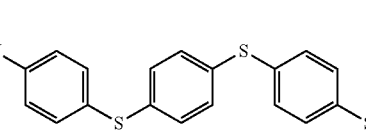
Diamine-43
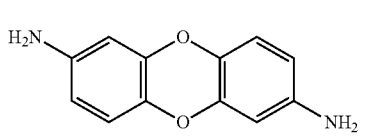
Diamine-44

Diamine-45
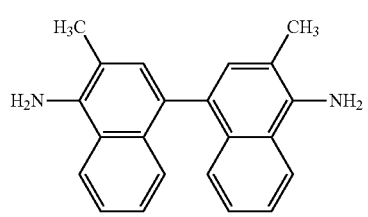
Diamine-46
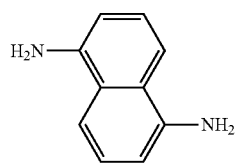
Diamine-47
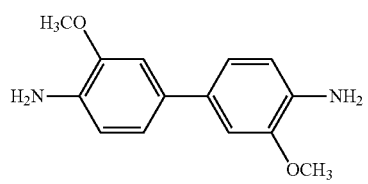
Diamine-48
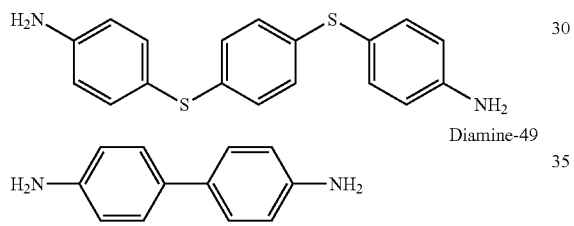
Diamine-49
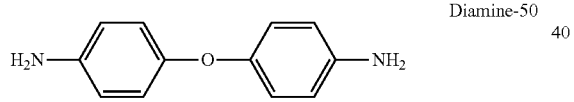
Diamine-50
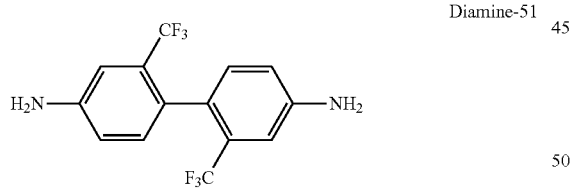
Diamine-51
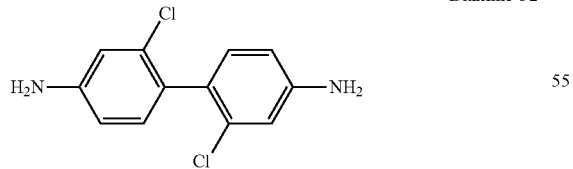
Diamine-52
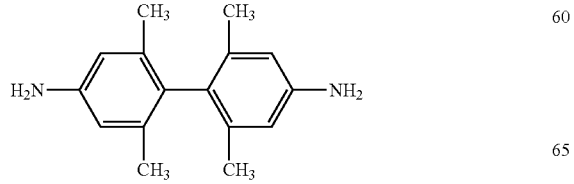
Diamine-53
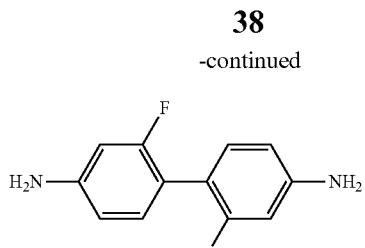
Diamine-54
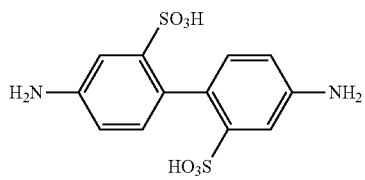
Diamine-55
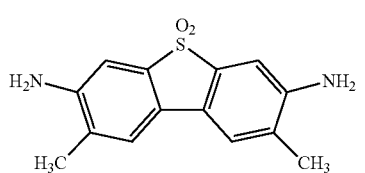
Diamine-56
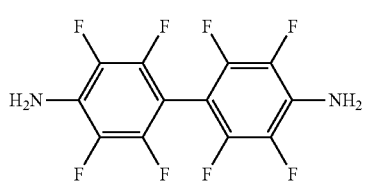
Diamine-57
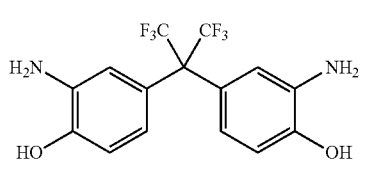
Diamine-58
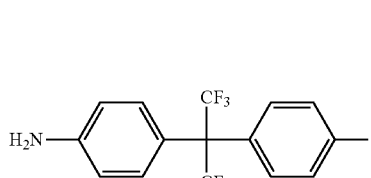
Diamine-59
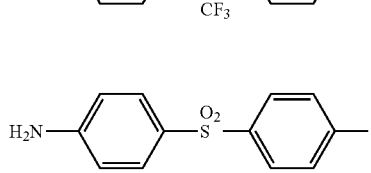
Diamine-60
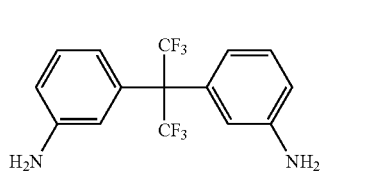
Diamine-61

Diamine-62

Diamine-63

Diamine-64

Diamine-65

Diamine-66

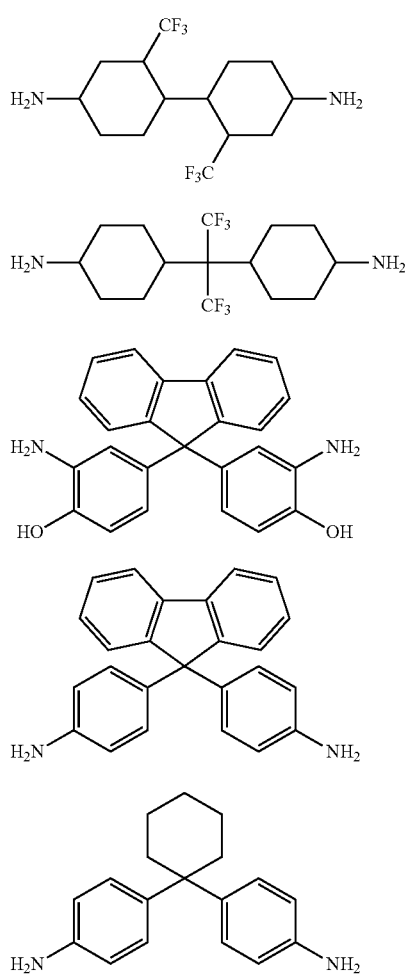

Diamine-67

Diamine-68

Diamine-69

Diamine-70

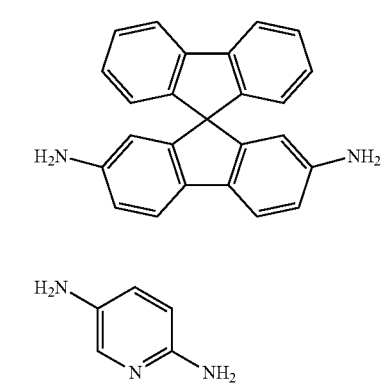
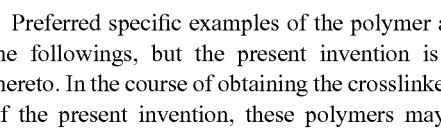

Preferred specific examples of the polymer are shown in the followings, but the present invention is not limited thereto. In the course of obtaining the crosslinked membrane of the present invention, these polymers may be used in combination with a crosslinking agent described below, or may be used alone when an inorganic alkoxide component is contained in the polymer.

P-1

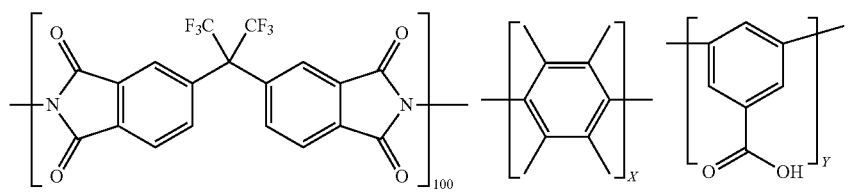

P-2

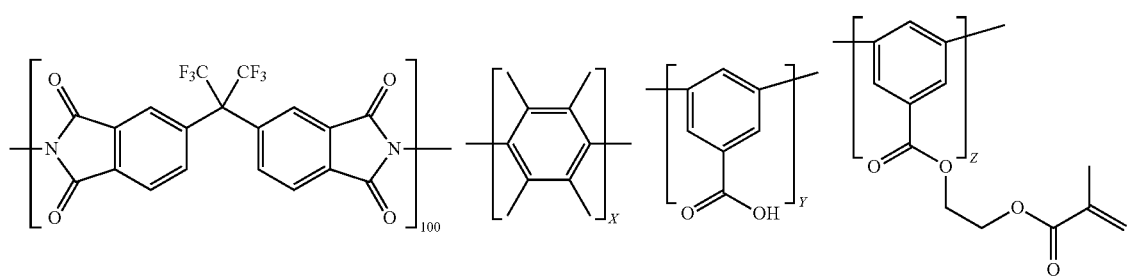

-continued
P-3
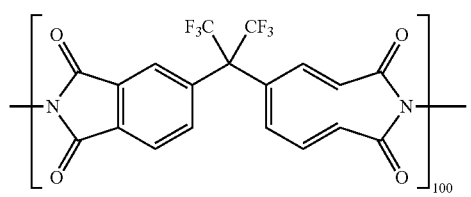 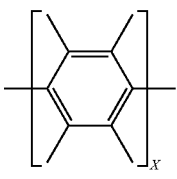 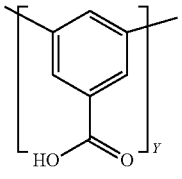 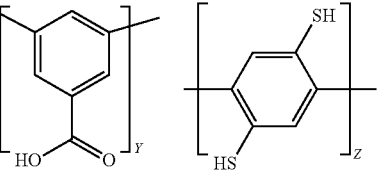
P-4
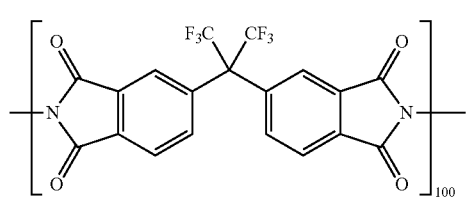 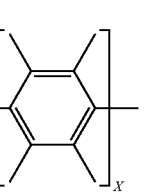 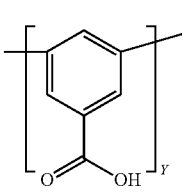 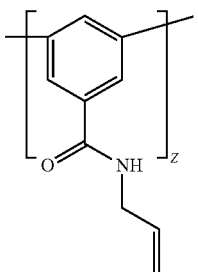
P-5
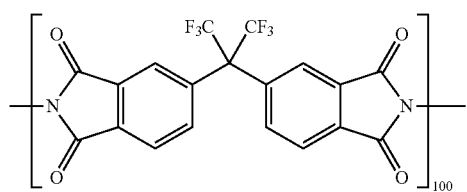 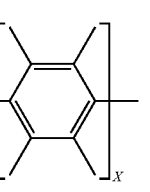 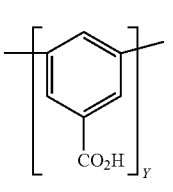 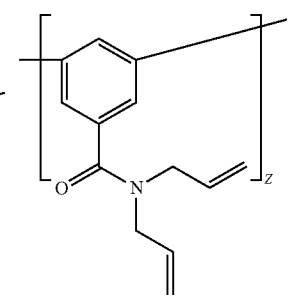
P-6
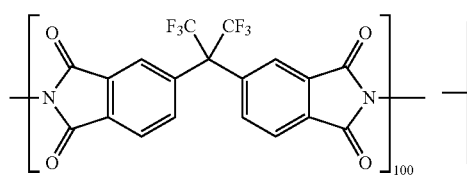 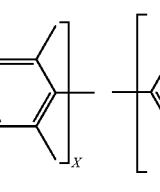 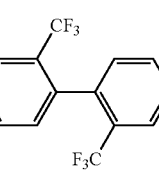 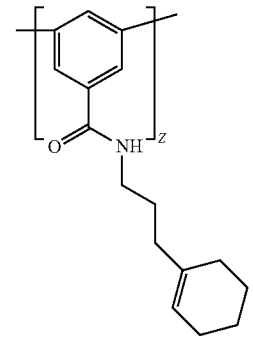
P-7
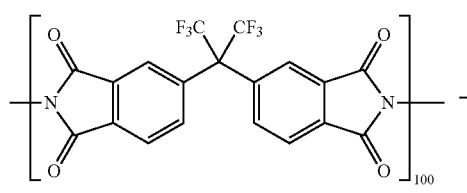 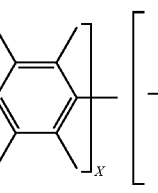 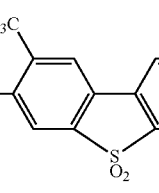 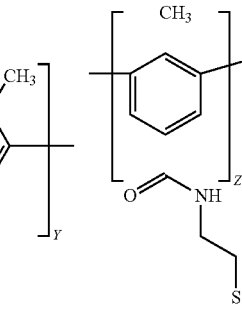

-continued
P-8
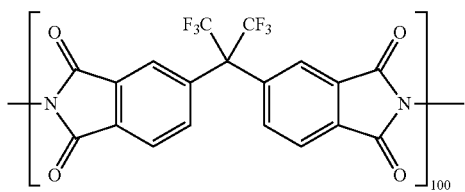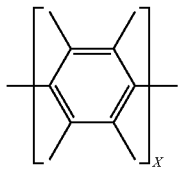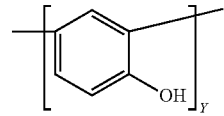
P-9
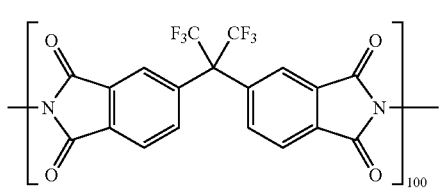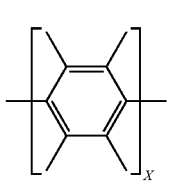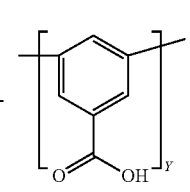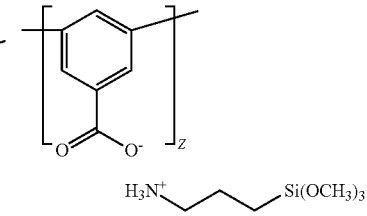
P-10
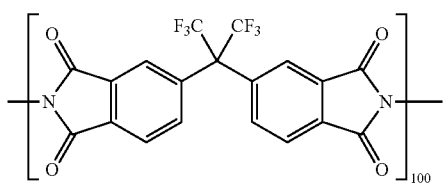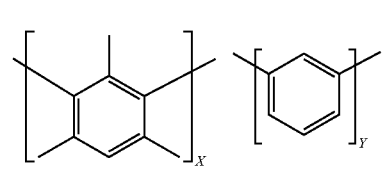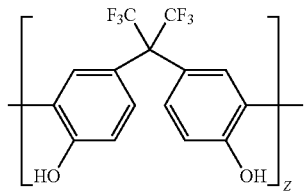
P-11
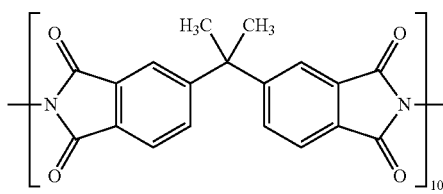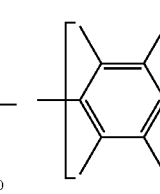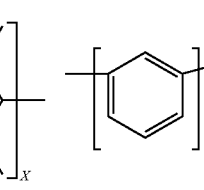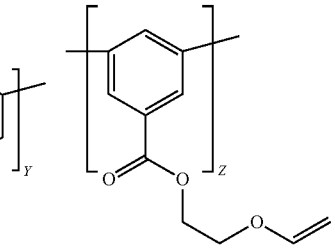
P-12
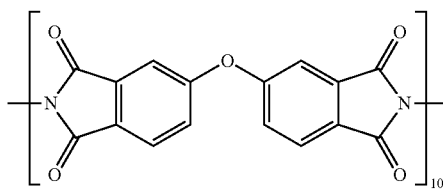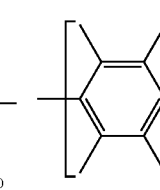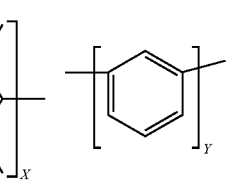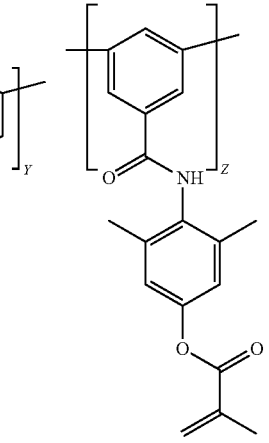

P-13
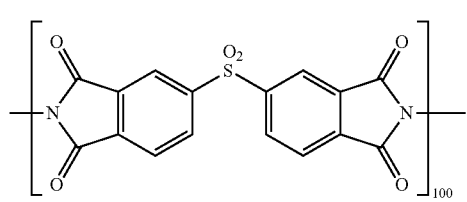 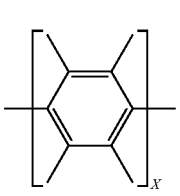 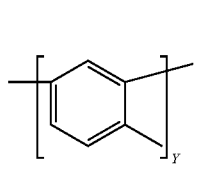 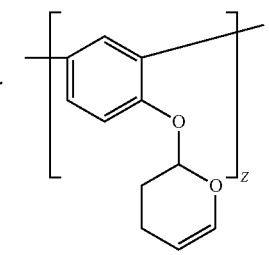
P-14
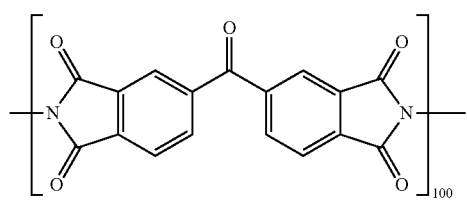 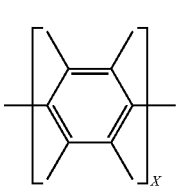 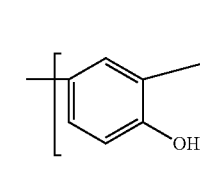 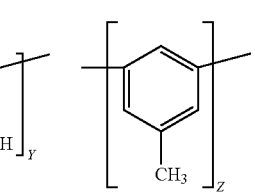
P-15
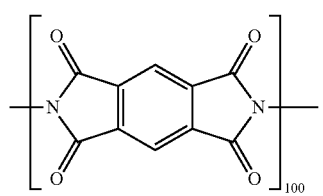 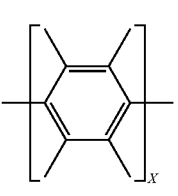 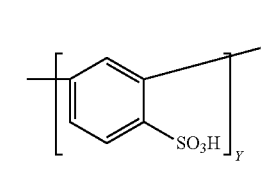 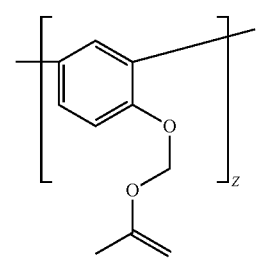
P-16
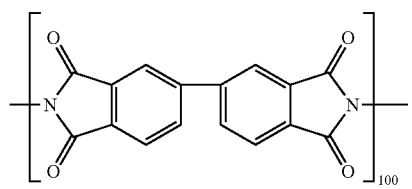 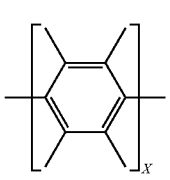 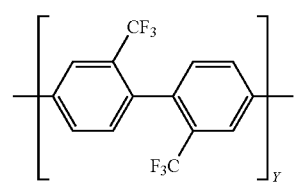 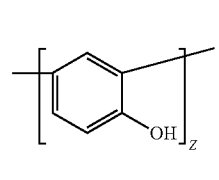
P-17
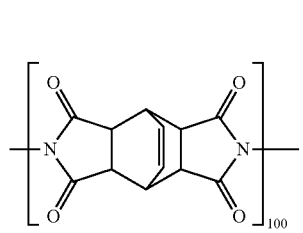 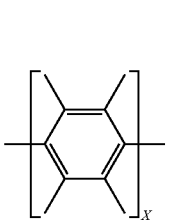 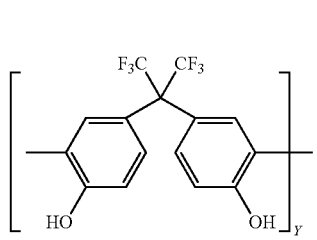 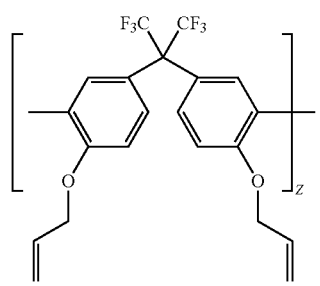
P-18
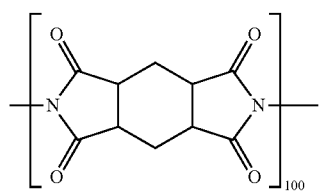 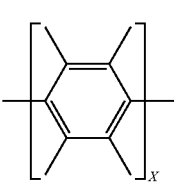 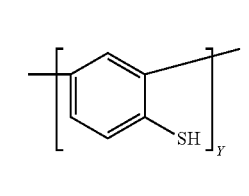 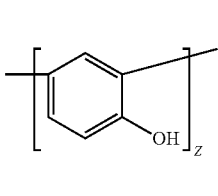

-continued
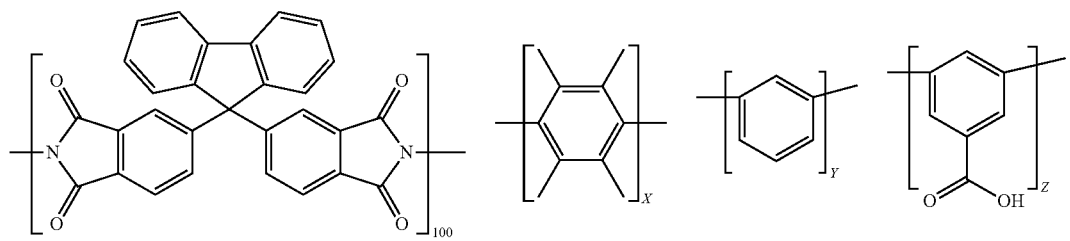
P-19
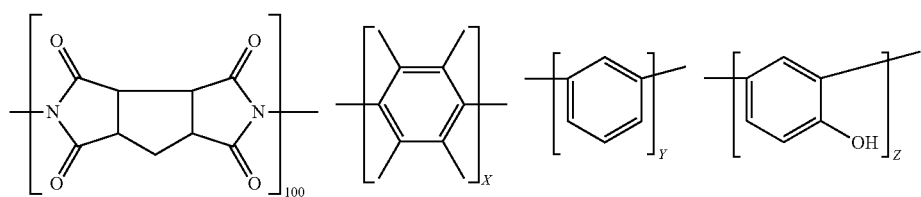
P-20
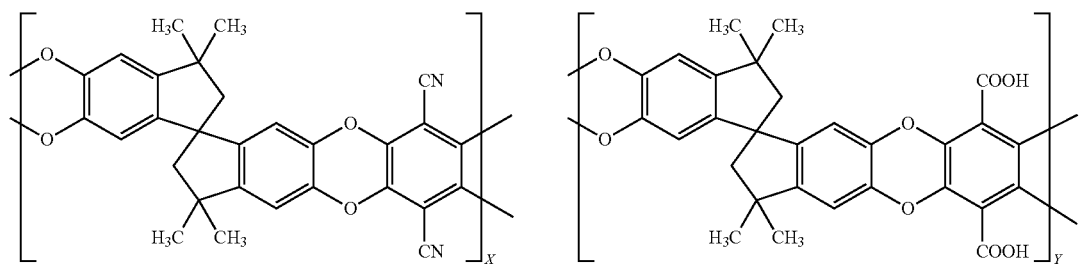
P-21
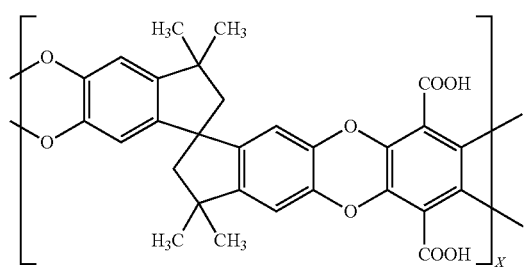
P-22
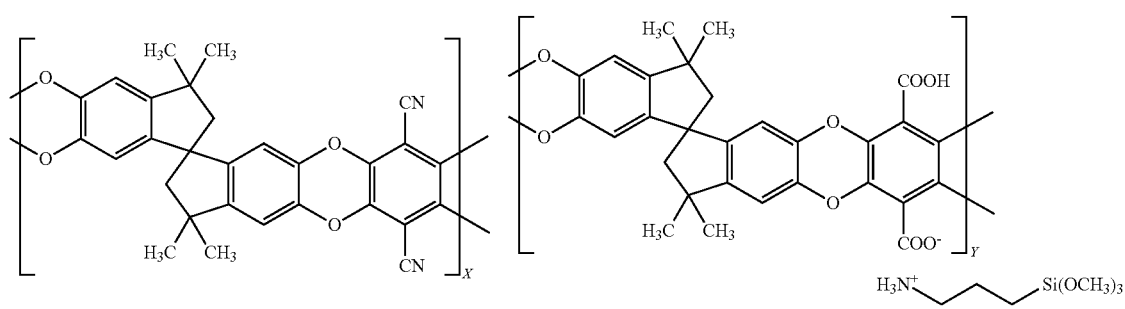
P-23

-continued
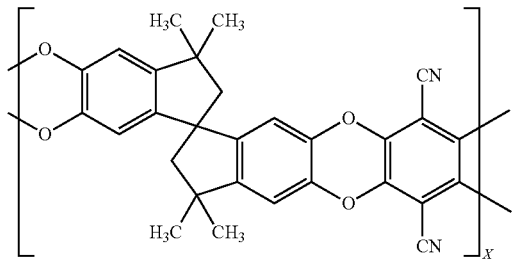
P-24
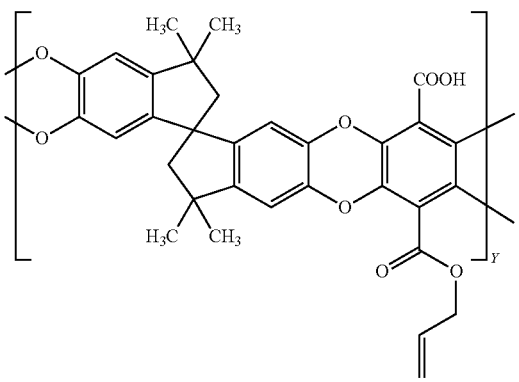
P-25
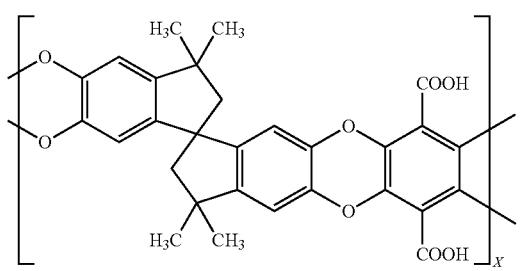
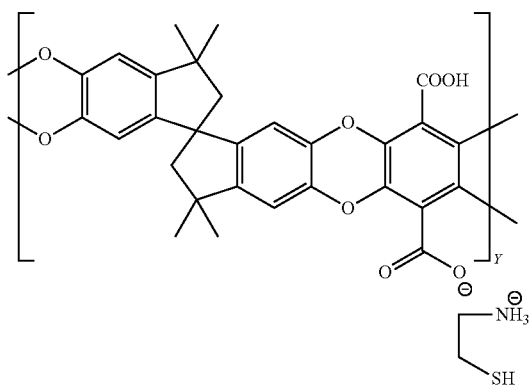
P-26
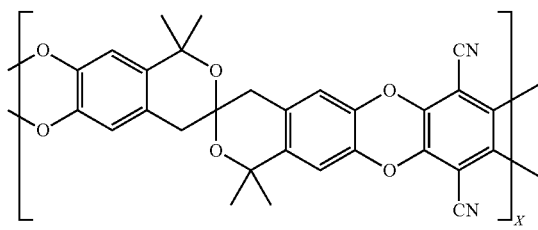
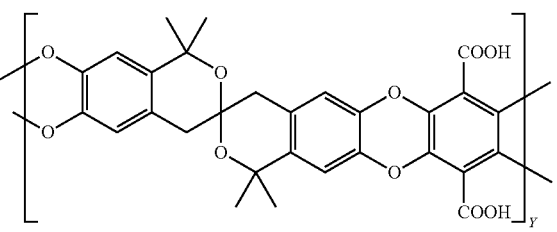
P-27
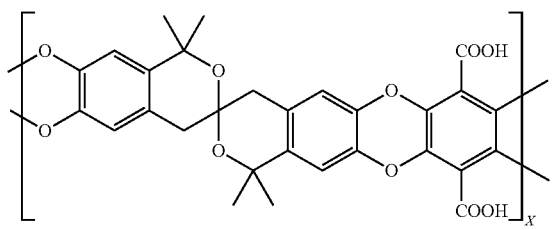
P-28
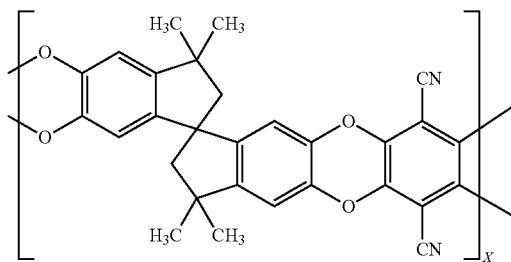
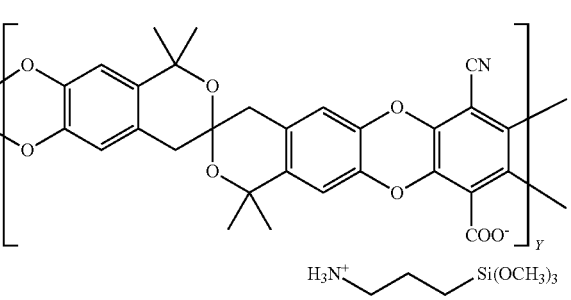

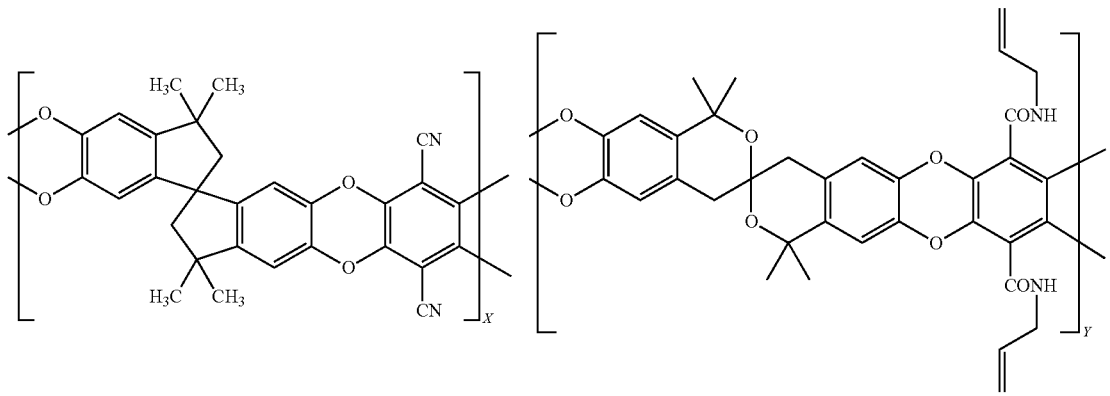

P-29

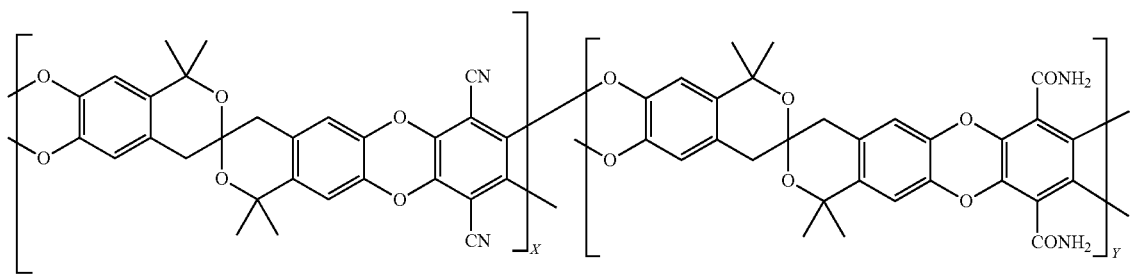

P-30

TABLE A

Molar ratio in the above-described chemical formulas [ratio of X/Y/Z based on 100 of a specific unit in the formula]

| | Average molecular weight | x | y | z |
|---|---|---|---|---|
| P-1 | 98,000 | 20 | 80 | — |
| P-2 | 113,000 | 20 | 70 | 10 |
| P-3 | 76,000 | 40 | 40 | 20 |
| P-4 | 97,000 | 20 | 50 | 30 |
| P-5 | 121,000 | 20 | 50 | 30 |
| P-6 | 66,000 | 15 | 70 | 15 |
| P-7 | 90,000 | 10 | 85 | 5 |
| P-8 | 91,000 | 10 | 90 | — |
| P-9 | 70,000 | 20 | 70 | 10 |
| P-10 | 81,000 | 20 | 70 | 10 |
| P-11 | 103,000 | 20 | 70 | 10 |
| P-12 | 96,000 | 20 | 70 | 10 |
| P-13 | 78,000 | 30 | 60 | 10 |
| P-14 | 131,000 | 10 | 80 | 10 |
| P-15 | 57,000 | 10 | 75 | 15 |
| P-16 | 67,000 | 5 | 5 | 90 |
| P-17 | 149,000 | 10 | 80 | 10 |
| P-18 | 153,000 | 80 | 10 | 10 |
| P-19 | 91,000 | 15 | 5 | 80 |
| P-20 | 93,000 | 15 | 5 | 80 |
| P-21 | 82,000 | 50 | 50 | — |
| P-22 | 79,000 | 100 | — | — |
| P-23 | 101,000 | 90 | 10 | — |
| P-24 | 114,000 | 80 | 20 | — |
| P-25 | 124,000 | 80 | 20 | — |
| P-26 | 103,000 | 70 | 30 | — |
| P-27 | 69,000 | 100 | — | — |
| P-28 | 71,000 | 85 | 15 | — |
| P-29 | 54,000 | 60 | 40 | — |
| P-30 | 52,000 | 20 | 80 | — |

The molecular weight is a weight-average molecular weight.

The polymer according to the present invention may be a copolymer with other monomers. Examples of the other monomers include known monomers such as acrylic acid esters, methacrylic acid esters, acrylamides, methacrylamides, vinyl esters, styrenes, acrylic acid, methacrylic acid, acrylonitrile, maleic anhydride and maleic imide. By copolymerizing these monomers, various physical properties such as membrane-forming property, membrane strength, hydrophilicity, hydrophobicity, solubility, reactivity and stability can be improved. The synthesis of monomers is for example carried out with reference to ester synthesis of "5$^{th}$ experiment science lecture 16, organic synthesis (II-1)" or handling or purification items of monomers of "5$^{th}$ experiment science lecture 26, polymer chemistry" edited by the Japanese Chemical Society (issued by MARUZEN Co., Ltd.).

Preferred specific examples of the crosslinking agent that can be used in combination with the polymer in the present invention are shown in the followings, but the present invention is not limited thereto.

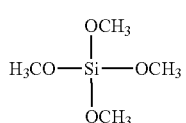

R-1

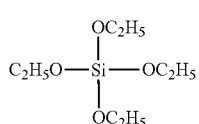

R-2

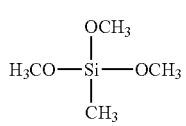

R-3

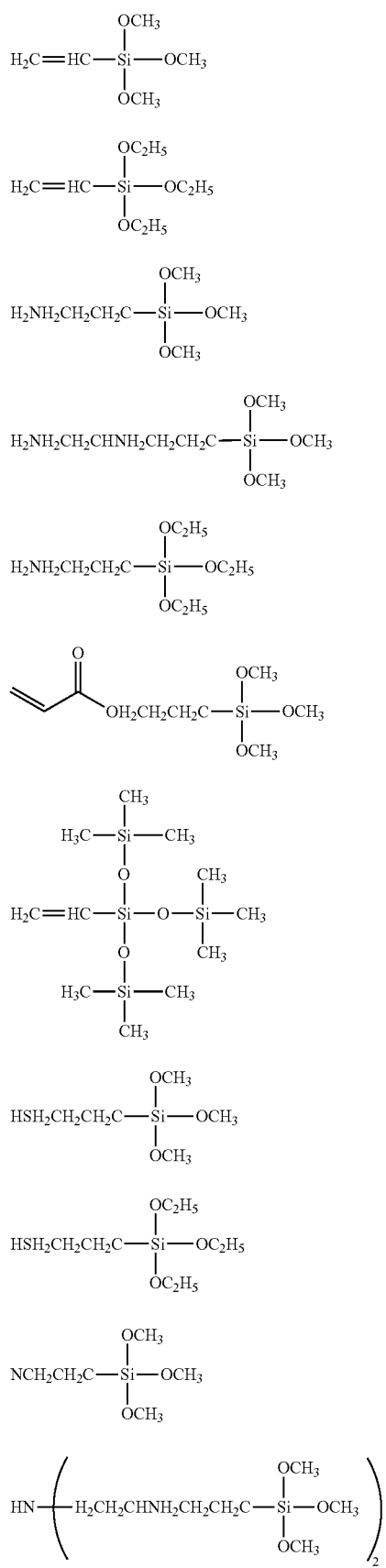
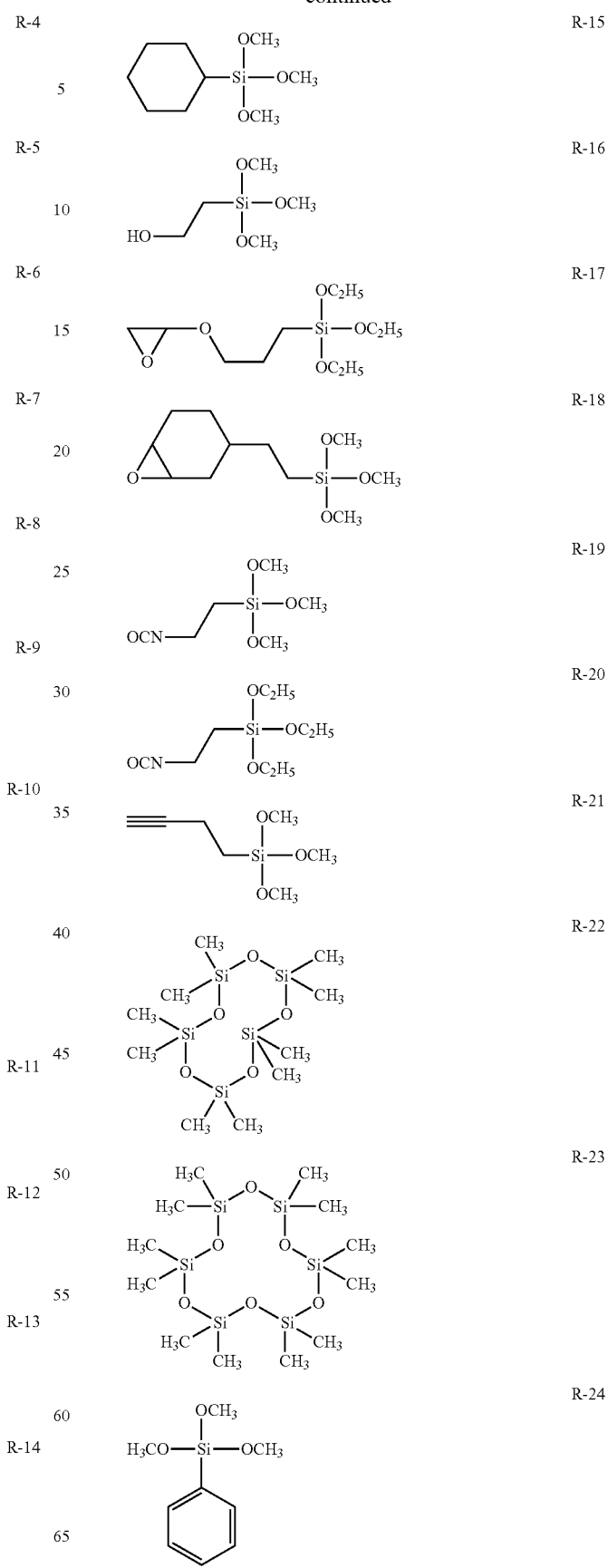

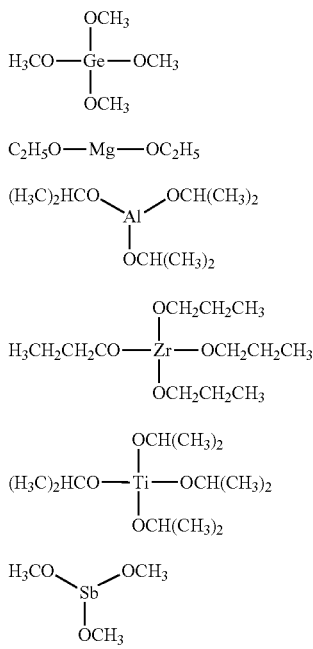

The gas separation membrane according to the present invention can be formed by curing by providing the group with some sort of energy such as heat or light.

As a monomer corresponding to partial structure of the polyimide compound or the polymer incorporating therein an oxanthrene unit, one processed into an oligomer or a prepolymer may be used. With regard to a polymer in obtaining a polymer compound, a copolymer having any form, such as a block copolymer, a random copolymer or a graft copolymer may be used.

In the polyimide compound, a ratio of partial structure represented by the above-described formula (I), (II-a), (II-b), (III-a) or (III-b) is not particularly defined. As a composition ratio of partial structure having a plurality of crosslinked structures increases, although an influence of molecular structure is significant, strength of a membrane and separation selectivity are generally improved but gas permeability tends to decrease. Therefore, as the composition ratio, the range of from 1 to 50% by mass, and preferably from 5 to 30% by mass is applied as the criterion, respectively. However, the composition ratio is not limited to these ranges, and the composition ratio is changed according to the purpose of gas separation (a recovery ratio, purity or the like), and thus gas permeability and separation selectivity are adjusted.

In the polyimide compound, a ratio of copolymerization ($R_I$) of the constitutional unit of formula (I), a ratio of copolymerization ($R_{II}$) of the constitutional unit of formulas (II-a) and (II-b), and a ratio of copolymerization ($R_{III}$) of the constitutional unit of formulas (III-a) and (III-b) are not particularly limited, but are preferably as described below.

|  | Preferred range | More preferred range | Particularly preferred range |
|---|---|---|---|
| $R_{II}$ | from 0 to 90 mol % | from 1 to 60 mol % | from 5 to 30 mol % |
| $R_{III}$ | from 0.1 to 90 mol % | from 5 to 50 mol % | from 5 to 30 mol % |
| $R_{IV}$* | from 0 to 90 mol % | from 0.1 to 90 mol % | from 1 to 90 mol % |

Note
*$R_{IV}$ is a ratio of copolymerization of any other constitutional unit, provided that an expression: $R_I = R_{II} + R_{III} + R_{IV}$ should be usually satisfied in the above-described ranges.

The molecular weight of the above-described polyimide compound or the polymer incorporating therein an oxanthrene unit is not particularly limited because of a crosslinked membrane. The molecular weight corresponding to each partial structure is preferably, as the mass average molecular weight, from 1,000 to 1,000,000, more preferably from 5,000 to 500,000, and further preferably from 5,000 to 100,000.

Unless it is explicitly stated otherwise, the molecular weight and the degree of dispersion are defined as the values obtained by measurement in accordance with a GPC (Gel Permeation Chromatography). The molecular weight is defined as polystyrene-converted mass-average molecular weight. The gel charged into the column used in the GPC method is preferably a gel having an aromatic compound as a repeating unit, and examples thereof include a gel made of styrene-divinylbenzene copolymers. The column is preferably used in the form where 2 to 6 columns are connected. Examples of a solvent used include ether-based solvents such as tetrahydrofuran, and amide-based solvents such as N-methylpyrrolidinone. The measurement is preferably carried out at a flow rate of the solvent in the range of from 0.1 to 2 mL/min, and most preferably in the range of from 0.5 to 1.5 mL/min. By carrying out the measurement within these ranges, there is no occurrence of loading in an apparatus, and thus, the measurement can be carried out further efficiently. The measurement temperature is preferably carried out at from 10° C. to 50° C., and most preferably from 20° C. to 40° C. A column and a carrier to be used can be properly selected, according to the property of a polymer compound to be measured.

[Crosslinked Polyimide Compound]
(Crosslinked Site Ratio [η])

In the present invention, a ratio [η] of a crosslinked site to an imide group of the above-described polyimide compound (the number of crosslinked sites/the number of imide groups) in the above-described crosslinked polyimide compound is preferably 0.13 or more, more preferably 0.15 or more, and further preferably 0.3 or more; and preferably 0.49 or less, more preferably 0.48 or less, further preferably 0.46 or less, and particularly preferably 0.4 or less. It should be noted that in the embodiment using a polymer incorporating therein an oxanthrene unit, the crosslinked site ratio [η] can be favorably calculated on the assumption that two times of oxanthrene ring numbers corresponds to the above-described number of imide groups.

"Crosslinked site ratio [η]" herein is based on the number of crosslinked crosslinkable functional groups, and expressed in terms of a calculated value (ratio) from which the number of uncrosslinked crosslinkable functional groups is excluded, even when any crosslinkable functional group is introduced into the polyimide compound. Generally, it is known that properties of the crosslinked membrane are exhibited sufficiently even by such a low crosslinked site ratio as a degree of 1 to 2% (η≈0.01 to 0.02). However, ordinary crosslinked site ratio is not enough to suppress impact in association with such high $CO_2$ concentration condition as targeted by the present invention, or impact in association with plasticization of the membrane due to the influence of aromatic compounds such as benzene, toluene, and xylene, or hydrocarbon impurities such as hexane and heptane each of which is contained in a natural gas. Adjustment of this value to 0.13 or more allows suppression of decrease in separation selectivity in the above-described environment. On the contrary, if the crosslinked site ratio [η] is high, the membrane is densely crosslinked, and therefore a proportion of a free volume space in the membrane reduces and gas permeability tends to decrease. As a result, adjustment of the η value to not too large one allows suppression of decrease in gas permeability in association with improvement in crosslink density, and also allows improvement in a mechanical strength such as a crack during bending, or brittleness.

Adjustment of this crosslinked site ratio to a desired range can be performed by appropriately adjusting, during the synthesis of the polyimide compound, an existence ratio of a crosslinkable functional group (for example, later-mentioned crosslinkable functional group density [γ]) or a crosslinking conversion ratio (for example, a ratio of the number of crosslinked functional groups based on the gross number of crosslinkable functional groups (crosslinking conversion ratio) [α]) by changing crosslinking reaction conditions, and according to a calculation, an expression: [η]=[γ]×[α]/200 is satisfied. Specifically, the crosslinked site ratio [η] can be improved by increasing a composition ratio of a monomer having a crosslinkable site in a predetermined range, enhancing reactivity, achieving polyfunctionalization, or using a raw material having another crosslinkable substituent in combination.

(Crosslinked Structure)

In the crosslinked resin of the present invention, it is indispensable to have a crosslinked structure containing the above-described formula (A), but it is preferable that an organic linking group is also contained as a linking group at the $P^a$ side. Specific examples of the organic linking group include a linking group represented by —$CR^{41}_2CH_2$—($R^{41}$ represents a hydrogen atom or an alkyl group having 1 to 10 carbon atoms), —$R^{42}COO$—, —$R^{42}OOC$— ($R^{42}$ represents an alkyl group having 1 to 10 carbon atoms), —$NR^{43}CO$— ($R^{43}$ represents a hydrogen atom or an alkyl group having 1 to 10 carbon atoms), —$CH_2OCH_2$—, —$CH_2SCH_2$—, —OC(=O)O—, —C(=O)$O^-N^+R^{44}_3$— ($R^{44}$ represents a hydrogen atom or an alkyl group having 1 to 10 carbon atoms), —$SO_3^-N^+R^{45}_3$— ($R^{45}$ represents a hydrogen atom or an alkyl group having 1 to 10 carbon atoms) or —$PO_3^-N^+R^{46}_3$—($R^{46}$ represents a hydrogen atom or an alkyl group having 1 to 10 carbon atoms); or a combination of these. Among these, —C(=O)$O^-N^+R^{44}_3$— or —$CH_2SCH_2$— is more preferable.

(Crosslinkable Functional Group Density [γ])

A ratio of the number of functional groups Lb of formulas (III-a) and (III-b) to the repeating unit represented by formula (I) is referred to as crosslinkable functional group density [γ]. A preferred range of this γ (the number of functional groups Lb's/the number of repeating units represented by formula (I)) is preferably 0.1 or more, further preferably 0.3 or more, more preferably 0.5 or more, further preferably 0.6 or more, and most preferably 0.7 or more. The upper limit thereof is not particularly limited, but practically 2.0 or less, and preferably 0.95 or less. It should be noted that in the embodiment using a polymer incorporating therein an oxanthrene unit, the crosslinkable functional group density [γ] can be calculated on the assumption that the number of the oxanthrene ring corresponds to the number of the above-described formula (I).

A preferable range thereof is described below with respect to each polymer species. In the case of a polyimide-based resin, the range is preferably 0.6 or more, and more preferably 0.7 or more. The upper limit thereof is practically 0.95 or less. In the case of an oxanthrene-based resin, the range is preferably 1.2 or more, and more preferably 1.4 or more. The upper limit thereof is practically 4 or less.

The function where the above-described crosslinkable functional group density [γ] effects on the crosslinked resin is not completely explained. However, it is understood that γ represents a density of the polar group, and therefore γ can be a parameter which influences separation selectivity of the gas. In view of the past findings of the present inventor, when a ratio of the polar group is increased, an interaction between polymer chains is strengthened, and therefore a density of the membrane increases. That is, both a rate of the free volume in the membrane and an average size of the free volume space become lower. If the average size of the free volume becomes smaller, separation selectivity in terms of diffusion coefficient of the gas molecule arising from a size of the gas molecule is improved, and therefore on the one hand, separation selectivity is improved, but because a rate of the free volume space becomes lower, gas permeability tends to be adversely decreased. In particular, its influence becomes remarkable in a gas separation treatment under high pressure over the range of from 40 atmospheric pressure to 60 atmospheric pressure. Adjustment of the above-described γ to a particularly preferable range of 0.7 or more but 0.95 or less allows obtaining of the gas separation membrane that achieves a balance of separation selectivity and gas permeability each of which satisfies practical requirements. This aspect is also an important advantage involved in a preferable embodiment of the present invention.

This crosslinkable functional group density can be adjusted by an amount of charging a substrate (monomer) on synthesizing the polyimide compound.

(Crosslinking Conversion Ratio [α])

The crosslinking conversion ratio [α] of the present invention is generally difficult to carry out an analysis thereof because of the crosslinked membrane. However, it can be estimated by a degree of decrease between before and after the cross-linkage in terms of the peak of —O-$M^1$-O— bond ($M^1$ has the same meaning as that of formula (A), when $M^1$ is Si, it is generally 1100 $cm^{-1}$), for example, in measurement of a reflectance infrared spectroscopy, or in terms of the double bond peak in infrared spectroscopy or $^1$H-NMR, or by gel fraction calculated from the difference between the crosslinked membrane and a monomer component eluted after swelling with a suitable solvent. The crosslinking conversion ratio is preferably 20% or more and 100% or less, more preferably 50% or more and 94% or less, and further preferably 30% or more and 89% or less.

This crosslinking conversion ratio can be adjusted by an addition amount of a crosslinking agent and crosslinking conditions in a sol-gel reaction of a compound, and the crosslinking conversion ratio can be adjusted by adjusting variously a kind of a polymerization initiator, temperature of the crosslinking reaction, a substrate concentration, an amount of heat, and an amount of light and irradiation time of active radiation. Specific examples include, in order to enhance a percentage of reaction in the crosslinking reaction in radical polymerization, increasing gross energy of heat or light energy, and for a material, improving activity of a photoinitiator (e.g., a ketone-based compound) or a thermal initiator (e.g., a compound having a low decomposition temperature for an azo compound), each being a polymerization initiator.

[Method of Producing Gas Separation Membrane]

The method of producing a gas separation membrane according to the present invention is preferably a production method by which a membrane is formed by coating a coating liquid containing the above-described polyimide compound onto a support, and irradiating the resultant coated membrane with active radiation. The component composition of the coating liquid (dope) for constituting the coated membrane is not particularly limited, but preferably contains the above-described polyimide compound and a polymerization initiator in an organic solvent. The content of the polyimide compound is not particularly limited, but the compound is contained in the coating liquid in an amount of preferably from 0.1 to 30% by mass, and further preferably from 1 to 10% by mass. Adjustment of the content to the above-described lower limit or more allows, when the concentration is weak, minimization of a phenomenon of an increase in possibility of producing a defect on a surface layer contributing to separation due to easy permeation into a lower layer upon forming the membrane on the porous support. Adjustment of the content to the above-described upper limit or lower allows minimization of a phenomenon of thin layer formation or a decrease in permeability as caused by being packed in pores with high concentration upon forming the membrane on the porous support in the case of a high concentration. The gas separation membrane according to the present invention can be suitably produced by adjusting the molecular weight, structure and the composition of the polymer in the separating layer, and also solution viscosity of the polymer.

Film formation is preferably carried out by coating a coating liquid for forming the above-described separation layer over a support or the like, and then curing it by heat. The heating temperature is not particularly limited, but in view of deterioration or the like of the support due to extreme heating, it is preferably 100° C. or lower, and more preferably 70° C. or lower. From the viewpoint of an efficient heating treatment, it is preferably 20° C. or higher, and more preferably 40° C. or higher. The heating time is not particularly limited, but practically 10 min or more and 16 hours or less.

[Organic Solvent]

The organic solvent is not particularly limited, and specific examples include hydrocarbon-based organic solvents such as n-hexane and n-heptane; ester-based organic solvents such as methyl acetate, ethyl acetate, and butyl acetate; lower alcohols such as methanol, ethanol, n-propanol, isopropanol, n-butanol, isobutanol and tert-butanol; aliphatic ketones such as acetone, methyl ethyl ketone, methyl isobutyl ketone, diacetone alcohol, cyclopentanone, and cyclohexanone; ether-based organic solvents such as ethylene glycol, diethylene glycol, triethylene glycol, glycerin, propylene glycol, ethylene glycol monomethyl or monoethyl ether, propylene glycol methyl ether, dipropylene glycol methyl ether, tripropylene glycol methyl ether, ethylene glycol phenyl ether, propylene glycol phenyl ether, diethylene glycol monomethyl or monoethyl ether, diethylene glycol monobutyl ether, triethylene glycol monomethyl or monoethyl ether, dibutyl ether, tetrahydrofuran, methyl cyclopentyl ether, and dioxane; N-methylpyrrolidone, 2-pyrrolidone, dimethylformamide, dimethyl imidazolidinone, dimethyl sulfoxide, dimethyl acetamide and the like. These organic solvents are suitably selected within the range in which the solvents do not exert a harmful influence, such as corrosion of the support, and preferably an ester-based solvent (preferably butyl acetate), an alcohol-based solvent (preferably methanol, ethanol, isopropanol, and isobutanol), aliphatic ketones (preferably methyl ethyl ketone, methyl isobutyl ketone, diacetone alcohol, cyclopentanone, and cyclohexanone) or an ether type solvent (e.g., ethylene glycol, diethylene glycol monomethyl ether, and methyl cyclopentylether); and further preferably an aliphatic ketone-based solvent, an alcohol-based solvent or an ether-based solvent. These compounds may be used alone or in combination of two or more types.

The gas separation membrane preferably contains the later-mentioned polymerization initiator and is formed by curing by irradiation with active radiation. Here, the active radiation is not particularly limited so long as it produces energy capable of generating initiation species in the membrane composition when irradiated and broadly includes α-ray, γ-ray, X-rays, ultraviolet rays, visible rays, electron beams and the like. Of these, ultraviolet rays and electron beams are preferred and ultraviolet rays are particularly preferred, in terms of curing sensitivity and easy availability of apparatuses.

When ultraviolet rays are used in the present invention, addition of the following photopolymerization initiator is necessary. Electric beam curing is preferred since a polymerization initiator is unnecessary and a permeation depth is large. An electron beam accelerator may utilize a scanning manner, a double scanning manner or a curtain beam manner and is preferably a curtain beam manner capable of obtaining high power at a relatively low cost. Regarding properties of electron beam, an acceleration voltage is from 30 to 1000 kV, preferably from 50 to 300 kV. An absorbed dose is preferably from 5 to 200 kGy (from 0.5 to 20 Mrad), more preferably from 20 to 100 kGy (from 2 to 10 Mrad). When the acceleration voltage and absorbed dose are within these ranges, a sufficient amount of energy is permeated and energy efficiency is thus good. Regarding the atmosphere, at which an electron beam is irradiated, an oxygen concentration is preferably 200 ppm or less under a nitrogen atmosphere. Within this range, cross-linkage and curing close to the surface proceed preferably.

A mercury lamp is used as a light source of ultraviolet rays. The mercury lamp utilizes a lamp of from 20 to 240 W/cm$^2$ and is used at a speed of from 0.3 to 20 m/min. The distance between the membrane and the mercury lamp is preferably generally from 1 to 30 cm. When a desktop-type ultraviolet ray curing apparatus is used, curing is preferably performed after suitably controlling light amount and position of light source according to the material and environments for from about 1 second to about 10 minutes.

Known radiation curing apparatuses, conditions and the like described in "UV-EB curing techniques" (issued by Technical Integration Center, Corp.) or "Application techniques of low-energy electron beam irradiation" (2000, issued by CMC Co., Ltd.) and the like may be used. Curing may be carried out in conjunction with heating.

[Polymerization Initiator]

In the process of forming the gas separation membrane of the present invention, a radical polymerization initiator is preferably added and a photopolymerization initiator is particularly preferably added.

The photopolymerization initiator in the present invention is a compound that causes chemical reaction via action of light or interaction with a sensitizing dye in an electron-excited state and thus produces at least one kind of radical, acid and base.

The photopolymerization initiator may be appropriately selected from those having a sensitivity with respect to irradiated active radiation such as ultraviolet rays of from 400 to 200 nm, far ultraviolet rays, g-rays, h-rays, i-rays, KrF excimer laser beam, ArF excimer laser beam, electron beam, X-rays, molecular beam or ion beam.

Specifically, the photopolymerization initiator may be selected from those known to those skilled in the art without limitation and specific examples thereof include the compounds described in Bruce M. Monroe et al., Chemical Review, 93, 435 (1993), R. S, Davidson, Journal of Photochemistry and biology A: Chemistry, 73, 81 (1993), J. P. Faussier, "Photonitiated Polymerization—Theory and Applications": Rapra Review Vol. 9, Report, Rapra Technology (1998), and M. Tsunooka et al., Prog. Polym. Sci., 21, 1 (1996). It is also possible to use the compounds for chemically amplified photoresists or photocation polymerization described in "Organic Materials for Imaging", edited by the Japanese Research Association for Organic Electronics Materials, published by Bunshin Design Printing Publishing (1993), pp. 187-192. Further, compounds that cause bond cleavage in oxidative or reductive manner via interaction with a sensitizing dye in an electron-excited state are also known, such as those described in F. D. Saeva, Topics in Current Chemistry, 156, 59 (1990), G. G. Maslak, Topics in Current Chemistry, 168, 1 (1993), H. B. Shuster et al., JACS, 112, 6329 (1990), and I. D. F. Eaton et al., JACS, 102, 3298 (1980).

Preferred examples of the photopolymerization initiator include (a) aromatic ketones, (b) aromatic onium salt compounds, (c) organic peroxides, (d) hexaaryl biimidazole compounds, (e) ketoxime ester compounds, (f) borate compounds, (g) azinium compounds, (h) metallocene compounds, (i) active ester compounds, and (j) compounds having a carbon-halogen bond.

Preferred examples of the (a) aromatic ketones include the compounds having a benzophenone skeleton or a thioxanthone skeleton described in J. P. Fouassier and J. F. Rabek, "Radiation Curing in Polymer Science and Technology" (1993), pp. 77-117. More preferred examples of the (a) aromatic ketones include α-thiobenzophenone compounds described in JP-B-47-6416 ("JP-B" means examined Japanese patent publication), benzoin ether compounds described in JP-B-47-3981, α-substituted benzoin compounds described in JP-B-47-22326, benzoin derivatives described in JP-B-47-23664, aroyl phosphonates described in JP-A-57-30704 ("JP-A" means unexamined published Japanese patent application), dialkoxybenzophenones described in JP-B-60-26483, benzoin ethers described in JP-B-60-26403 and JP-A-62-81345, α-aminobenzophenones described in JP-B-1-34242, U.S. Pat. No. 4,318,791 and EP 0284561 A1, p-di(dimethylaminobenzoyl) benzenes described in JP-A-2-211452, thio-substituted aromatic ketones described in JP-A-61-194062, acylphosphinesulfide described in JP-B-2-9597, acylphosphine described in JP-B-2-9596, thioxanthones described in JP-B-63-61950, and coumarins described in JP-B-59-42864.

The (b) aromatic onium salts include aromatic onium salts of elements of Groups V, VI and VII of the periodic table, and more specifically, N, P, As, Sb, Bi, O, S, Se, Te or I. Preferred examples of the (b) aromatic onium salts include: iodonium salts described in European Patent No. 104143, U.S. Pat. No. 4,837,124, JP-A-2-150848 and JP-A-2-96514; sulfonium salts described in European Patent No. 370693, European Patent No. 233567, European Patent No. 297443, European Patent No. 297442, European Patent No. 279210, European Patent No. 422570, U.S. Pat. No. 3,902,144, U.S. Pat. No. 4,933,377, U.S. Pat. No. 4,760,013, U.S. Pat. No. 4,734,444 and U.S. Pat. No. 2,833,827; diazonium salts (such as benzene diazonium which may contain a substituent); resins of diazonium salts (such as formaldehyde resins of diazo diphenylamine); N-alkoxy pyrridium salts (such as those described in U.S. Pat. No. 4,743,528, JP-A-63-138345, JP-A-63-142345, JP-A-63-142346 and JP-B-46-42363, and more specifically 1-methoxy-4-phenyl pyrridium tetrafluoroborate); and compounds described in JP-B-52-147277, JP-B-52-14278 and JP-B-52-14279. These salts produce radicals or acids as the active species.

The (c) "organic peroxides" include almost all the organic compounds having one or more oxygen-oxygen bonds in the molecule, and preferred examples thereof include peroxide esters such as 3,3',4,4'-tetra-(t-butylperoxycarbonyl)benzophenone, 3,3',4,4'-tetra-(t-amylperoxycarbonyl)benzophenone, 3,3',4,4'-tetra-(t-hexylperoxycarbonyl)benzophenone, 3,3',4,4'-tetra-(t-octylperoxycarbonyl)benzophenone, 3,3',4,4'-tetra-(cumylperoxycarbonyl)benzophenone, 3,3',4,4'-tetra-(p-iso-propylcumylperoxycarbonyl)benzophenone, and di-t-butyl di-peroxy isophthalate.

Examples of the (d) hexaaryl biimidazoles include lophine dimers described in JP-B-45-37377 and JP-B-44-86516, such as 2,2'-bis(o-chlorophenyl)-4,4',5,5'-tetraphenyl biimidazole, 2,2'-bis(o-bromophenyl)-4,4',5,5'-tetraphenyl biimidazole, 2,2'-bis(o,p-dichloro-phenyl)-4,4',5,5'-tetraphenyl biimidazole, 2,2'-bis(o-chlorophenyl)-4,4',5,5'-tetra-(m-methoxyphenyl) biimidazole, 2,2'-bis(o,o'-dichloro-phenyl)-4,4',5,5'-tetraphenyl biimidazole, 2,2'-bis(o-nitrophenyl)-4,4',5,5'-tetraphenyl biimidazole, 2,2'-bis(o-methyl-phenyl)-4,4',5,5'-tetraphenyl biimidazole, and 2,2'-bis(o-trifluoro-phenyl)-4,4',5,5'-tetraphenyl biimidazole.

Examples of the (e) ketoxium esters include 3-benzoyloxy-iminobutan-2-one, 3-acetoxy-iminobutan-2-one, 3-propionyloxy-iminobutan-2-one, 2-acetoxy-iminopentan-3-one, 2-acetoxyimino-1-phenylpropan-1-one, 2-benzoyloxyimino-1-phenylpropan-1-one, 3-p-toluene sulfonyloxy iminobutan-2-one, and 2-ethoxycarbonyl oxyimino-1-phenylpropan-1-one.

Examples of the (f) borate salts, which are other examples of the photopolymerization initiator in the present invention, include the compounds described in U.S. Pat. No. 3,567,453, U.S. Pat. No. 4,343,891, European Patent No. 109772 and European Patent No. 109773.

Examples of the (g) azinium salt compounds, which are other examples of the photopolymerization initiator, include compounds having N—O bond described in JP-A-63-138345, JP-A-63-142345, JP-A-63-142346, JP-A-63-143537 and JP-B-46-42363.

Examples of the (h) metallocene compounds, which are other examples of the photopolymerization initiator, include titanocene compounds as described in JP-A-59-152396, JP-A-61-151197, JP-A-63-41484, JP-A-2-249, and JP-A-2-4705, and iron-arene complexes described in JP-A-1-304453 and JP-A-1-152109.

Specific examples of the aforementioned titanocene compound include di-cyclopentadienyl-Ti-di-chloride, di-cyclopentadienyl-Ti-bis-phenyl, di-cyclopentadienyl-Ti-bis-2,3,4,5,6-pentafluorophen-1-yl, di-cyclopentadienyl-Ti-bis-2,3,5,6-tetrafluorophen-1-yl, di-cyclopentadienyl-Ti-bis-2,4,6-trifluorophen-1-yl, di-cyclopentadienyl-Ti-2,6-di-fluorophen-1-yl, di-cyclopentadienyl-Ti-bis-2,4-di-fluorophen-1-yl, di-methyl-cyclopentadienyl-Ti-bis-2,3,4,5,6-pentafluorophen-1-yl, di-methyl-cyclopentadienyl-Ti-bis-2,3,5,6-tetrafluorophen-1-yl, di-methyl-cyclopentadienyl-Ti-bis-2,4-difluorophen-1-yl, bis(cyclopentadienyl)-bis(2,6-difluoro-3-(pyr-1-yl)phenyl)titanium, bis(cyclopentadienyl)

bis[2,6-difluoro-3-(methyl-sulfonamide)phenyl]titanium, and bis(cyclopentadienyl)bis[2,6-difluoro-3-(N-butyl biaroyl-amino)phenyl]titanium.

Examples of the (i) active ester compounds include nitrobenzyl ester compounds described in European Patent No. 0290750, European Patent No. 046083, European Patent No. 156153, European Patent No. 271851, European Patent No. 0388343, U.S. Pat. No. 3,901,710, U.S. Pat. No. 4,181,531, JP-A-60-198538, and JP-A-53-133022; iminosulfonate compounds described in European Patent No. 0199672, European Patent No. 84515, European Patent No. 199672, European Patent No. 044115, European Patent No. 0101122, U.S. Pat. No. 4,618,564, U.S. Pat. No. 4,371,605, U.S. Pat. No. 4,431,774, JP-A-64-18143, JP-A-2-245756, and JP-A-4-365048; and compounds described in JP-B-62-6223, JP-B-63-14340 and JP-A-59-174831.

Preferred examples of the (j) compounds containing a carbon-halogen bond include a compound as described by Wakabayashi, et al., in Bull. Chem. Soc. Japan, 42, 2924 (1969), a compound described in GB Patent No. 1388492, a compound described in JP-A-53-133428, and a compound as described in German Patent No. 3337024.

Other examples include a compound described by F. C. Schaefer, et. al., in J. Org. Chem., 29, 1527 (1964), a compound described in JP-A-62-58241, and a compound described in JP-A-5-281728. Other examples include a compound described in German Patent No. 2641100, a compound described in German Patent No. 3333450, a group of compounds described in German Patent No. 3021590, and a group of compounds described in German Patent 3021599.

The organic-inorganic hybrid structure in the present invention is desirably constructed by a sol-gel reaction (Reference Literature: Sol-Gel ho Oyo no Tenkai (Sol-Gel Method: Evolution of application), authored by Sumio Sakka, CMC Publishing Co., Ltd.). In the sol-gel method, water is added to an inorganic alkoxide to hydrolyze it, and then the hydrolysate is subjected to a reaction, and the reaction is accelerated in the presence of an acid or a base. Therefore, such an activating agent that generates radical(s) and further an acid or a base upon irradiation with active radiation is more preferably used in the present invention. More specifically, as a photo-acid-radical generating agent, 0-tosyl benzoin (CAS:1678-43-9) and the like are preferably used (Reference Literature: 1) Photo-curing of acryl-functional alkoxysilane,
a) Hiroshi Inoue, Kimihiro Matsukawa, Toshikatsu Arizono, Yoshiko Tanaka, Noboru Nishioka, Network Polymer, 19, 195(1998), b) H. Inoue, K. Matsukawa, Y. Tanaka, N. Nishioka, J. Photopolym. Sci. Technol., 12, 129 (1999), 2) Photocuring of acrylic-silica organic-inorganic hybrid, H. Inoue, Y. Matsuura, K. Matsukawa, Y. Otani, N. Higashi, M. Niwa, J. Photopolym. Sci. Technol., 13, 109 (2000)).

The amount to be used of the polymerization initiator is preferably from 0.001 mass part to 10 mass parts, more preferably from 0.01 mass part to 5 mass parts, based on 1 mass part of the polymerizable compound.

[Cosensitizer]

A known compound having a function of further improving sensitivity or suppressing polymerization inhibition due to oxygen may be added as a cosensitizer in the process of producing the gas separation membrane of the present invention.

Examples of such a cosensitizer include amines such as the compounds described in M. R. Sander et al., "Journal of Polymer Society", Vol. 10, p. 3173 (1972), JP-B-44-20189, JP-A-51-82102, JP-A-52-134692, JP-A-59-138205, JP-A-60-84305, JP-A-62-18537, JP-A-64-33104 and Research Disclosure Vol. 33825. Specific examples include triethanolamine, ethyl p-dimethylaminobenzoate, p-formyldimethylaniline and p-methylthiodimethylaniline.

Other Examples of the cosensitizer include thiols and sulfides, such as thiol compounds described in JP-A-53-702, JP-B-55-500806 and JP-A-5-142772 and disulfide compounds described in JP-A-56-75643. Specific examples include 2-mercaptobenzothiazole, 2-mercaptobenzoxazole, 2-mercaptobenzimidazole, 2-mercapto-4(3H)-quinazoline, and β-mercaptonaphthalene.

Still Other examples of the cosensitizer include amino acid compounds (such as N-phenylglycine), organometallic compounds (such as tributyltin acetate) described in JP-B-48-42965, hydrogen donors described in JP-B-55-34414, sulfur compounds (such as trithiane) described in JP-A-6-308727, phosphorous compounds (such as diethyl phosphite) described in JP-A-6-250387, and Si—H and Ge—H compounds described in JP-A-6-191605.

[Other Components and the Like]

The gas separation membrane of the present invention may contain a variety of polymer compounds in order to adjust membrane physical properties. Examples of the polymer compounds include acrylic polymers, polyurethane resins, polyamide resins, polyester resins, epoxy resins, phenol resins, polycarbonate resins, polyvinyl butyral resins, polyvinyl formal resins, shelac, vinylic resins, acrylic resins, rubber-based resins, waxes, and other natural resins. These polymer compounds may be used alone or in combination of two or more kinds thereof.

Moreover, a nonionic surfactant, a cationic surfactant, an organic fluoro surfactant or the like may be added in order to adjust liquid physical properties.

Specific examples of the surfactant include anionic surfactants such as alkylbenzene sulfonates, alkyl naphthalene sulfonates, higher fatty acid salts, sulfonates of a higher fatty acid ester, ester sulfates of a higher alcohol ether, sulfonates of a higher alcohol ether, alkylcarboxylates of a higher alkylsulfone amide, and alkylphosphates; and nonionic surfactants such as polyoxyethylene alkyl ethers, polyoxyethylene alkyl phenyl ethers, polyoxyethylene fatty acid esters, sorbitan fatty acid esters, ethylene oxide adducts of acetylene glycol, ethylene oxide adducts of glycerin, and polyoxyethylene sorbitan fatty acid esters. Other examples include amphoteric surfactants such as alkyl betaine or amide betaine, silicone-based surfactants, fluorine-based surfactants and the like. The surfactant may be suitably selected from conventionally known surfactants and derivatives thereof.

Specific examples of polymer dispersants include polyvinyl pyrrolidone, polyvinyl alcohol, polyvinyl methylether, polyethylene oxide, polyethylene glycol, polypropylene glycol, and polyacryl amide. Among them, polyvinyl pyrrolidone is preferably used.

The conditions to form the gas separation membrane of the present invention are not particularly limited, but the temperature is preferably from −30° C. to 100° C., more preferably from −10° C. to 80° C., and particularly preferably from 5° C. to 50° C.

In the present invention, gas such as air or oxygen may coexist during the formation of membrane, but the formation is preferably performed under an inert gas atmosphere.

Moreover, an organic solvent may be added as a medium in the course of formation of the gas separation membrane of the present invention. Specifically, organic solvents to be used are not particularly limited, but examples include hydrocarbon-based organic solvents such as n-hexane and n-heptane; ester-based organic solvents such as methyl acetate, ethyl acetate, and butyl acetate; lower alcohols such as methanol, ethanol, n-propanol, isopropanol, n-butanol, isobutanol and tert-butanol; aliphatic ketones such as acetone, methyl ethyl ketone, methyl isobutyl ketone and diacetone alcohol; ether-based organic solvents such as ethylene glycol, diethylene glycol, triethylene glycol, glycerin, propylene glycol, ethylene glycol monomethyl or monoethyl ether, propylene glycol methyl ether, dipropylene glycol methyl ether, tripropylene glycol methyl ether, ethylene glycol phenyl ether, propylene glycol phenyl ether, diethylene glycol monomethyl or monoethyl ether, diethylene glycol monobutyl ether, triethylene glycol monomethyl or monoethyl ether, dibutyl ether and tetrahydrofuran; N-methylpyrrolidone, 2-pyrrolidone, dimethylformamide, dimethyl imidazolidinone, dimethyl sulfoxide, dimethyl acetamide and the like. These compounds may be used alone or in combination of two or more types.

The membrane thickness of the gas separation membrane of the present invention is preferably from 0.01 to 100 μm, more preferably from 0.1 to 2 μm.

[Method of Separating Gas Mixture]

The method of separating a gas mixture according to the present invention is a method of separating at least one acid gas from a mixed gas containing the at least one acid gas. The acid gas that can be separated by using the gas separation membrane or the composite membrane of the present invention is preferably carbon dioxide or hydrogen sulfide.

In the method of separating gas using the gas separation membrane of the present invention, the components of gas mixture of raw materials are not particularly restricted, but main components of the gas mixture are preferably carbon dioxide and methane or carbon dioxide and hydrogen. When the gas mixture is present together with an acid gas such as carbon dioxide or hydrogen sulfide, the method of separating gas using the gas separation membrane of the present invention exerts considerably superior performance, preferably exerts superior performance for separation of carbon dioxide and hydrocarbon such as methane, carbon dioxide and nitrogen, or carbon dioxide and hydrogen.

[Gas Separation Membrane Module and Gas Separation Apparatus]

The gas separation membrane of the present invention is preferably a composite membrane using a porous support in combination, and a gas separation membrane module using the same is preferred. Moreover, an apparatus for gas separation having means for separating and recovering or separating and purifying gas can be obtained by using the gas separation membrane, the composite membrane or the gas separation membrane module of the present invention.

The gas separation membrane of the present invention is preferably used in the form of a module. Examples of the module include spiral, hollow, pleat, tubular, and plate and frame type. Moreover, the polymer membrane of the present invention may be applied to an apparatus for separating and recovering gas using a membrane/absorption hybrid method in conjunction with an absorption solution, for example, as described in JP-A-2007-297605.

EXAMPLES

Hereinafter, the present invention will be described in more detail with reference to examples, but the present invention is not limited to these examples. In addition, "part" and "%" is based on mass, unless otherwise particularly described.

Synthesis Examples

Syntheses of Monomers (M-2) and (M-5)

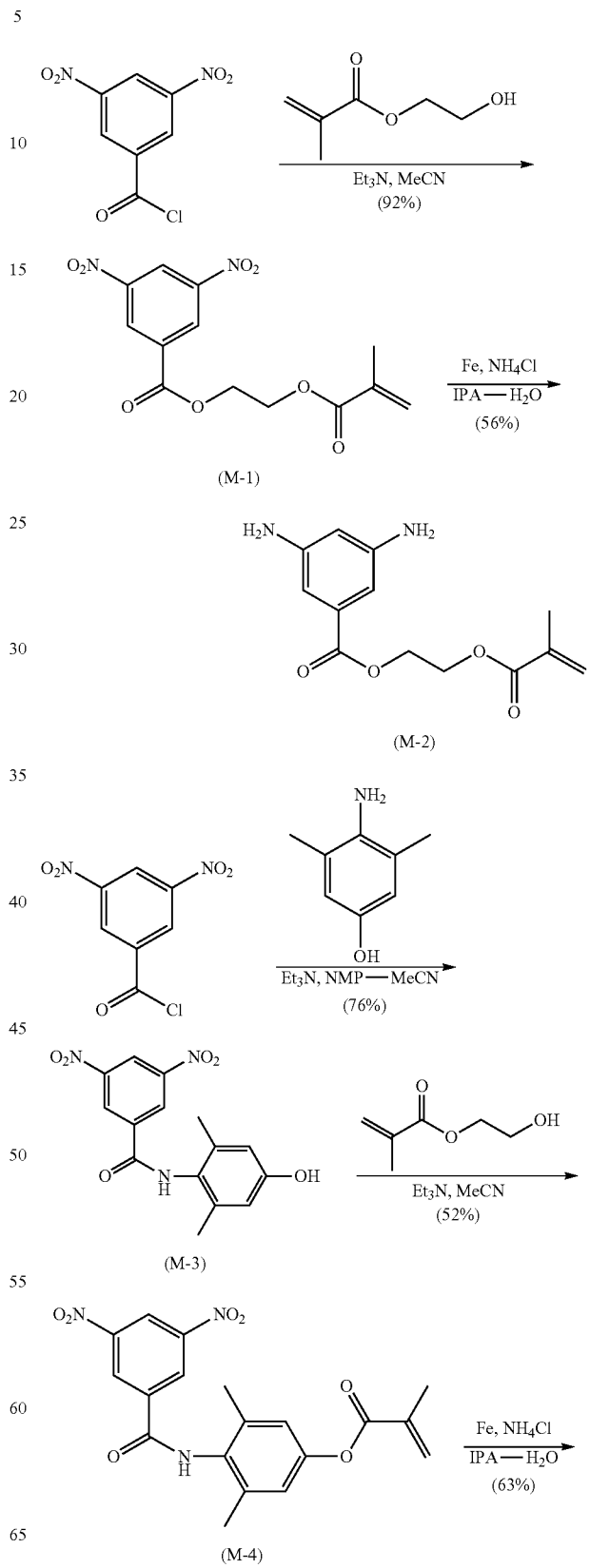

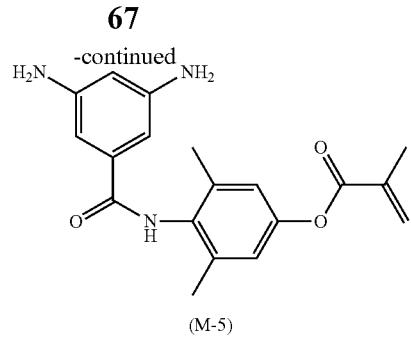

(M-5)

Herein, "Me" represents a methyl group, "Et" represents an ethyl group, "IPA" represents isopropyl alcohol, and "NMP" represents N-methylpyrrolidone.

Synthesis of Compound (M-1)

Into a 3 L three-necked flask, 130.14 g (1.0 mol) of 2-hydroxyethyl methacrylate (product number: 086-04385, manufactured by Wako Pure Chemical Industries, Ltd.) and 260 mL of acetonitrile were put, the resultant mixture was stirred under a nitrogen flow and under ice-cooling, and thereto, an acetonitrile solution (460 mL) of 230.56 g (1.0 mol) of 3,5-dinitrobenzoyl chloride (product number: D0825, manufactured by Tokyo Chemical Industry Co., Ltd.) was added. Further, 146.5 mL (1.05 mmol) of triethylamine (product number: 292-02656, manufactured by Wako Pure Chemical Industries, Ltd.) was added dropwise thereto over 30 minutes or more. After completion of the dropwise addition, the resultant mixture was stirred for 1 hour under ice-cooling, and then gradually heated to room temperature. Water was added to the resultant reaction mixture, produced crystals were filtered, and then collected crude crystals were washed with ion exchange water, and methanol, and thus 297.5 g of the compound (M-1) was obtained. (Yield: 92%). The compound (M-1) was used for the next reaction without further purification.

$^1$H-NMR (300 MHz) δ=9.25 (br.t, J=2.1 Hz, 1H), 9.17 (br.d, J=2.1 Hz, 2H), 6.15-6.17 (m, 1H), 5.65-5.62 (m, 1H), 4.50-4.62 (m, 2H), 4.70-4.80 (m, 2H), 1.96 (s, 3H).

Synthesis of Compound (M-2)

Into a 3 L three-necked flask, 307.5 g (5.51 mol) of reduced iron (product number: 096-00785, manufactured by Wako Pure Chemical Industries, Ltd.), 49.1 g (0.92 mol) of ammonium chloride (product number: 018-20985, manufactured by Wako Pure Chemical Industries, Ltd.), 1,230 mL of 2-propanol, and 250 mL of water were put, and the resultant mixture was heated to reflux with stirring. When heating to reflux was confirmed, 49 mL of glacial acetic acid was added thereto, and the resultant mixture was further heated to reflux with stirring for 5 minutes, and then 297.53 g (0.918 mol) of the compound (M-1) was carefully added thereto, and the resultant mixture was further heated to reflux with stirring for 2 hours. The resultant reaction mixture was cooled to near room temperature, and then 2 L of methanol was added thereto, an iron residue was removed by performing Celite filtration, and a filtrate was concentrated by a rotary evaporator. Ethyl acetate was added to the concentrate, and the resultant mixture was purified by silica gel column chromatography, and subjected to recrystallization from a hexane-ethyl acetate mixed solution, and thus 134.6 g of the compound (M-2) was obtained. (Yield: 56%).

$^1$H-NMR (300 MHz) δ=6.78 (br.d, J=2.1 Hz, 2H), 6.19 (br.t, J=2.1 Hz, 1H), 6.12-6.16 (m, 1H), 4.48-4.54 (m, 2H), 4.43-4.48 (m, 2H), 1.95 (s, 3H).

Synthesis of Compound (M-3)

Into a 500 mL three-necked flask, 13.72 g (0.10 mol) of 4-amino-3,5-xylenol (product number: A1860, manufactured by Tokyo Chemical Industry Co., Ltd.), 41 mL of N-methyl pyrrolidone, and 41 mL of acetonitrile were put, the resultant mixture was stirred under a nitrogen flow and under ice-cooling, and thereto, 14.7 mL (1.0 mol) of triethylamine (product number: 292-02656, manufactured by Wako Pure Chemical Industries, Ltd.) was added. Further, 30 mL of an acetonitrile solution of 23.06 g (0.10 mol) of 3,5-dinitrobenzoyl chloride (product number: D0825, manufactured by Tokyo Chemical Industry Co., Ltd.) was added dropwise thereto over 30 minutes or more. After completion of the dropwise addition, the resultant mixture was stirred for 1 hour under ice-cooling, and then gradually heated to room temperature. Water was added to the resultant reaction mixture, produced crystals were filtered, and then collected crude crystals were washed with ion exchange water, and acetonitrile-$H_2O$ (1:1), and thus 14.6 g of the compound (M-3) was obtained. (Yield: 44%). The compound (M-3) was used for the next reaction without further purification.

Synthesis of Compound (M-4)

Into a 500 mL three-necked flask, 9.5 g (0.029 mol) of the compound (M-3) and 180 mL of acetonitrile were put, the resultant mixture was stirred under a nitrogen flow and under ice-cooling, and thereto, 4.4 mL (0.032 mol) of triethylamine (product number: 292-02656, manufactured by Wako Pure Chemical Industries, Ltd.) was added. Further, an acetonitrile solution (30 mL) of 3.0 g (0.029 mol) of methacryloyl chloride (product number: 130-11742, manufactured by Tokyo Chemical Industry Co., Ltd.) was added dropwise thereto over 30 minutes or more. After completion of the dropwise addition, the resultant mixture was stirred for 1 hour under ice-cooling, and then gradually heated to room temperature. Water was added to the resultant reaction mixture, produced crystals were filtered, and then collected crude crystals were washed with ion exchange water, and acetonitrile-$H_2O$ (1:1), and thus 7.2 g of the compound (M-4) was obtained. (Yield: 52%). The compound (M-4) was used for the next reaction without further purification.

Synthesis of Monomer (M-5)

Into a 500 mL three-necked flask, 13.0 g (mol) of reduced iron (product number: 096-00785, manufactured by Wako Pure Chemical Industries, Ltd.), 1.3 g (mol) of ammonium chloride (product number: 018-20985, manufactured by Wako Pure Chemical Industries, Ltd.), 130 mL of 2-propanol, and 250 mL of water were put, and the resultant mixture was heated to reflux with stirring. When heating to reflux was confirmed, 1.3 mL of glacial acetic acid was added thereto, and the resultant mixture was further heated to reflux with stirring for 5 minutes, and then 13.0 g (mol) of the compound (M-4) was carefully added thereto, and the resultant mixture was further heated to reflux with stirring for 2 hours. The resultant reaction mixture was cooled to near room temperature, and then 0.5 L of ethyl acetate was added thereto, an iron residue was removed by performing Celite filtration, and a filtrate was concentrated by a rotary evaporator. Ethyl acetate was added to the concentrate, and the resultant mixture was purified by silica gel column chromatography, and subjected to recrystallization from a hexane-ethyl acetate mixed solution, and thus 7.01 g of the compound (M-5) was obtained. (Yield: 63%).

$^1$H-NMR (300 MHz) δ=9.35 (br.s, 1H), 6.91 (br. 2H), 6.35 (br.d, J=2.1 Hz, 2H), 6.26 (br.s, 1H), 5.99 (br, 1H), 5.89 (br, 1H), 4.92 (br.s, 4H), 2.16 (s, 6H), 2.00 (s, 3H).

Syntheses of Monomers (M-7) and (M-9)

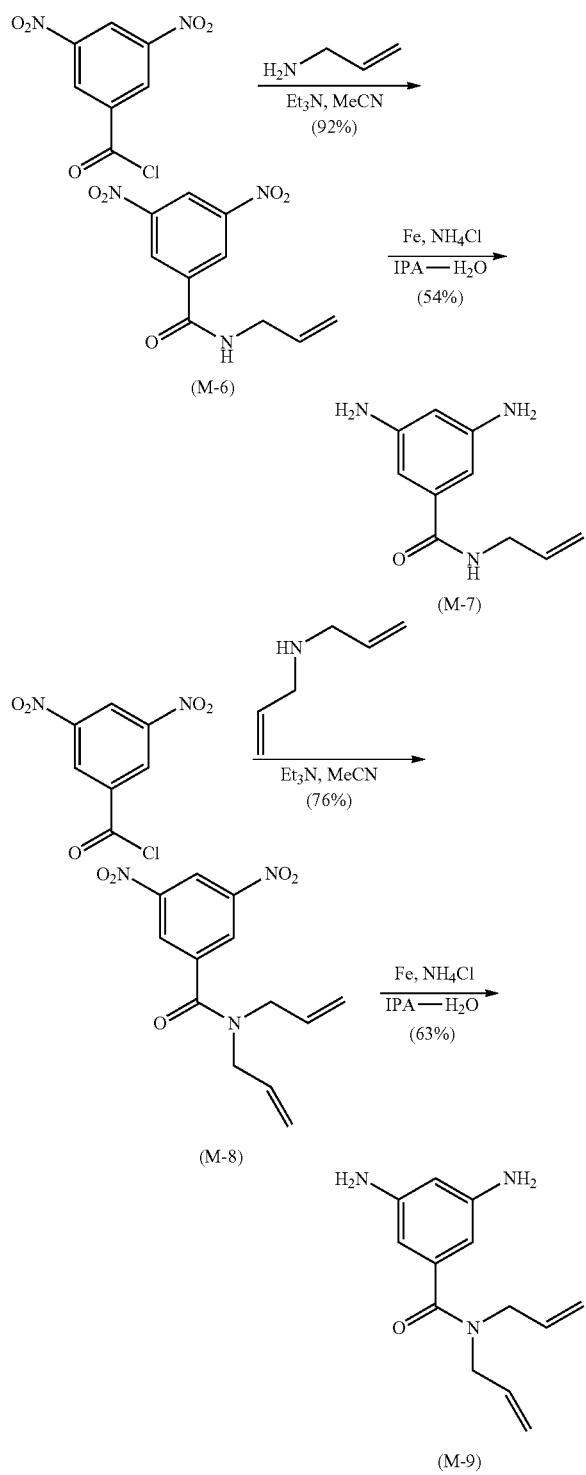

Synthesis of Compound (M-6)

Into a 3 L three-necked flask, 25.0 g (0.27 mol) of allylamine hydrochloride (product number: A0226, manufactured by Tokyo Chemical Industry Co., Ltd.) and 260 mL of acetonitrile were put, the resultant mixture was stirred under a nitrogen flow and under ice-cooling, and thereto, an acetonitrile solution (150 mL) of 61.6 g (0.27 mol) of 3,5-dinitrobenzoyl chloride (product number: D0825, manufactured by Tokyo Chemical Industry Co., Ltd.) was added. Further, 82 mL (0.59 mmol) of triethylamine (product number: 292-02656, manufactured by Wako Pure Chemical Industries, Ltd.) was added dropwise thereto over 30 minutes or more. After completion of the dropwise addition, the temperature was raised to room temperature, and stirring was still continued for 2 hours. Thereafter, water was added to the reaction mixture, and then an aqueous layer was extracted with ethyl acetate, and then the collected organic layers were concentrated using a rotary evaporator. The produced coarse crystals were washed by dispersion with hexane-ethyl acetate (5:1). Thus, 58.2 g of the compound (M-6) was obtained. (Yield: 92%). The compound (M-6) was used for the next reaction without further purification.

$^1$H-NMR (300 MHz, dmso-d6) δ=9.40 (br.t, J=5.6 Hz, 1H), 9.07 (br.d, J=2.1 Hz, 2H), 8.96 (t, J=2.1 Hz, 1H), 5.86-5.97 (m, 1H), 5.20-5.27 (m, 1H), 5.12-5.17 (m, 1H), 3.96-4.02 (m, 2H).

Synthesis of Compound (M-7)

Into a 2 L three-necked flask, 174 g (3.12 mol) of reduced iron (product number: 096-00785, manufactured by Wako Pure Chemical Industries, Ltd.), 17.4 g (0.33 mol) of ammonium chloride (product number: 018-20985, manufactured by Wako Pure Chemical Industries, Ltd.), 700 mL of 2-propanol, and 100 mL of water were put, and the resultant mixture was heated to reflux with stirring. When heating to reflux was confirmed, 18 mL of glacial acetic acid was added thereto, and the resultant mixture was further heated to reflux with stirring for 5 minutes, and then 58.2 g (0.25 mol) of the compound (M-6) was carefully added thereto, and the resultant mixture was further heated to reflux with stirring for 2 hours. The resultant reaction mixture was cooled to near room temperature, and then 2 L of methanol was added thereto, an iron residue was removed by performing Celite filtration, and a filtrate was concentrated by a rotary evaporator. Ethyl acetate was added to the concentrate, and the resultant mixture was purified by silica gel column chromatography, and subjected to recrystallization from a hexane-ethyl acetate mixed solution, and thus 23.6 g of the compound (M-7) was obtained. (Yield: 54%).

$^1$H-NMR (300 MHz, dmso-d6) δ=8.14 (br.t, J=5.6 Hz, 1H), 6.22 (br.d, J=2.1 Hz, 2H), 5.92-5.95 (m, 1H), 5.78-5.90 (m, 1H), 5.08-5.15 (m, 1H), 5.02-5.07 (m, 1H), 4.84 (br.s, 4H).

Synthesis of Compound (M-8)

Into a 1 L three-necked flask, 41.17 g (0.42 mol) of diallylamine (product number: D0069, manufactured by Tokyo Chemical Industry Co., Ltd.) and 260 mL of acetonitrile were put, the resultant mixture was stirred under a nitrogen flow and under ice-cooling, and thereto, an acetonitrile solution (200 mL) of 97.7 g (0.42 mol) of 3,5-dinitrobenzoyl chloride (product number: D0825, manufactured by Tokyo Chemical Industry Co., Ltd.) was added. Further, 65.0 ml (0.47 mmol) of triethylamine (product number: 292-02656, manufactured by Wako Pure Chemical Industries, Ltd.) was added dropwise thereto over 30 minutes or more. After completion of the dropwise addition, the resultant mixture was stirred for 1 hour under ice-cooling, and then gradually heated to room temperature. Thereafter, water was added to the reaction mixture, and then an aqueous layer was extracted with ethyl acetate, and then the collected organic layers were concentrated using a rotary evaporator. The produced coarse crystals were washed by dispersion with hexane-ethyl acetate (5:1). Thus, 86.0 g of the compound (M-8) was obtained. (Yield: 70%). The compound (M-8) was used for the next reaction without further purification.

$^1$H-NMR (300 MHz, CDCl$_3$) δ=9.69 (br.t, J=2.1 Hz, 1H), 8.66 (br.d, J=2.1 Hz, 2H), 5.70-6.0 (m, 2H), 5.25-5.45 (m, 2H), 5.27 (br.d, 2H, J=17.4 Hz), 4.18 (br.s, 2H), 3.85 (br.s, 2H).

Synthesis of Compound (M-9)

Into a 2 L three-necked flask, 166 g (2.97 mol) of reduced iron (product number: 096-00785, manufactured by Wako Pure Chemical Industries, Ltd.), 16.6 g (0.31 mol) of ammonium chloride (product number: 018-20985, manufactured by Wako Pure Chemical Industries, Ltd.), 1,200 mL of 2-propanol, and 200 mL of water were put, and the resultant mixture was heated to reflux with stirring. When heating to reflux was confirmed, 49 mL of glacial acetic acid was added thereto, and the resultant mixture was further heated to reflux with stirring for 5 minutes, and then 83.0 g (0.28 mol) of the compound (M-8) was carefully added thereto, and the resultant mixture was further heated to reflux with stirring for 2 hours. The resultant reaction mixture was cooled to near room temperature, and then 2 L of methanol was added thereto, an iron residue was removed by performing Celite filtration, and a filtrate was concentrated by a rotary evaporator. Ethyl acetate was added to the concentrate, and the resultant mixture was purified by silica gel column chromatography, and subjected to recrystallization from a hexane-ethyl acetate mixed solution, and thus 41.5 g of the compound (M-9) was obtained. (Yield: 63%).

$^1$H-NMR (300 MHz, CDCl$_3$) δ=6.12 (br.d, J=2.1 Hz, 2H), 6.02 (br.t, J=2.1 Hz, 1H), 5.6-5.9 (m, 2H), 5.15-5.24 (m, 3H), 5.14 (br, 1H), 4.08 (br.s, 2H), 3.87 (br.s, 2H), 3.63 (s, 4H).

"Me" represents a methyl group, "Et" represents an ethyl group, and "IPA" represents isopropyl alcohol.

Synthesis Example

Synthesis of Polymer (P-1)

Synthesis of Polymer (P-1)

Into a 1 L three-necked flask, 123 mL of N-methylpyrrolidone and 54.97 g (0.124 mol) of 6FDA (product number: manufactured by Tokyo Chemical Industry Co., Ltd.) were put to allow dissolution at 40° C., the resultant mixture was stirred under a nitrogen flow, and thereto, 84.0 mL of N-methylpyrrolidone solution containing 4.098 g (0.0248 mol) of 2,3,5,6-tetramethylphenylenediamine (product number: T1457, manufactured by Tokyo Chemical Industry Co., Ltd.), and 15.138 g (0.0992 mol) of DABA was added dropwise thereto over 30 minutes while keeping the inside of the system at 40° C. The resultant reaction mixture was stirred at 40° C. for 2.5 hours, and then 2.94 g (0.037 mol) of pyridine (product number: manufactured by Wako Pure Chemical Industries, Ltd.) and 31.58 g (0.31 mol) of acetic anhydride (product number: manufactured by Wako Pure Chemical Industries, Ltd.) were added thereto, respectively, and the resultant mixture was further stirred at 80° C. for 3 hours. Then, 676.6 mL of acetone was added to the reaction mixture, and the reaction mixture was diluted. Into a 5 L stainless steel container, 1.15 L of methanol and 230 mL of acetone were put, the resultant mixture was stirred, and thereto, the acetone diluted solution of the reaction mixture was added dropwise. The obtained polymer crystals were subjected to suction filtration, and air blow drying at 60° C., and thus 50.5 g of the polymer (P-1) was obtained.

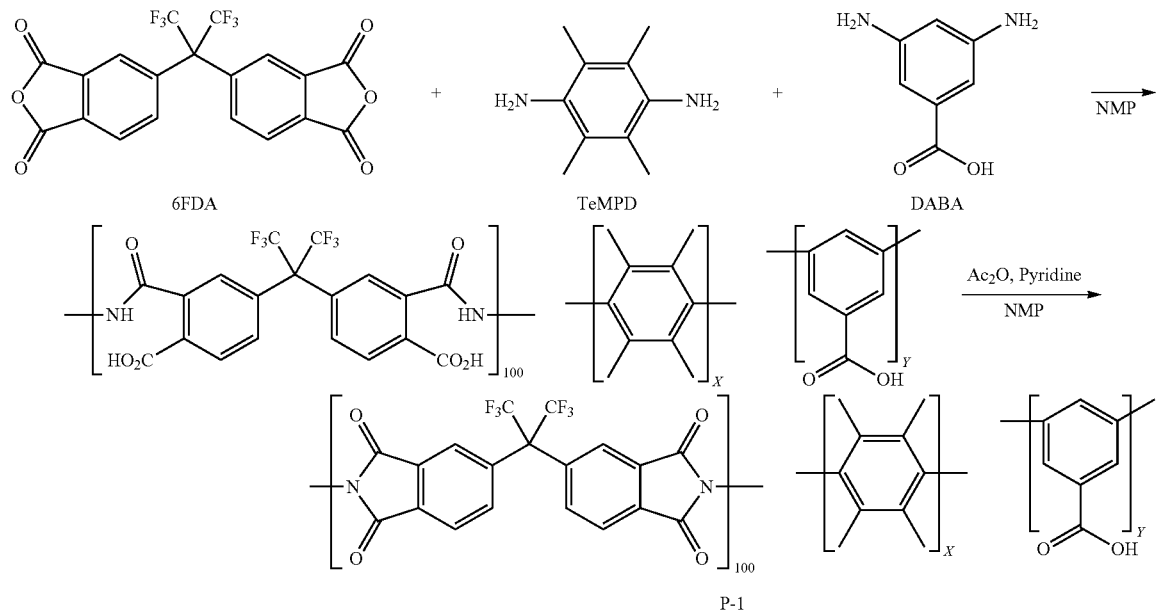

X = 20, Y = 80

Synthesis of Polymer (P-2)

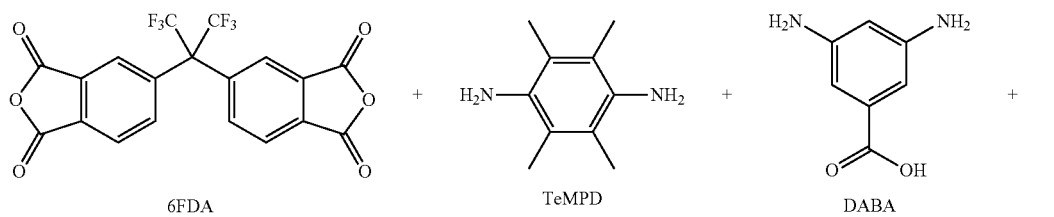

6FDA  TeMPD  DABA

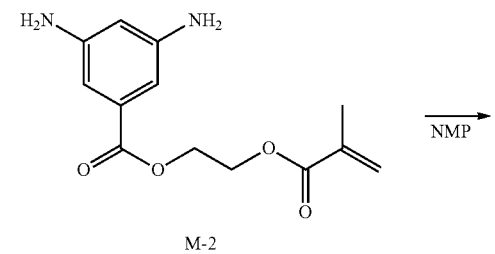

M-2

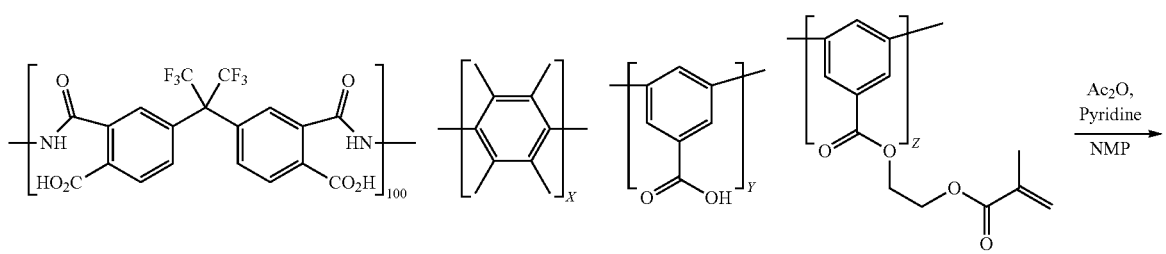

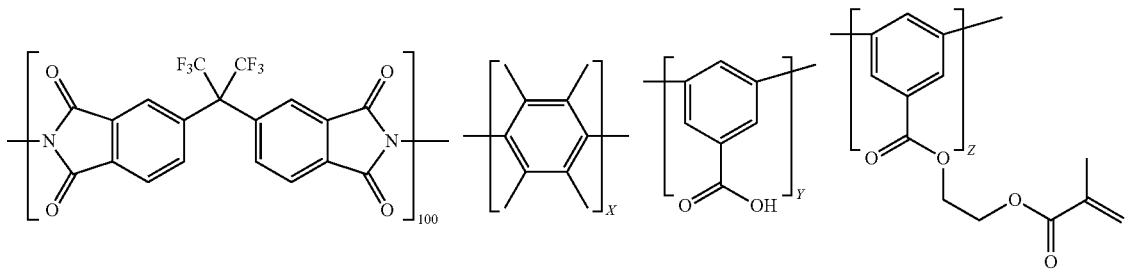

P-2

X = 20, Y = 70, Z = 10

Synthesis of Polymer (P-2)

Into a 1 L three-necked flask, 123 mL of N-methylpyrrolidone and 54.97 g (0.124 mol) of 6FDA (product number: H0771, manufactured by Tokyo Chemical Industry Co., Ltd.) were put to allow dissolution at 40° C., the resultant mixture was stirred under a nitrogen flow, and thereto, 87.2 mL of N-methylpyrrolidone solution containing 4.098 g (0.0248 mol) of 2,3,5,6-tetramethylphenylenediamine (product number: T1457, manufactured by Tokyo Chemical Industry Co., Ltd.), 13.12 g (0.0868 mol) of DABA, 3.277 g (0.0124 mol) of the monomer (M-2) and Irganox 1010 (0.132 g) was added dropwise over 30 minutes while keeping the inside of the system at 40° C. The resultant reaction mixture was stirred at 40° C. for 2.5 hours, and then 2.94 g (0.037 mol) of pyridine (product number: 166-22575, manufactured by Wako Pure Chemical Industries, Ltd.) and 31.58 g (0.31 mol) of acetic anhydride (product number: 018-00286, manufactured by Wako Pure Chemical Industries, Ltd.) were added thereto, respectively, and the resultant mixture was further stirred at 80° C. for 3 hours. Then, 676.6 mL of acetone was added to the reaction mixture, and the reaction mixture was diluted. Into a 5 L stainless steel container, 1.15 L of methanol and 230 mL of acetone were put, the resultant mixture was stirred, and thereto, the acetone diluted solution of the reaction mixture was added dropwise. A precipitated polymer was subjected to suction filtration, and air blow drying at 60° C., and thus 54.7 g of the polymer (P-2) was obtained.

Synthesis of Polymer (P-3)

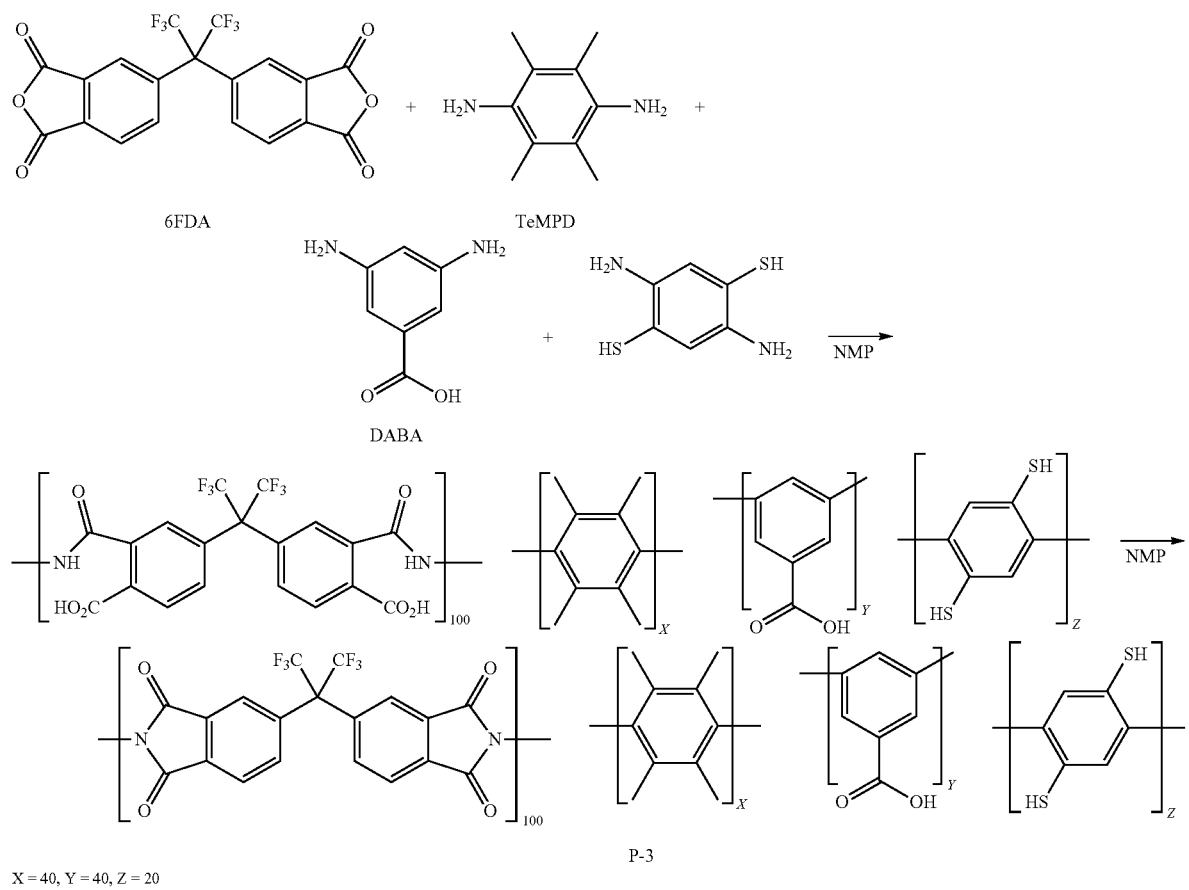

X = 40, Y = 40, Z = 20

Synthesis of Polymer (P-3)

Into a 1 L three-necked flask, 123 mL of N-methylpyrrolidone and 33.318 g (0.075 mol) of 6FDA (product number: H0771, manufactured by Tokyo Chemical Industry Co., Ltd.) were put to allow dissolution at 40° C., the resultant mixture was stirred under a nitrogen flow, and thereto, 87.2 mL of N-methylpyrrolidone solution containing 4.9275 g (0.03 mol) of 2,3,5,6-tetramethylphenylenediamine (product number: T1457, manufactured by Tokyo Chemical Industry Co., Ltd.), 4.5645 g (0.03 mol) of DABA, 3.677 g (0.015 mol) of 2,5-dimercapto-1,4-phenylenediamine dihydrochloride (product number: D2022, manufactured by Tokyo Chemical Industry Co., Ltd.) and 1.1085 g (0.015 mol) of lithium carbonate was added dropwise over 30 minutes while keeping the inside of the system at 40° C. The reaction liquid was stirred at room temperature ° C. for 2.5 hours, and then a Dean-Stark water separator was installed, and thereto, 123 ml of each of toluene and N-methylpyrrolidone was added and further the temperature was raised to 180° C., and the reaction liquid was stirred for 2.5 hours. After completion of the reaction, the resultant reaction mixture was cooled to near room temperature, and then 676.6 mL of acetone was added thereto and diluted. Into a 5 L stainless steel container, 1.15 L of methanol and 1.15 L of water were put, the resultant mixture was stirred, and thereto, the acetone diluted solution of the reaction mixture was added dropwise. A precipitated polymer was subjected to suction filtration, and air blow drying at 60° C., and thus 33.2 g of the polymer (P-3) was obtained.

Synthesis of Polymer (P-4)

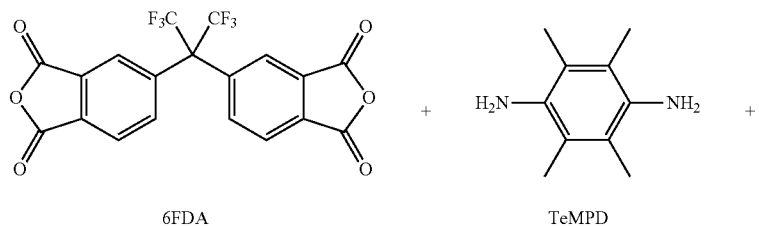

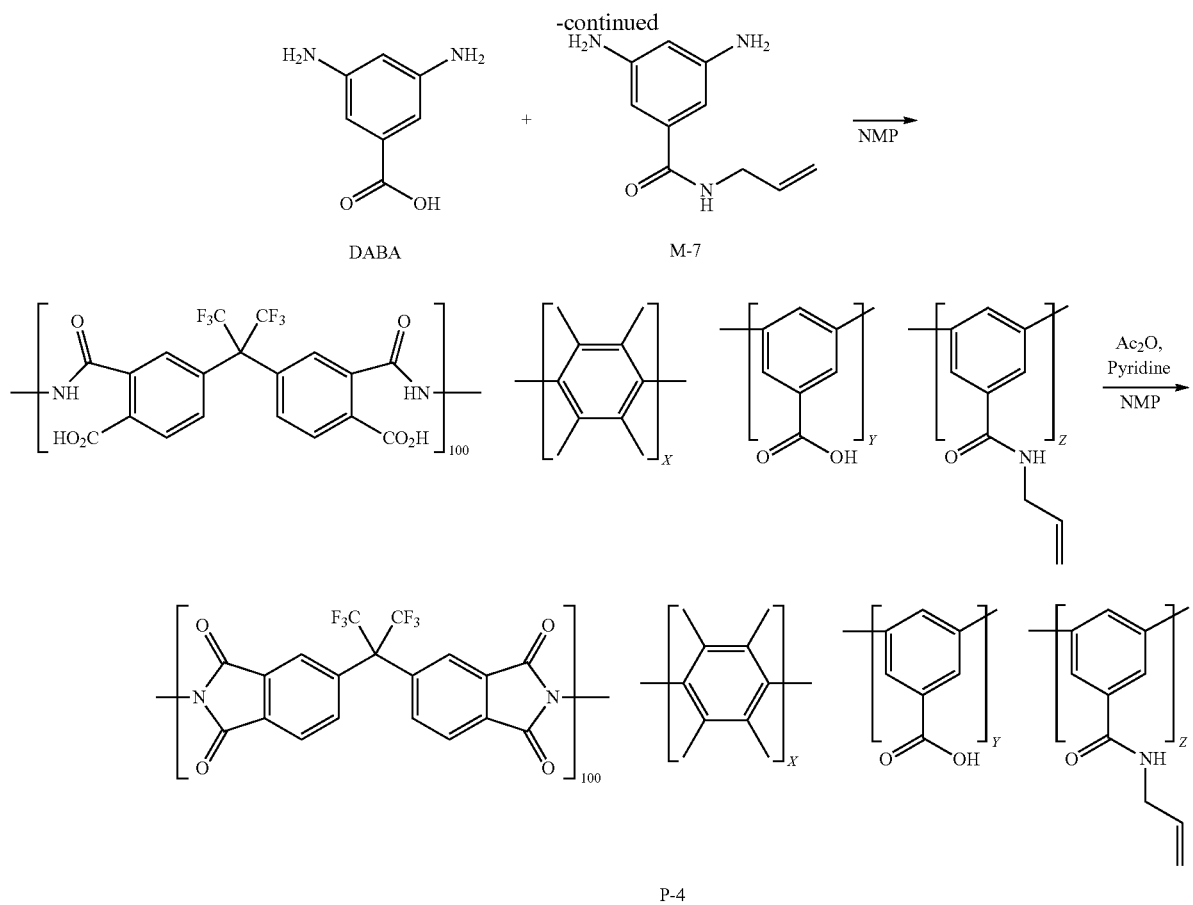

P-4

Synthesis of Polymer (P-4)

Into a 1 L three-necked flask, 397 mL of N-methylpyrrolidone and 166.59 g (0.375 mol) of 6FDA (product number: H0771, manufactured by Tokyo Chemical Industry Co., Ltd.) were put to allow dissolution at 40° C., the resultant mixture was stirred under a nitrogen flow, and thereto, 324 mL of N-methylpyrrolidone solution containing 12.319 g (0.075 mol) of 2,3,5,6-tetramethylphenylenediamine (product number: T1457, manufactured by Tokyo Chemical Industry Co., Ltd.), 28.53 g (0.187 mol) of DABA and 19.73 g (0.112 mol) of the monomer (M-7) was added dropwise over 30 minutes while keeping the inside of the system at 40° C. The resultant reaction mixture was stirred at 40° C. for 2.5 hours, and then 8.9 g (0.113 mol) of pyridine (product number: 166-22575, manufactured by Wako Pure Chemical Industries, Ltd.) and 114.9 g (1.13 mol) of acetic anhydride (product number: 018-00286, manufactured by Wako Pure Chemical Industries, Ltd.) were added thereto, respectively, and the resultant mixture was further stirred at 80° C. for 3 hours. Then, 1.5 L mL of acetone and 50 mL of water were added to the reaction mixture, and the reaction mixture was diluted. Into a 20 L stainless steel container, 5 L of methanol and 230 mL of acetone were put, the resultant mixture was stirred, and thereto, the acetone diluted solution of the reaction mixture was added dropwise. A precipitated polymer was subjected to suction filtration, and air blow drying at 60° C., and thus 115 g of the polymer (P-4) was obtained.

Synthesis of Polymer (P-5)

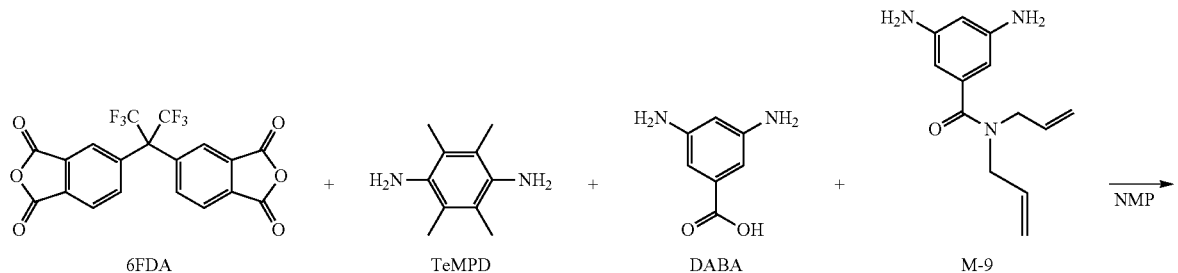

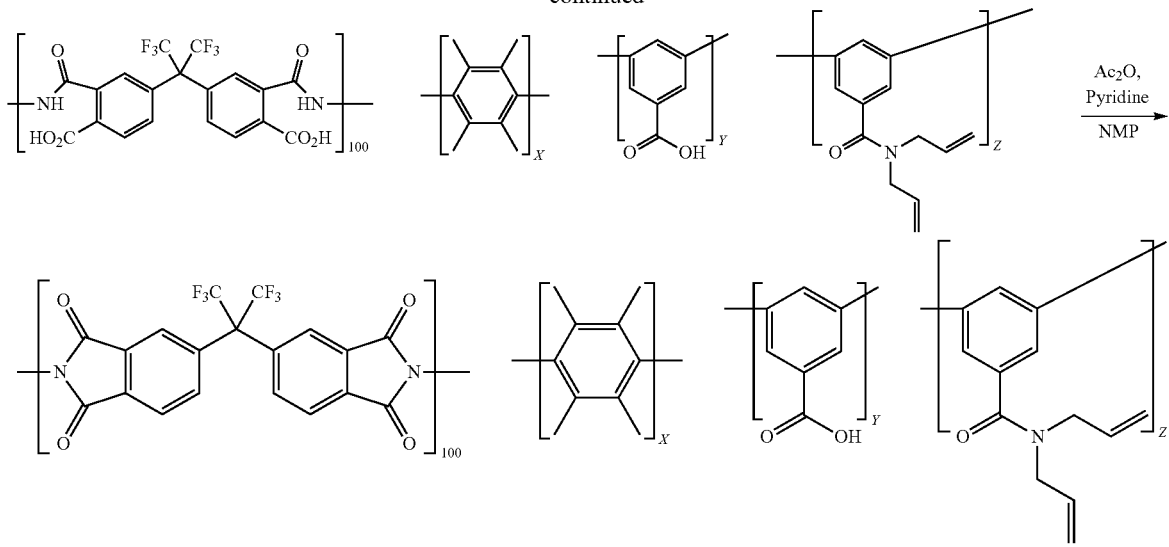

P-5

X = 20, Y = 50, Z = 30

Synthesis of Polymer (P-5)

Into a 1 L three-necked flask, 397 mL of N-methylpyrrolidone and 166.59 g (0.375 mol) of 6FDA (product number: H0771, manufactured by Tokyo Chemical Industry Co., Ltd.) were put to allow dissolution at 40° C., the resultant mixture was stirred under a nitrogen flow, and thereto, 324 mL of N-methylpyrrolidone solution containing 12.319 g (0.075 mol) of 2,3,5,6-tetramethylphenylenediamine (product number: T1457, manufactured by Tokyo Chemical Industry Co., Ltd.), 28.53 g (0.187 mol) of DABA and 26.02 g (0.112 mol) of the monomer (M-9) was added dropwise over 30 minutes while keeping the inside of the system at 40° C. The resultant reaction mixture was stirred at 40° C. for 2.5 hours, and then 8.9 g (0.113 mol) of pyridine (product number: 166-22575, manufactured by Wako Pure Chemical Industries, Ltd.) and 114.9 g (1.13 mol) of acetic anhydride (product number: 018-00286, manufactured by Wako Pure Chemical Industries, Ltd.) were added thereto, respectively, and the resultant mixture was further stirred at 80° C. for 3 hours. Then, 1.5 L mL of acetone and 50 mL of water were added to the reaction mixture, and the reaction mixture was diluted. Into a 20 L stainless steel container, 5 L of methanol and 230 mL of acetone were put, the resultant mixture was stirred, and thereto, the acetone diluted solution of the reaction mixture was added dropwise. A precipitated polymer was subjected to suction filtration, and air blow drying at 60° C., and thus 120 g of the polymer (P-5) was obtained.

Synthesis of Polymer (P-22)

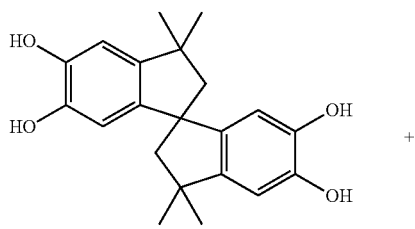 +

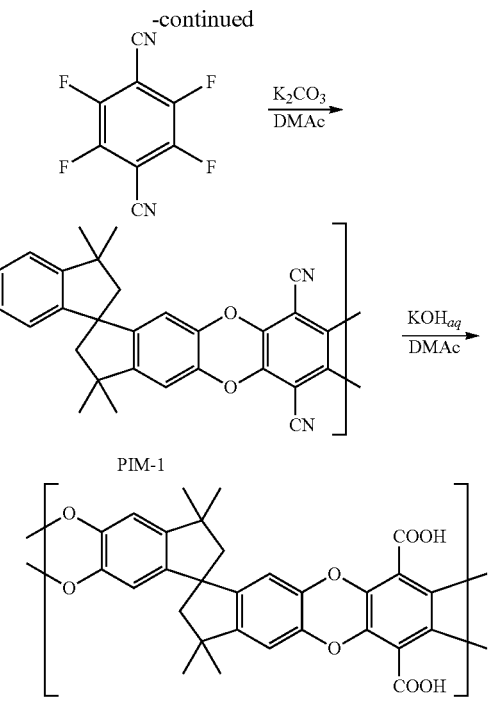

DMAC: N,N-dimethyl acetamide

Into a 1 L three-necked flask, 340 mL of N,N-dimethyl acetamide, 17.222 g (0.0506 mol) of tetrahydroxy tetramethyl indane (product number: T1737, manufactured by Tokyo Chemical Industry Co., Ltd.), 10.1228 g (0.051 mol) of 2,3,5,6-tetrafluoro-1,4-terephthalonitrile (product number: T1050, manufactured by Tokyo Chemical Industry Co., Ltd.), and 55.26 g (0.4 mol) of potassium carbonate (product number: 58010-17 manufactured by KANTO CHEMICAL CO., INC.) were put, and the resultant mixture was stirred at room temperature 120° C. for 24 hours. Thereafter, water was added to the reaction liquid, and then a precipitated polymer was collected by suction filtration, and the obtained polymer was washed with water, and methanol, and thus 18.2 g of polymer (PIM-1) was obtained.

Into a 1 L three-necked flask, 340 mL of N,N-dimethyl acetamide, polymer (PIM-1) and 100 mL of 1N potassium hydroxide aqueous solution were added, the resultant mixture was heated and stirred at 100° C. until it became a homogeneous solution. After completion of the reaction, the resultant reaction liquid was diluted with methanol and water added thereto, and then poured into concentrated hydrochloric acid-ice water, and then a precipitated polymer was collected by filtration, and the obtained polymer was washed with water, and methanol, and thus 11.1 g of polymer P-22 was obtained.

Example 1 and Comparative Example 1

In a brown vial container of 50 mL, 0.6 g of polymer (P-1) and 8.6 g of tetrahydrofuran were mixed and stirred for 30 minutes, and thereto, 38 mL of tetrahydrofuran solution containing 0.0568 g of crosslinking agent aminopropyltrimethoxysilane (R-6) was added, and the resultant mixture was further stirred for 30 minutes. On a 10 cm-square clean glass plate, a polyacrylonitrile porous membrane (manufactured by GMT Membrantechnik GmbH, Germany) was put to stand, and then the above-described polymer liquid was thinly casted on the porous membrane surface using an applicator, and then covered with a lid made of polypropylene, and left to stand overnight, and then dried at 70° C. for 3 hours using an air-blow dryer (composite film 101). The thickness of the polymer (P-1) layer was about 0.3 µm, and the thickness of the polyacrylonitrile porous membrane, including a nonwoven fabric, was about 170 µm.

In a brown vial container of 50 mL, 0.6 g of polymer (P-2) and 8.6 g of methyethyl ketone were mixed and stirred for 30 minutes, and thereto, 38 mL of tetrahydrofuran solution of 0.0204 g of crosslinking agent mercaptopropyltrimethoxysilane (R-11) and 0.0012 g of a photo-radical-acid generating agent 2-phenyl-2-(p-toluene sulfonyloxy)acetophenone (product number: P1410, manufactured by Tokyo Chemical Industry Co., Ltd.) was added, and the resultant mixture was further stirred for 30 minutes. On a 10 cm square clean glass plate, a polyacrylonitrile porous membrane (manufactured by GMT Membrantechnik GmbH) was left to stand, the polymer liquid was thinly cast on a surface of the porous support membrane using an applicator, and the resultant material was exposed at 63 mW for 30 seconds using light curing apparatus (TCT1000B-28HE) manufactured by Sen Lights Corporation. Thereafter, the resultant material was dried at 70° C. for 3 hours using an air-blow dryer, and thus composite film 102 was obtained. The thickness of the polymer (P-2) layer was about 0.2 µm, and the thickness of the polyacrylonitrile porous membrane, including a nonwoven fabric, was about 180 µm.

A composite membrane 103 was produced in a manner similar to the production of the composite membrane 102 except that P-3 was used in place of P-2 and the crosslinking agent was changed to (R-4).

Composite membranes were produced in a manner similar to the production of the composite membrane 103 except that the polymer, the crosslinking agent and the porous support membrane were changed as shown in Table 1.

<Polymer Described in U.S. Pat. No. 7,247,191 B2>

Into a 1 L three-necked flask, 100 mL of N-methylpyrrolidone and 12.0 g (0.027 mol) of 6FDA (product number: H0711, manufactured by Tokyo Chemical Industry Co., Ltd.) were put to allow dissolution at 40° C., the resultant mixture was stirred under a nitrogen flow, and thereto, 65 mL of N-methylpyrrolidone solution containing 3.25 g (0.0216 mol) of mesitylenediamine (product number: T1275, manufactured by Tokyo Chemical Industry Co., Ltd.) and 0.82 g (0.0054 mol) of 3,5-diaminobenzoic acid (product number: D0294, manufactured by Tokyo Chemical Industry Co., Ltd.) were added dropwise thereto over 30 minutes while keeping the inside of the system at 40° C. The resultant reaction mixture was stirred at 40° C. for 2.5 hours, and then 0.64 g (0.0081 mol) of pyridine (product number: 166-22575, manufactured by Wako Pure Chemical Industries, Ltd.) and 6.89 g (0.068 mol) of acetic anhydride (product number: 018-00286, manufactured by Wako Pure Chemical Industries, Ltd.) were added thereto, respectively, and the resultant mixture was further stirred at 80° C. for 3 hours. Then, 150 mL of acetone was added to the reaction mixture, and the reaction mixture was diluted. Into a 5 L stainless steel container, 1.5 L of methanol was put and stirred, and thereto, the acetone diluted solution of the reaction mixture was added dropwise. The obtained polymer crystals were subjected to suction filtration, and air blow drying at 60° C., and thus 8.3 g of polymer (A) was obtained. To this polymer (A), ethylene glycol was added in an amount equivalent to 3,5-diaminobenzoic acid, the polymer liquid was casted on each porous support membrane of polyacrylonitrile (PAN), polysulfone (Psf) and polyphenylene oxide (PPO) using an applicator in a manner similar to the operations for the sample 101, in a manner similar to the method described in U.S. Pat. No. 7,247,191 B2, and thus crosslinked composite membranes c11, c12 and c13 were produced.

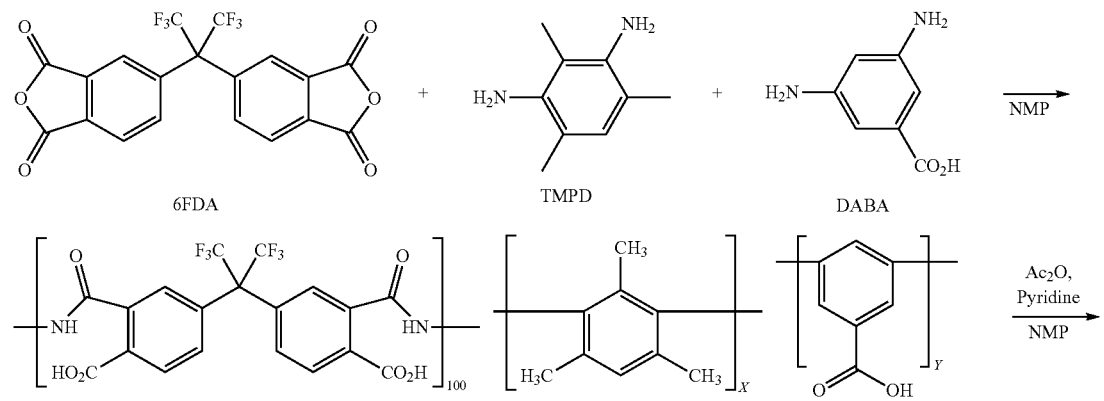

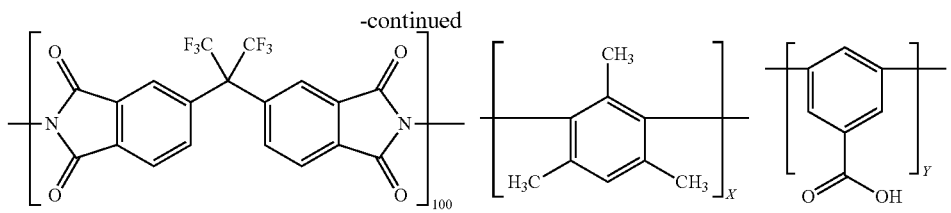

Polymer described in U.S. Pat. No. 7,247,191 B2

X = 60, Y = 40

With reference to European Polymer Journal, Vol. 33, No. 10-12, 1717-1721 (1997), a 6FDA/M-2 photo-curable-polyphenylene oxide (PPO) composite membrane c14 was produced.

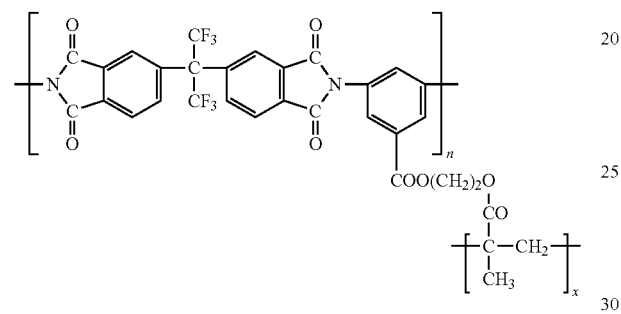

Polymer described in European Polymer Journal, 1997, 33, 1717

<Polymer Described in US 2010/0326273 A1>

A cellulose-based crosslinked organic-inorganic hybrid membrane c15 was produced in the same manner as the method described in US2010/0326273A1.

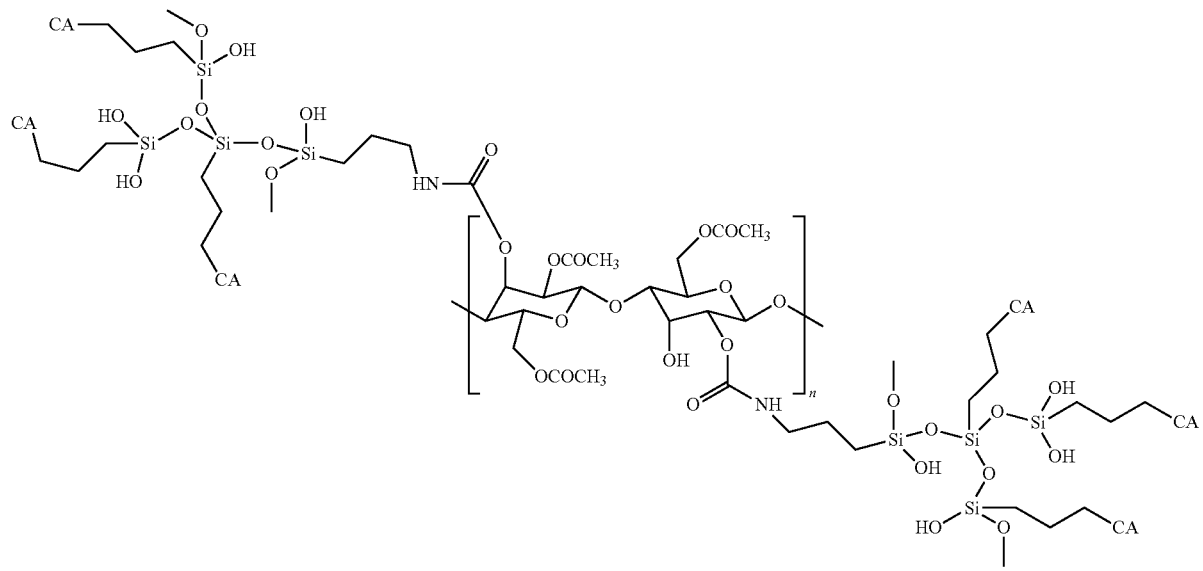

Polymer described in US 2010/0326273 A1

<Polymer Described in Polymer Bulletin>

A hyper-branched polyimide crosslinked organic-inorganic hybrid membrane c16 was produced in the same manner as the method described in Polymer Bulletin, 2005, 53, 139-146.

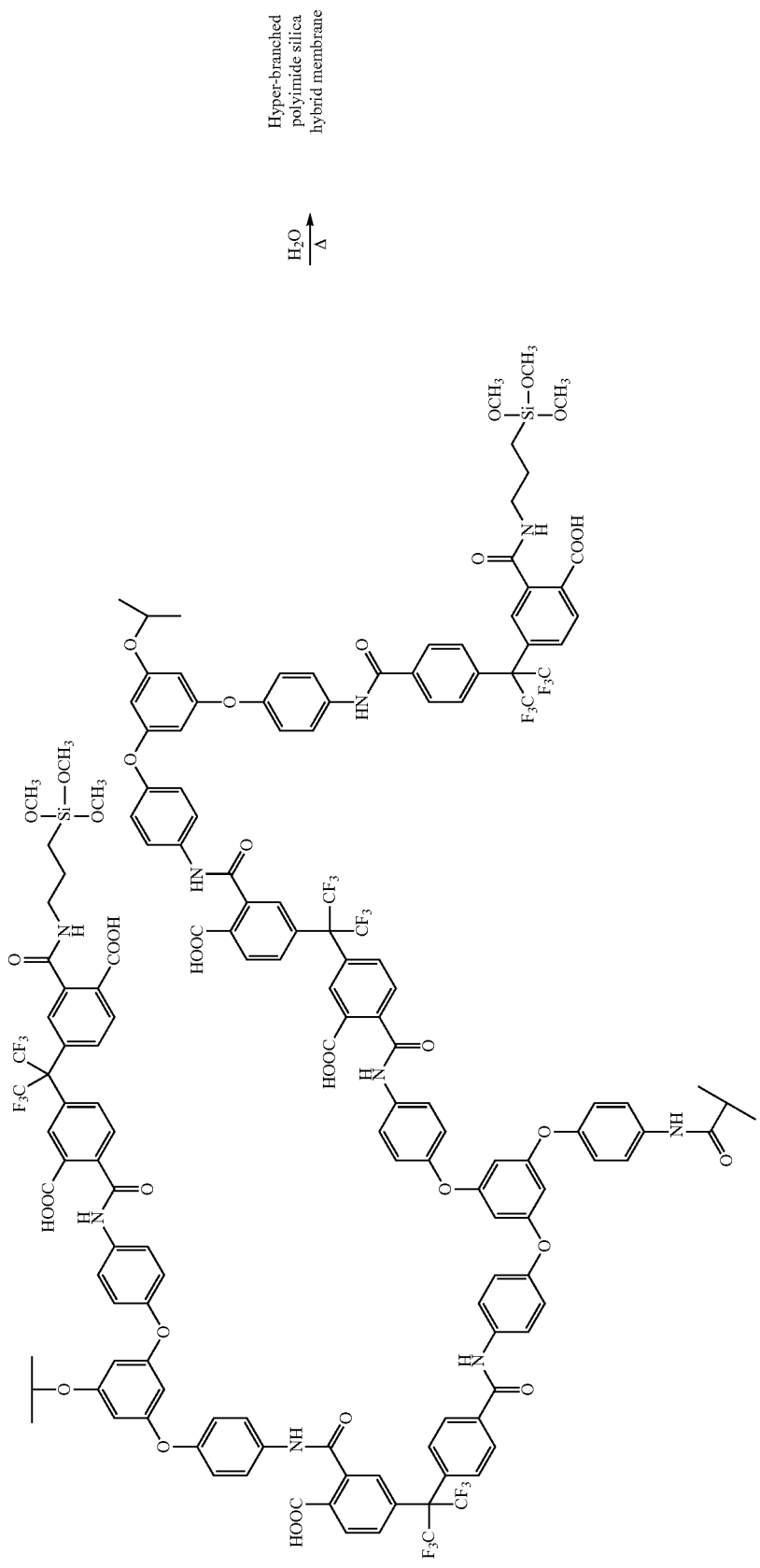
Polymer described in Polymer Bulletin, 2005, 53, 139-146

A 6FDA polyimide composite membrane c17 having oligomer silsesquioxane at the side chain thereof was produced with reference to the specification of U.S. Pat. No. 7,619,042.

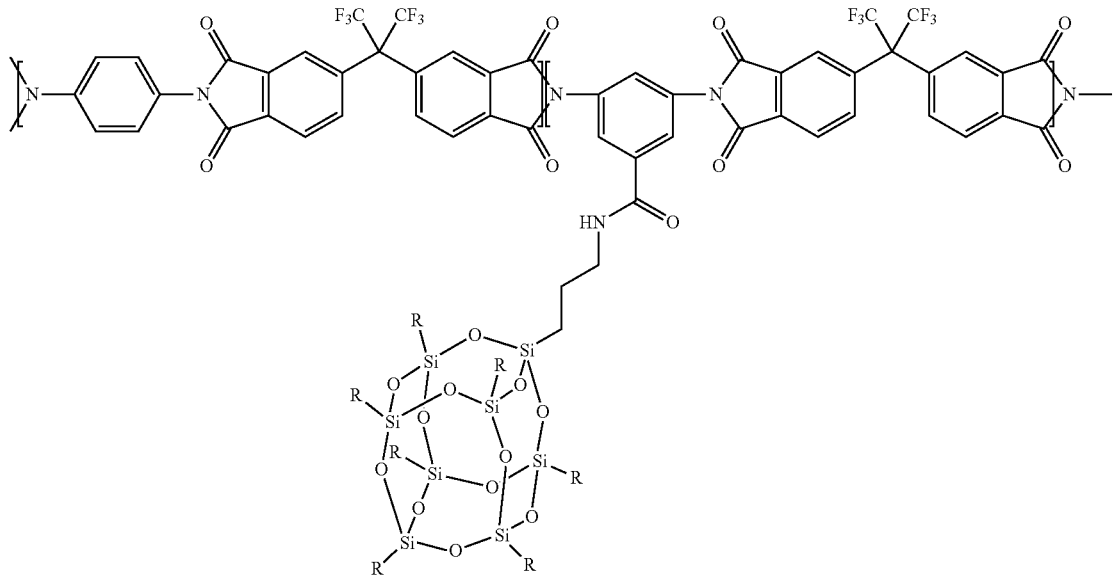

A 6FDA-6FpDA-DABA polyimide composite membrane c18 was produced with reference to Journal of Membrane Science, 2002, 202, 97.

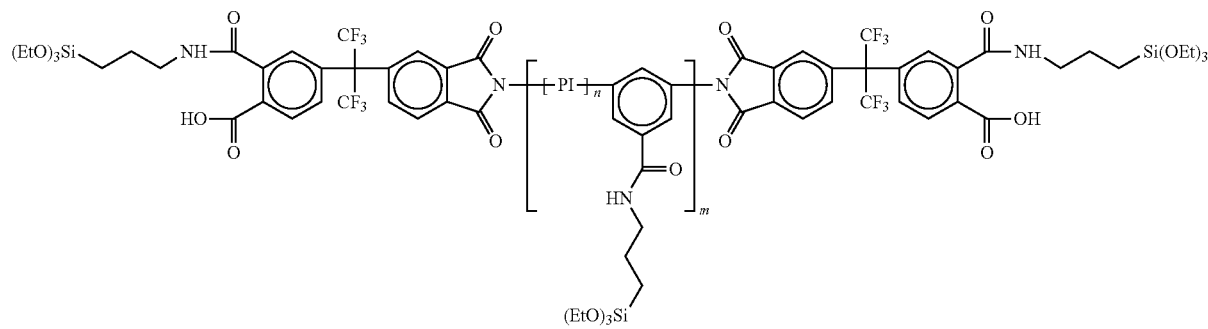

(Measurement of Gas Permeability)

Using a stainless membrane cell for a high-pressure measurement (manufactured by DENISSEN), and using a mixed gas (1:1) consisting of carbon dioxide ($CO_2$) and methane ($CH_4$) under the condition of 40° C., and adjusting a pressure at the gas supply side to the total pressure of 40 atmospheric pressure, gas permeability of the obtained composite membrane was measured in terms of each of $CO_2$ and $CH_4$. Gas permeability of the membranes was compared by calculating gas permeability (permeance) by a TCD detecting gas chromatography. A unit of the gas transmission rate (permeance) was expressed in terms of a GPU unit (1 GPU=$1\times10^{-6}$ cm$^3$ (STP)/(s·cm$^2$·cmHg)).

(Bending Test [Membrane-Forming Competence Test])

The gas separation membrane according to the present invention is desirably used as a package referred to as a module or an element in which the membrane is packed. When the gas separation membrane is used as the module, the membranes are packed with high density in order to increase a membrane surface area, and therefore packed by bending the membranes in a spiral shape in a flat sheet membrane. Therefore, sufficient bending strength should be provided with the membrane. In order to confirm the performance, operations of bending each composite membrane at 180 degrees and unbending the membrane were repeated by 50 times, and then whether or not measurement of the gas permeability was allowed was confirmed.

A: Permeability was measurable without any problem.

B: Permeability was not measurable.

The results of the gas permeability and the bending test are shown in Table 1.

TABLE 1
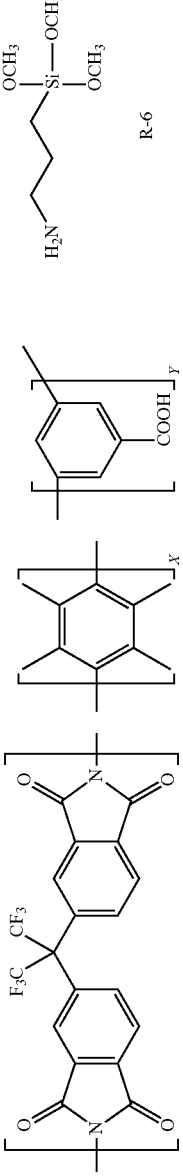

TABLE 1-continued

| | | | | |
|---|---|---|---|---|
| 103 | PAN | [polyimide structure with CF3 groups]100 / [benzene X] / [benzene with CO2H]y / [benzene with SH, HS]z P-3 | Vinyltrimethoxysilane R-4 | |
| 104 | PAN | P-3 | Vinyltrimethoxysilane / Tetramethoxysilane R-4, R-1 | |

TABLE 1-continued

| Sample No. | | | | |
|---|---|---|---|---|
| 105 | PAN | P-3 | 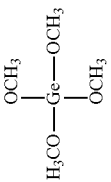 Vinyltrimethoxysilane | |
| | | | H₃CO—Ge—OCH₃ with OCH₃ groups<br>Tetramethoxygelmanium | |
| | | | R-4, R-23 | |
| 106 | PAN | P-3 | 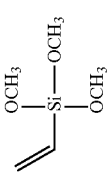 Vinyltrimethoxysilane<br>R-4 | |

| Sample No. | Crosslinking temperature/Time | CO₂ permeability (GPU) | CO₂/CH₄ separation selectivity | Bending test (Membrane-forming competence) |
|---|---|---|---|---|
| 101 | Drying: 70° C./3 h | 69 | 38 | A |
| 102 | Drying: 70° C./3 h | 71 | 38 | A |
| 103 | Drying: 70° C./3 h | 71 | 37 | A |
| 104 | Room temperature/1 min | 105 | 37 | A |
| 105 | Drying: 70° C./3 h | 89 | 36 | A |
| 106 | Drying: 70° C./3 h | 70 | 39 | A |

| Sample No. | Supporting membrane | Polymer | Crosslinking agent |
|---|---|---|---|
| 107 | PSf | P-3 | <br>R-9 |

TABLE 1-continued
| | | | |
|---|---|---|---|
| 108 | PPO | P-3  |  Vinyltrimethoxysilane R-4 |
| 109 | PTFE | |  R-11 |
| 110 | PTFE | P-22  |  Vinyltrimethoxysilane  Tetramethoxysilane R-4, R-1 |

TABLE 1-continued

| | | | |
|---|---|---|---|
| 111 | PAN | [structure with COOH, carboxylate-NH₃⁺-CH₂CH₂-SH, spirobisindane dioxin polymer] Y | [3-(trimethoxysilyl)propyl acrylate] R-9 |
| 112 | PAN | P-25 | [vinyltrimethoxysilane] Vinyltrimethoxysilane R-23 [tetramethoxygermane H₃CO-Ge(OCH₃)₃] R-5, R-23 |

[Additional polymer structures shown: P-25 (calixarene-type), polyimide with hexafluoroisopropylidene and N-substituents, P-3 (dithiol benzene and CO₂H substituted benzene copolymer)]

TABLE 1-continued

| Sample No. | Crosslinking temperature/Time | $CO_2$ permeability (GPU) | $CO_2/CH_4$ separation selectivity | Bending test (Membrane-forming competence) |
|---|---|---|---|---|
| 107 | Drying: 70° C./3 h, 120° C./2 h | 70 | 39 | A |
| 108 | Drying: 70° C./3 h, 100° C./2 h | 66 | 43 | A |
| 109 | Drying: 70° C./3 h, 100° C./2 h | 48 | 30 | A |
| 110 | Drying: 70° C./3 h, 100° C./2 h | 58 | 30 | A |
| 111 | Drying: 70° C./3 h, 100° C./2 h | 67 | 32 | A |
| 112 | Drying: 70° C./3 h | 82 | 37 | A |

| Sample No. | Support membrane | Polymer | Crosslinking agent |
|---|---|---|---|
| 113 | PAN | P-3 | 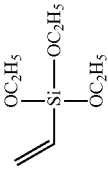 Vinyltriethoxysilane $C_2H_5O-Mg-OC_2H_5$ R-24 R-5, R-24 |
| 114 | PAN | P-3 | 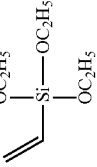 Vinyltriethoxysilane $(H_3C)_2HCO-Al\genfrac{}{}{0pt}{}{OCH(CH_3)_2}{OCH(CH_3)_2}$ R-25 R-5, R-25 |

TABLE 1-continued

| | | | | |
|---|---|---|---|---|
| 115 | PAN | P-3 | Vinyltriethoxysilane; $H_3CH_2CH_2CO-Zr-OCH_2CH_2CH_3$ with $OCH_2CH_2CH_3$ and $OCH_2CH_2CH_3$ substituents | R-26 |
| | | | | R-5, R-26 |
| 116 | PAN | P-3 | Vinyltriethoxysilane; $(H_3C)_2HCO-Ti-OCH(CH_3)_2$ with $OCH(CH_3)_2$ and $OCH(CH_3)_2$ substituents | R-27 |
| | | | | R-5, R-27 |
| 117 | PAN | P-3 | Vinyltriethoxysilane; $H_3CO-Sb-OCH_3$ with $OCH_3$ substituent | R-28 |
| | | | | R-5, R-28 |

Where the silane structure shown is vinyl-Si(OC$_2$H$_5$)$_3$ (vinyltriethoxysilane).

TABLE 1-continued
| Sample No. | | | |
|---|---|---|---|
| 118 | PAN | 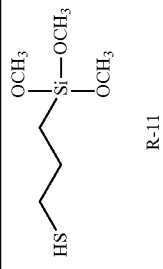 R-11 | 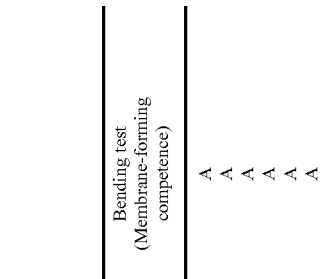 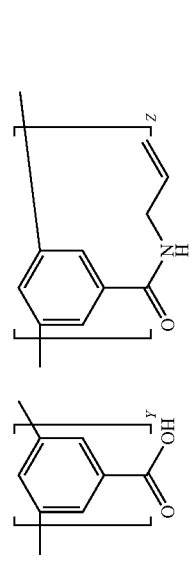 P-4 |
| Sample No. | Crosslinking temperature/Time | CO$_2$ permeability (GPU) | CO$_2$/CH$_4$ separation selectivity | Bending test (Membrane-forming competence) |
|---|---|---|---|---|
| 113 | Drying: 70° C./3 h | 53 | 31 | A |
| 114 | Drying: 70° C./3 h | 58 | 32 | A |
| 115 | Drying: 70° C./3 h | 67 | 33 | A |
| 116 | Drying: 70° C./3 h | 61 | 35 | A |
| 117 | Drying: 70° C./3 h | 43 | 31 | A |
| 118 | Drying: 70° C./3 h | 75 | 33 | A |

TABLE 1-continued

| Sample No. | Support membrane | Polymer | Crosslinking agent |
|---|---|---|---|
| 119 | PAN | P-5 | R-11 |
| 120 | PAN | P-19 | R-11 |

TABLE 1-continued

| 121 | PAN | P-26 | R-11 |
| c11 | PAN | | — |

TABLE 1-continued
| | | |
|---|---|---|
| c12 | PSf | 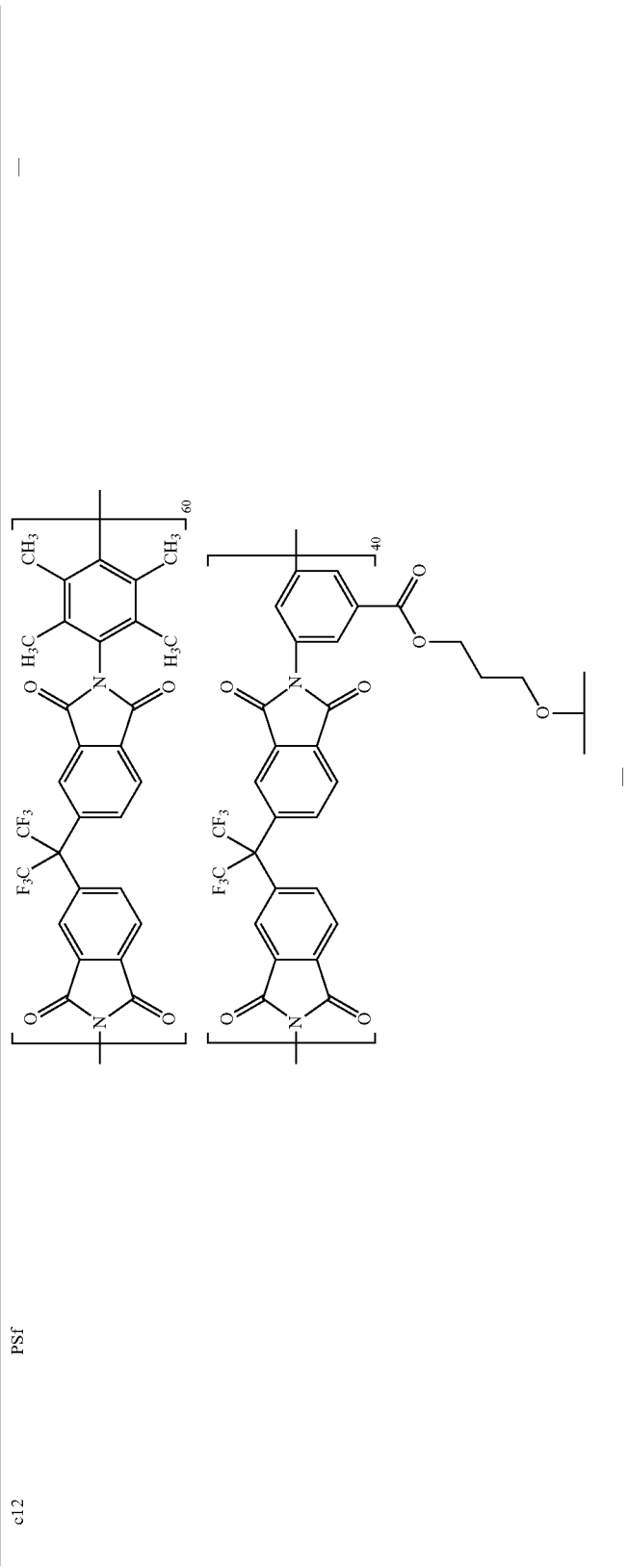 |

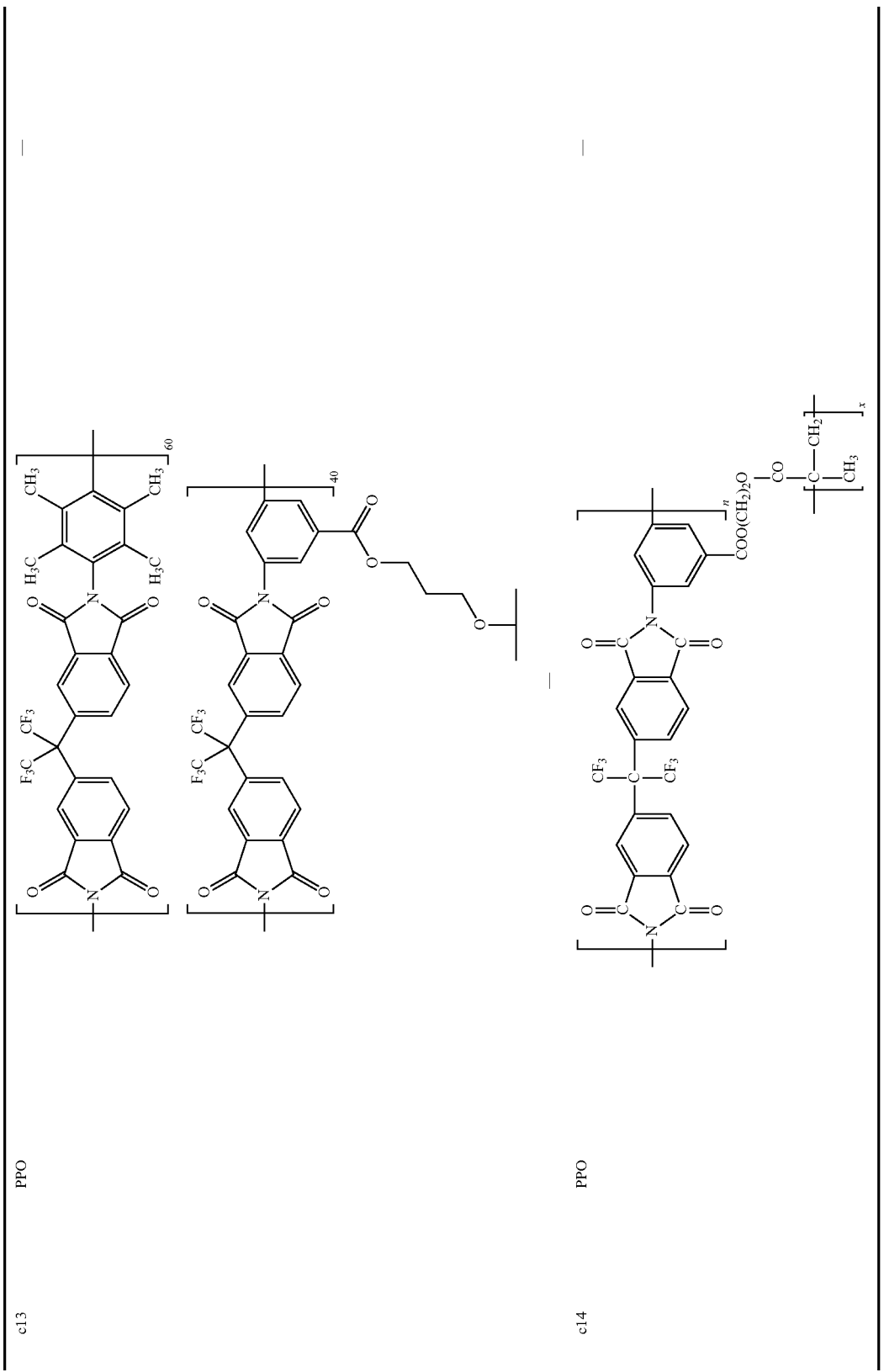

TABLE 1-continued

| Sample No. | Crosslinking temperature/Time | CO$_2$ permeability (GPU) | CO$_2$/CH$_4$ separation selectivity | Bending test (Membrane-forming competence) |
|---|---|---|---|---|
| 119 | Drying: 70° C./3 h | 68 | 34 | A |
| 120 | Drying: 70° C./3 h | 93 | 29 | A |
| 121 | Drying: 70° C./3 h | 89 | 27 | A |
| c11 | 150° C./25 h | The membrane was broken | — | B |
| c12 | 150° C./25 h | The membrane was broken | — | B |
| c13 | 80° C./60 min | 20 | 18 | B |
| c14 | 150° C./60 min 165° C./30 min 190° C./10 min | 11 | 21 | B |

| Sample No. | Supporting membrane | Polymer | Crosslinking agent |
|---|---|---|---|
| c15 | — | 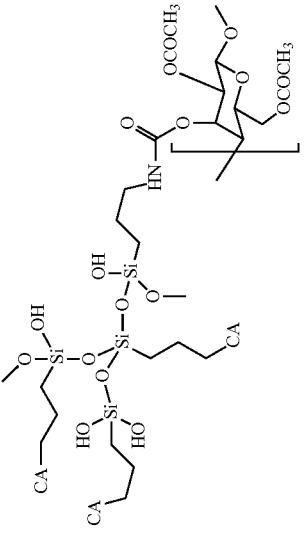 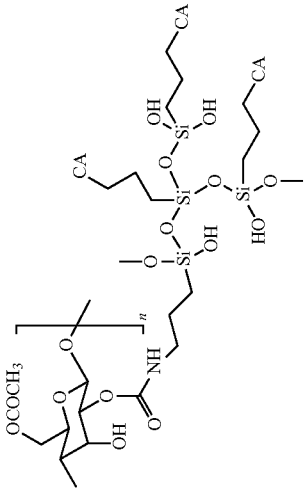 Polymer described in U.S. 2010/0326273 A1 | — |

TABLE 1-continued
c16 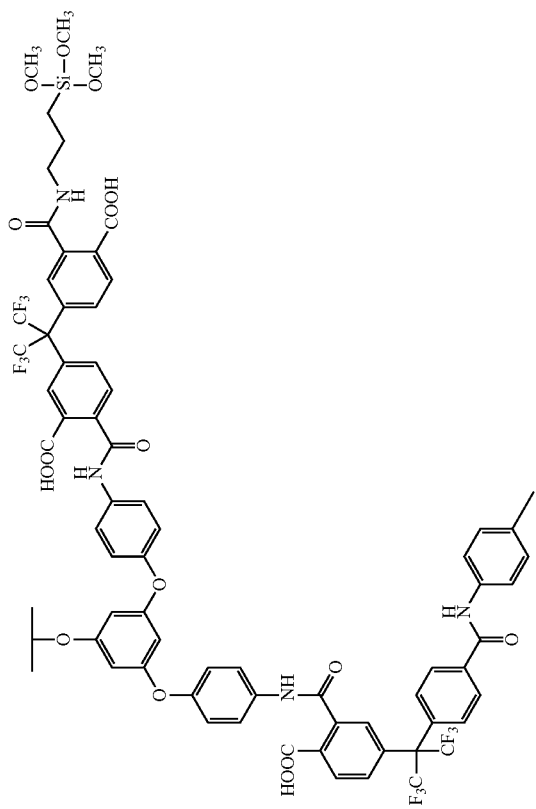

TABLE 1-continued
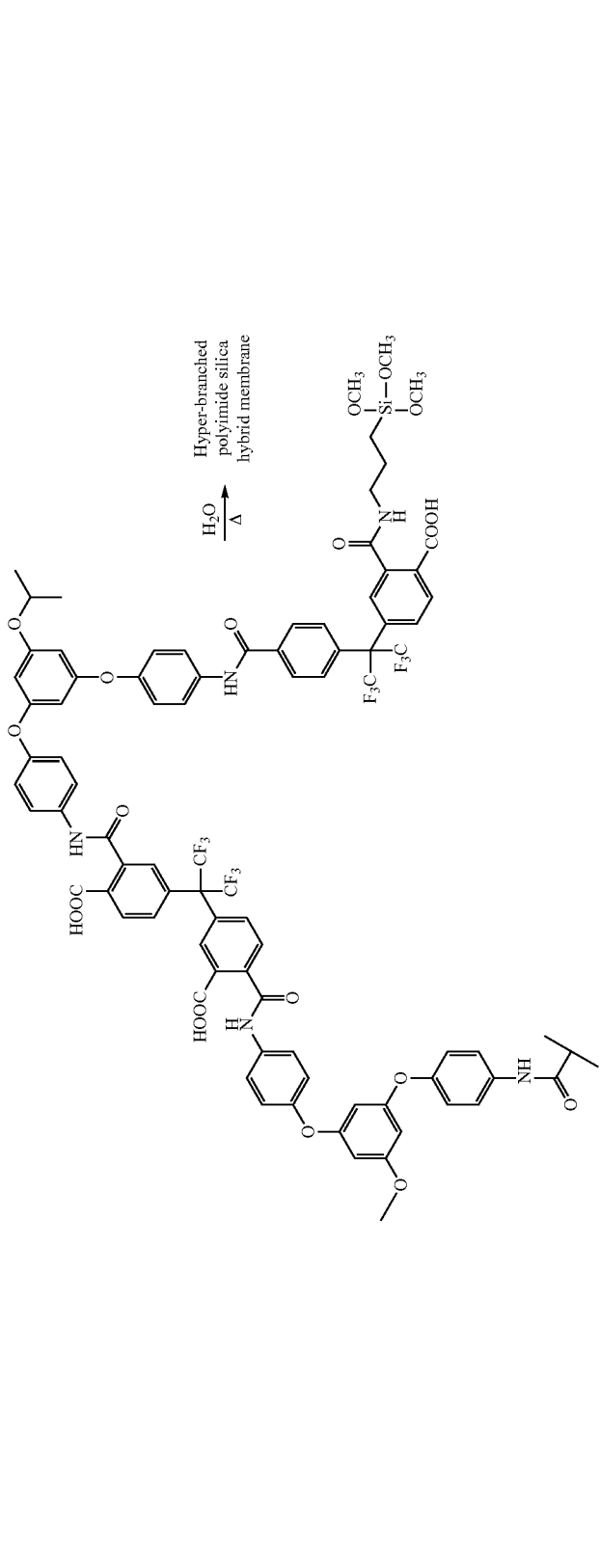
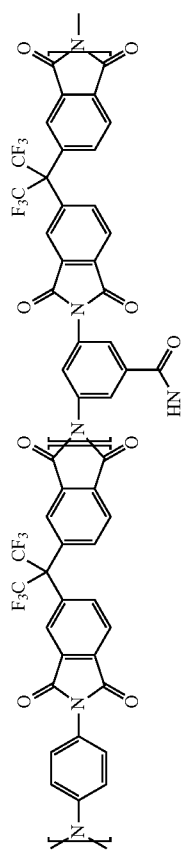
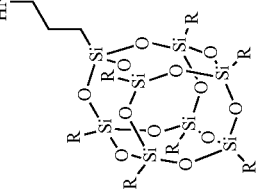

TABLE 1-continued

| Sample No. | Crosslinking temperature/Time | CO₂ permeability (GPU) | CO₂/CH₄ separation selectivity | Bending test (Membrane-forming competence) |
|---|---|---|---|---|
| c15 | 110° C./48 min | 0.7 | 20 | A |
| c16 | 100° C./60 min<br>200° C./60 min<br>300° C./60 min | 0.9 | 23 | A |
| c17 | 110° C./48 hrs | 11 | 12 | A |
| c18 | 220° C./60 min | 2.4 | 9.6 | A | c18: [structure shown]

PAN: Polyacrylonitrile
PSf: Polysulfone
PPO: Polyphenyleneoxide
PTFE: Polytetrafluoroethylene It should be noted that c17 and c18 are compounds synthesized in accordance with U.S. Pat. No. 7,619,042 and Journal of Membrane Science, 2002, 202, 97, respectively, and they are compounds which have been crosslinked by condensing the polymers having the above-described structures by hydrolysis thereof.
Room temperature: about 25° C.

The above-described results show that the gas separation membrane according to the present invention is excellent in both carbon dioxide permeability and separation selectivity, and also is provided with high bending strength.

Example 2 and Comparative Example 2

Sample Error Ratio

Were produced 50 samples of each of the gas separation membranes described above Examples and Comparative Examples, permeability of hydrogen of each sample at that time was measured, the sample having a gas permeance higher than $1\times10^6$ ml/m²·24 h·atm was defined as a membrane having pinholes, and a value obtained from dividing the number of membranes having pinholes by 50 was calculated as a sample error ratio.

The thus-obtained results of the sample error ratio of the gas separation membranes described in those Examples and Comparative examples are shown in Table 2.

TABLE 2

| Sample No. | Sample error ratio [%] |
| --- | --- |
| 101 | 6 |
| 102 | 4 |
| 103 | 12 |
| 104 | 6 |
| 105 | 8 |
| 106 | 6 |
| 107 | 8 |
| 108 | 4 |
| 109 | 4 |
| 110 | 4 |
| 111 | 4 |
| 112 | 6 |
| 113 | 4 |
| 114 | 6 |
| 115 | 6 |
| 116 | 8 |
| 117 | 8 |
| 118 | 4 |
| 119 | 4 |
| 120 | 6 |
| 121 | 12 |
| c11 | — |
| c12 | — |
| c13 | 46 |
| c14 | 66 |
| c15 | 12 |
| c16 | 18 |
| c17 | 14 |
| c18 | 20 |

From the above results, it is shown that a good membrane with few pinholes upon forming the gas separating layer can be prepared in the gas separation composite membrane of the present invention.

Example 3 and Comparative Example 3

Next, each of the gas separation composite membranes produced in Examples and Comparative Examples was stored under conditions of 80° C. and 90% humidity (low-temperature thermo-hygrostat, Suisho, Isuzu Seisakusho Co., Ltd.) for 24 hours, a gas permeability test was conducted in a manner similar to the operations described in the above, and the change of the $CO_2/CH_4$ separation selectivity was investigated. The results are shown below.

TABLE 3

| Sample No. | Separation selectivity | Separation selectivity (after wet heat test) |
| --- | --- | --- |
| 101 | 38 | 36 |
| 102 | 38 | 35 |
| 103 | 37 | 35 |
| 104 | 37 | 36 |
| 105 | 36 | 35 |
| 106 | 39 | 38 |
| 107 | 39 | 37 |
| 108 | 43 | 42 |
| 109 | 30 | 30 |
| 110 | 30 | 28 |
| 111 | 32 | 29 |
| 112 | 37 | 33 |
| 113 | 31 | 29 |
| 114 | 32 | 30 |
| 115 | 33 | 30 |
| 116 | 35 | 30 |
| 117 | 31 | 29 |
| 118 | 33 | 31 |
| 119 | 34 | 32 |
| 120 | 29 | 26 |
| 121 | 27 | 26 |
| c13 | 18 | 3.6 |
| c14 | 21 | 1.8 |
| c15 | 20 | 18 |
| c16 | 23 | 19 |
| c17 | 12 | 10 |
| c18 | 9.6 | 7.8 |

Example 4 and Comparative Example 4

Next, in a glass container which can be covered with a lid and is also filled with a toluene solvent, a 100 ml beaker was allowed to stand. Further in the beaker, gas separation composite membranes prepared in Examples and Comparative Examples were put, and by covering it with a glass cover, a hermetically-closed system was made. Then, after storage for 24 hours under the condition of 40° C., a gas permeability test was carried out in the same manner as described above. The results obtained by investigating changes of $CO_2/CH_4$ separation selectivity are shown below.

TABLE 4

| Sample No. | Separation selectivity | Separation selectivity (after toluene exposure test) |
| --- | --- | --- |
| 101 | 38 | 36 |
| 102 | 38 | 36 |
| 103 | 37 | 34 |
| 104 | 37 | 35 |
| 105 | 36 | 35 |
| 106 | 39 | 38 |
| 107 | 39 | 37 |
| 108 | 43 | 42 |
| 109 | 30 | 30 |
| 110 | 30 | 28 |
| 111 | 32 | 30 |
| 112 | 37 | 31 |
| 113 | 31 | 30 |
| 114 | 32 | 30 |
| 115 | 33 | 29 |
| 116 | 35 | 29 |
| 117 | 31 | 29 |
| 118 | 33 | 30 |
| 119 | 34 | 32 |
| 120 | 29 | 24 |
| 121 | 27 | 26 |
| c13 | 18 | 4.8 |
| c14 | 21 | 5.2 |
| c15 | 20 | 17 |
| c16 | 23 | 19 |

TABLE 4-continued

| Sample No. | Separation selectivity | Separation selectivity (after toluene exposure test) |
|---|---|---|
| c17 | 12 | 9.7 |
| c18 | 9.6 | 8.9 |

When the above-described results are generalized, it is found that the gas separation membrane of the present invention has excellent gas permeability and gas separation selectivity under high-pressure conditions, particularly excels in selective permeability of carbon dioxide, and excels as a carbon dioxide/methane separation membrane. Further, a composite membrane with strength can be produced at a low temperature in a short time, and therefore it excels in production competence. In addition, it is found that the gas separation membrane and the gas separation composite membrane of the present invention, which excels in hygrothermal aging and stability in the coexistence of toluene and exhibits a stable performance over a long period of time, allow provision of an excellent gas separation method, a gas separation membrane module, and a gas separation or gas refining apparatus in which a gas separation membrane module is installed.

Values of the crosslinked site ratio [η] and the crosslinking functional group density [γ] of each crosslinked resin were given in the following Table 5.

TABLE 5

| Sample No. | η | γ |
|---|---|---|
| 101 | 0.3 | 0.8 |
| 102 | 0.1 | 0.8 |
| 103 | 0.13 | 0.8 |
| 104 | 0.3 | 0.8 |
| 105 | 0.3 | 0.8 |
| 106 | 0.3 | 0.8 |
| 107 | 0.3 | 0.8 |
| 108 | 0.3 | 0.8 |
| 109 | 0.4 | 2.0 |
| 110 | 0.4 | 2.0 |
| 111 | 0.4 | 2.0 |
| 112 | 0.3 | 0.8 |
| 113 | 0.3 | 0.8 |
| 114 | 0.2 | 0.8 |
| 115 | 0.2 | 0.8 |
| 116 | 0.2 | 0.8 |
| 117 | 0.3 | 0.8 |
| 118 | 0.3 | 0.8 |
| 119 | 0.3 | 1.1 |
| 120 | 0.3 | 0.8 |
| 121 | 0.3 | 0.6 |
| c11 | 0.2 | 0.4 |
| c12 | 0.2 | 0.4 |
| c13 | 0.2 | 0.4 |
| c14 | 0.5 | 1.0 |
| c15 | 0.33 | 0.33 |
| c16 | 0.04 | 0.07 |
| c17 | 0.1 | 0.2 |
| c18 | 0.125 | 0.25 |

Reference Example

Next, using the separation membrane of the above-described Test No. 101, gas separation treatment tests were carried out under each of the conditions described below. The other conditions were the same as the above-described Examples. However, the separation treatment was carried out by changing the copolymerization ratio of polymer P-1 used in Test No. 101 as shown in the following Table 6.

TABLE 6

| Copoly-merization ratio | γ | 8 atmospheric pressure $CO_2/CH_4 = 1/1$ (vol/vol) mixed gas | 50 atmospheric pressure $CO_2/CH_4 = 1/1$ (vol/vol) mixed gas | 60 atmospheric pressure $CO_2/CH_4/C_4H_{12} = 1/8.5/0.5$ (vol/vol/vol) mixed gas |
|---|---|---|---|---|
| x/y = 80/20 | 0.2 | 550 (22) | 350 (14) | 200 (7) |
| x/y = 60/40 | 0.4 | 225 (35) | 150 (25) | 95 (10) |
| x/y = 40/60 | 0.6 | 81 (47) | 45 (18) | 15 (13) |
| x/y = 20/80 | 0.8 | 48 (50) | 25 (28) | 10 (23) |

As understood from the above-described results, it is found that adjustment of the crosslinkable functional group density [γ] of the raw resin allows setting of the permeability and the separation selectivity to an intended range. In particular, it is found that under the condition of such a high pressure as described above and under the condition of containing an organic compound of long-chain hydrocarbons, enhancement of γ is preferable, and it is possible to set the separation selectivity so as to exceed a practically-required range of from 10 to 20. Under low pressure conditions, or in the system free from a long-chain hydrocarbon gas, the foregoing tendency was not necessarily remarkable.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Gas separating layer
2 Porous layer
3 Nonwoven fabric layer
10 and 20 Gas separation composite membrane

The invention claimed is:
1. A gas separation composite membrane, containing:
a gas-permeable supporting layer; and
a gas separating layer containing a crosslinked organic-inorganic hybrid resin, over the gas-permeable supporting layer,
wherein the crosslinked organic-inorganic hybrid resin has a structure in which a polymer incorporating therein an oxanthrene unit, or a polyimide compound has been crosslinked via a specific crosslinking chain, and the specific crosslinking chain contains a site represented by the following formula (A):

wherein $R^a$ represents an alkyl group, a cycloalkyl group, an aryl group, an alkoxy group, an aryloxy group, or *—O—**; the symbol "*" means a bonding hand with $M^1$ in formula (A); the symbol "**" means a connection site with an adjacent $M^1$; $M^1$ represents a metal atom selected from the group consisting of Si, Ge, Mg, Al, Ti, Zr and Sb; $P^a$ represents a polyimide compound or a polymer incorporating therein an oxanthrene unit; and $L^a$ represents a connection site with an adjacent $M^1$, wherein a structural part derived from the polyimide compound contains a repeating unit represented by formula (I), and a repeating unit represented by formula (III-a) or (III-b):

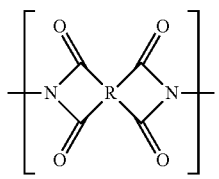
(I)

wherein, in formula (I), R is a group of atoms selected from groups represented by formulas (I-a) to (I-g);

wherein, in formulas (I-a) to (I-g), $X^1$ represents a single bond or a divalent linking group; Y represents a methylene group or a vinylene group; $R^1$ and $R^2$ each independently represent a hydrogen atom or a substituent, or may bond with each other to form a ring; and the symbol "*" represents a binding site with the carbonyl group of the imide in formula (I);

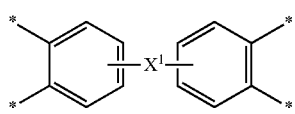
(I-a)

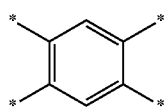
(I-b)

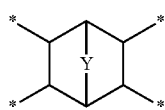
(I-c)

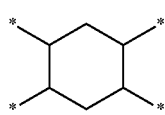
(I-d)

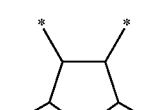
(I-e)

(I-f)

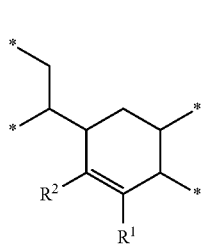

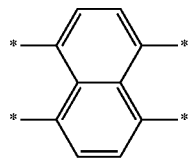
(I-g)

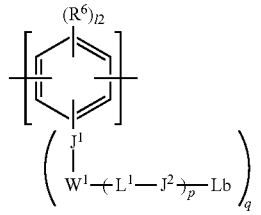
(III-a)

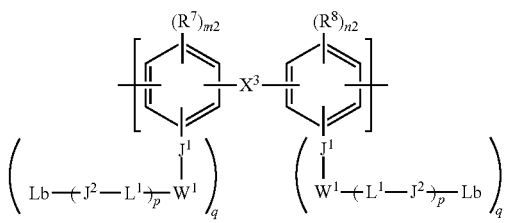
(III-b)

wherein $R^6$, $R^7$ and $R^8$ represent a substituent; $J^1$, $J^2$ and $W^1$ represent a single bond or a divalent linking group; l2, m2 and n2 represent an integer of from 0 to 3; $L^1$ represents a divalent linking group; p represents an integer of 0 or more; q represents an integer of 1 or more; $X^3$ represents a single bond or a divalent linking group; and Lb means a connection site with $M^1$ in formula (A), and wherein the polymer incorporating therein an oxanthrene unit contains a repeating unit represented by formula (IV-a), and a repeating unit represented by formula (IV-b):

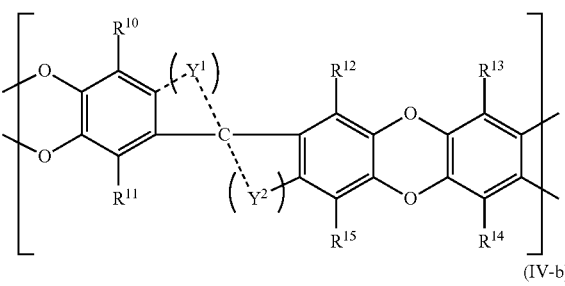
(IV-a)

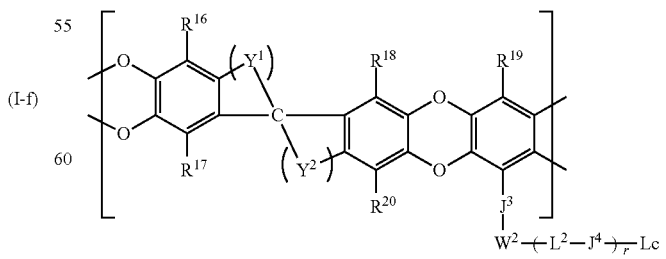
(IV-b)

wherein $R^{10}$ to $R^{20}$ represent a hydrogen atom or a substituent; $J^3$, $J^4$ and $W^2$ represent a single bond or a divalent linking group; L² represents a divalent linking group; r represents an integer of 0 or more; Y¹ and Y² represent a group of atoms for forming a ring with the carbon atom and the benzene ring; Lc means a connection site with M¹ in formula (A).

2. The gas separation composite membrane according to claim 1, wherein the structural part derived from the polyimide compound further contains a repeating unit represented by formula (II-a) or (II-b):

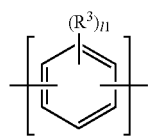
(II-a)

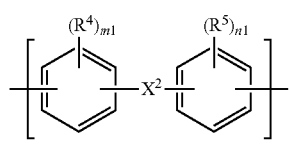
(II-b)

wherein $R^3$, $R^4$ and $R^5$ represent an alkyl group, a hydroxyl group, a carboxyl group, a sulfonic acid group, an amino group, a mercapto group, an amide group, an alkoxy group, a sulfone group, or a halogen atom; l1, m1 and n1 represent an integer of from 0 to 4; and $X^2$ represents a single bond or a divalent linking group.

3. The gas separation composite membrane according to claim 1, wherein the polymer incorporating therein an oxanthrene unit is a resin with inherent microporosity (PIM).

4. The gas separation composite membrane according to claim 1,
wherein a gas to be supplied is a mixed gas of carbon dioxide and methane,
wherein a transmission rate of the carbon dioxide at 40° C. and 40 atmospheric pressure is more than 20 GPU, and
wherein a ratio of the transmission rate of the carbon dioxide to a transmission rate of the methane ($R_{CO2}/R_{CH4}$) is 15 or more.

5. The gas separation composite membrane according to claim 1, wherein the supporting layer contains a porous layer on a side of the gas separating layer and a nonwoven fabric layer on a side reverse thereto.

6. The gas separation composite membrane according to claim 5, wherein the porous layer has a molecular weight cut-off of 100,000 or less.

7. The gas separation composite membrane according to claim 1, wherein a crosslinked site ratio [η] of the crosslinked organic-inorganic hybrid resin is 0.13 or more.

8. The gas separation composite membrane according to claim 1, wherein a crosslinking functional group density [γ] of a raw resin that constitutes the crosslinked organic-inorganic hybrid resin is from 0.7 to 0.95.

9. The gas separation composite membrane according to claim 1, wherein the crosslinked organic-inorganic hybrid resin is formed by using a compound represented by the following formula (O-1), (O-2), or (O-3) as a crosslinking agent that constitutes the crosslinking chain thereof:

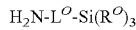  O-1

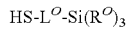  O-2

  O-3 wherein $L^O$ represents a single bond or a linking group; and $R^O$ represents an alkoxy group.

10. A method of producing a gas separation composite membrane having a gas separating layer containing a crosslinked organic-inorganic hybrid resin over a gas-permeable supporting layer thereof, comprising:

coating a coating liquid containing a polyimide compound or a polymer incorporating therein an oxanthrene unit, and a crosslinking agent having a metal atom M¹ wherein M¹ represents a metal atom selected from the group consisting of Si, Ge, Mg, Al, Ti, Zr, and Sb, over the supporting layer; and irradiating an active radiation or applying heat to the coating liquid thereby inducing a crosslinking reaction, wherein the polyimide compound contains a repeating unit represented by formula (I), and a repeating unit represented by formula (VI-a) or (VI-b):

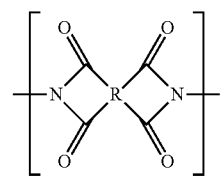
(I)

wherein, in formula (I), R is a group of atoms selected from groups represented by formulas (I-a) to (I-g);
wherein, in formulas (I-a) to (I-g), $X^1$ represents a single bond or a divalent linking group; Y represents a methylene group or a vinylene group; $R^1$ and $R^2$ each independently represent a hydrogen atom or a substituent, or may bond with each other to form a ring; and the symbol "*" represents a binding site with the carbonyl group of the imide in formula (I);

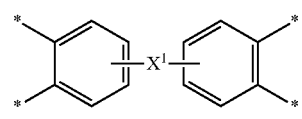
(I-a)

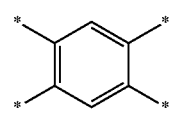
(I-b)

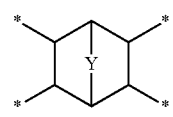
(I-c)

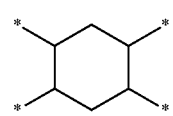
(I-d)

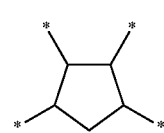
(I-e)

-continued (I-f)
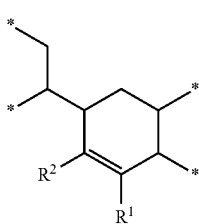

(I-g)
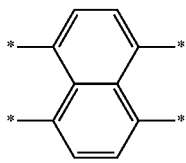

(VI-a)
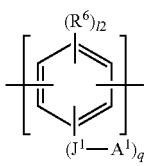

(VI-b)
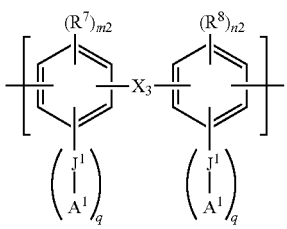

wherein $R^6$, $R^7$ and $R^8$ represent a substituent; $J^1$ represents a single bond or a divalent linking group; l2, m2 and n2 represent an integer of from 0 to 3; q represents an integer of 1 or more and 4 or less; $X^3$ represents a single bond or a divalent linking group; and $A^1$ represents a reactive group, and wherein the polymer incorporating therein an oxanthrene unit is a polymer containing a repeating unit represented by formula (V):

(V)
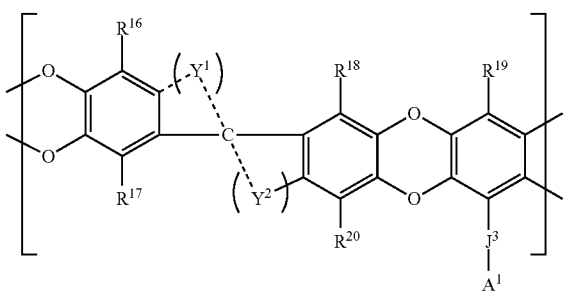

wherein $R^{16}$ to $R^{20}$ represent a hydrogen atom or a substituent; $J^3$ represents a single bond or a divalent linking group; $Y^1$ and $Y^2$ represent a group of atoms for forming a ring with the carbon atom and the benzene ring; and $A^1$ represents a hydroxy group, a carboxyl group, a sulfonic acid group, an alkenyl group, an alkynyl group, or a mercapto group, and wherein the polyimide compound further contains a repeating unit represented by formula (II-a):

(II-a)

wherein $R^3$ represents a substituent; and l1 represents an integer of from 0 to 4.

11. The method of producing the organic-inorganic hybrid gas separation composite membrane according to claim 10, wherein the crosslinking agent is a compound represented by formula (B): (B):

(B)

wherein $A^2$ represents a reactive group; $L^3$ represents a single bond or a divalent linking group; $R^{21}$, $R^{22}$ and $R^{23}$ represent an alkyl group, a cycloalkyl group, an aryl group, an alkoxy group, or an aryloxy group; and $M^1$ has the same meaning as that described above.

12. The method of producing a gas separation composite membrane according to claim 11, wherein the crosslinking agent is a compound represented by formula (O-1), (O-2) or (O-3):

$H_2N-L^O-Si(R^O)_3$   O-1

$HS-L^O-Si(R^O)_3$   O-2

$CH_2=CH-L^O-Si(R^O)_3$   O-3 wherein $L^O$ represents a single bond or a divalent linking group; and $R^O$ represents an alkyl group, an aryl group, an alkoxy group, or an aryloxy group.

13. A gas separation module, containing the gas separation composite membrane according to claim 1.

14. A gas separation apparatus, containing the gas separation module according to claim 13.

15. A gas separation method, which contains a step of selectively permeating carbon dioxide from a gas containing carbon dioxide and methane by using the gas separation composite membrane according to claim 1.

* * * * *